United States Patent [19]
Fisher et al.

[11] Patent Number: 6,137,002
[45] Date of Patent: *Oct. 24, 2000

[54] GLYCOPROTEIN IIB/IIIA ANTAGONISTS

[75] Inventors: Matthew J. Fisher, Carmel; Anne Marie Happ, Indianapolis; Joseph A. Jakubowski, Indianapolis; Michael Dean Kinnick, Indianapolis; Allen D. Kline, Bargersville; John Michael Morin, Jr., Brownsburg; Daniel J. Sall, Greenwood; Marshall A. Skelton; Robert Theodore Vasileff, both of Indianapolis, all of Ind.

[73] Assignee: Eli Lilly and Company, Indianapolis, Ind.

[*] Notice: This patent is subject to a terminal disclaimer.

[21] Appl. No.: 08/710,823

[22] Filed: Sep. 23, 1996

Related U.S. Application Data

[63] Continuation-in-part of application No. 08/255,821, Jul. 8, 1994, Pat. No. 5,618,843, which is a continuation-in-part of application No. 08/096,220, Jul. 22, 1993, abandoned.

[51] Int. Cl.$^7$ ............................................. C07C 251/02
[52] U.S. Cl. ............................................. 562/440
[58] Field of Search .................................... 562/440

[56] References Cited

U.S. PATENT DOCUMENTS

| | | |
|---|---|---|
| 4,026,907 | 5/1977 | Scott et al. . |
| 4,752,646 | 6/1988 | Cohen . |
| 4,789,750 | 12/1988 | Coffen et al. . |
| 4,806,661 | 2/1989 | Cohen . |
| 4,853,472 | 8/1989 | Coffen et al. . |
| 5,039,805 | 8/1991 | Alig et al. ................ 546/224 |
| 5,041,453 | 8/1991 | Huang et al. ............. 514/314 |
| 5,064,814 | 11/1991 | Klein et al. ................ 514/18 |

FOREIGN PATENT DOCUMENTS

| | | | |
|---|---|---|---|
| 0 169 443 | 1/1986 | European Pat. Off. ...... C07D 237/26 |
| 0 315 399 | 11/1988 | European Pat. Off. ................. 514/18 |
| 0 430 459 | 11/1990 | European Pat. Off. ...... C07C 311/20 |
| 0 435 235 | 7/1991 | European Pat. Off. ...... C07D 217/02 |
| 0 456 835 | 11/1991 | European Pat. Off. ................ 544/253 |
| 0 4531 883 | 3/1992 | European Pat. Off. . |
| 0 478 328 | 4/1992 | European Pat. Off. ...... C07C 271/22 |
| 0 540 051 | 5/1993 | European Pat. Off. ...... C07C 257/18 |
| 2 276 384 | 9/1994 | United Kingdom ......... C07D 209/46 |
| WO 89/04303 | 1/1989 | WIPO ..................................... 514/18 |
| WO 89/04304 | 1/1989 | WIPO ..................................... 514/18 |
| WO 92/20705 | 11/1992 | WIPO ............................. C07K 5/02 |
| WO 93/00095 | 1/1993 | WIPO ................................... 540/484 |
| WO 93/08174 | 4/1993 | WIPO ................................... 540/484 |
| WO 93/12074 | 6/1993 | WIPO .......................... C07C 257/18 |
| WO 94/29273 | 12/1994 | WIPO .......................... C07D 215/14 |

OTHER PUBLICATIONS

*Chemical Abstracts*, vol., 84, N. 13, Abstract 90500Z, Mar. 29, 1976, p. 566, Barxzai–Beke et al.

McDowell et al., 1994 *Journal American Chemical Society*, Vo. 116, 5077–5083.

*Chemical Abstracts*, vol. 75, N. 10, Abstract 74391y, Sep. 6, 1971, p. 278, Satoh et al.

Ku et al., 1993 *Journal American Chemical Society*, vol. 115, 8861–8862.

Blackburn et al., 1993 *Annual Reports in Medicinal Chemisty*, vol. 28, 79–88.

*Chemical Abstracts*, vol. 100, N. 17, Abstract 138973n, Apr. 23, 1984, p. 638, Otsuka Pharmaceutical Co.

*Journal of Medicinal Chemistry*, Vo. 21, No. 11, 1978, Ellis et al., "Benzopyrones. 14 Synthesis and Antiallergic Properties of Some N–Tetrazolyl Carboxamides and Related Compounds", pp. 1120–1126.

*Primary Examiner*—Robert Gerstl
*Attorney, Agent, or Firm*—Knobbe, Martens, Olson & Bear, LLP

[57] ABSTRACT

This invention relates to certain bicyclic compounds having a nucleus formed of two fused six membered rings, for example, isoquinoline, isoquinolone, tetrahydronaphthalene, dihydronaphthalene, or tetralone, substituted with both basic and acidic functionality, which are useful in inhibition of platelet aggregation.

12 Claims, No Drawings

GLYCOPROTEIN IIB/IIIA ANTAGONISTS

CROSS-REFERENCE TO RELATED APPLICATIONS

This application is a continuation-in-part of application Ser. No. 08/255,821, now U.S. Pat. No. 5,618,843 filed Jul. 8, 1994 which is a continuation-in-part of Ser. No. 08/096,220 filed Jul. 22, 1993, now abandoned.

FIELD OF THE INVENTION

This invention relates to bicyclic compounds useful as glycoprotein IIb/IIIa antagonists for the prevention of thrombosis.

BACKGROUND OF THE INVENTION

The most prevalent vascular disease states are related to platelet dependent narrowing of the blood supply such as atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, anastomosis of vascular grafts, and etc. These conditions represent a variety of disorders thought to be initiated by platelet activation on vessel walls.

Platelet adhesion and aggregation is believed to be an important part of thrombus formation. This activity is mediated by a number of platelet adhesive glycoproteins. The binding sites for fibrinogen, fibronectin and other clotting factors have been located on the platelet membrane glycoprotein complex IIb/IIIa. When a platelet is activated by an agonist such as thrombin the GPIIb/IIIa binding site becomes available to fibrinogen, eventually resulting in platelet aggregation and clot formation.

Heretofore it has been proposed to block these thrombus formation sites by the use of various therapeutic agents U.S. Pat. No. 5,064,814 teaches N-amidino-piperidine carboxyl cyclic amino acid derivatives as anti-thrombotic agents.

U.S. Pat. No. 5,039,805 teaches various benzoic acid and phenylacetic acid derivatives for the inhibition of the binding of fibrinogen to the fibrinogen receptor, glycoprotein IIb/IIIa.

Seven membered ring containing bicyclic compounds are taught to be fibrinogen antagonists in PCT International patent application WO 93/00095.

EP 456835 describes bicyclic compounds having fused six membered rings (quinazoline-3-alkanoic acid derivates) which are reported to have an inhibitory effect on platelet aggregation.

PCT International patent application WO 93/08174 describes nonpeptidyl integrin inhibitors which are bicyclic 6 and 7 membered fused ring systems which have therapeutic applications in diseases for which blocking platelet aggregation is indicated.

Quinoline compounds have been recited in the patent literature for a variety of medicinal uses. For example, European Patent Application 0 315 399; U.S. Pat. No. 5,041,453; PCT Patent Application WO 89/04303, and PCT Patent Application WO 89/04304 describe quinoline derivatives useful as lipoxygenase inhibitors and/or leukotriene antagonists possessing anti-inflammatory and anti-allergic properties. These compounds must contain three aromatic rings, each interrupted with oxygen, or sulfur, and possibly other groups.

There is a need in the area of cardiovascular and cerebrovascular therapeutics for alternative agents which can be used in the prevention and treatment of thrombi.

It is a discovery of this invention that certain novel bicyclic compounds block the GPIIb/IIIa fibrinogen receptor, thereby inhibiting platelet aggregation and subsequent thrombus formation. Pharmaceutical formulations containing the bicyclic compounds of this invention inhibit aggregation and are useful for the prophylaxis and treatment of thrombogenic diseases, such as myocardial infarction, angina, stroke, peripheral arterial disease, disseminated intravascular coagulation and venous thrombosis.

SUMMARY OF THE INVENTION

The present invention is a novel bicyclic compound having a nucleus formed from two fused six membered rings, A and B, represented by the formula (I), as hereinafter defined, and all pharmaceutically acceptable salts, solvates and prodrug derivatives thereof:

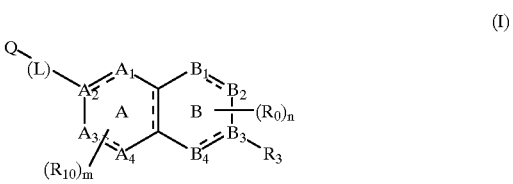

(I)

Another aspect of the invention is a pharmaceutical formulation containing the novel bicyclic compounds of the invention.

Another aspect of the invention is a method of inhibiting platelet aggregation, inhibiting fibrinogen binding, or preventing thrombosis by administering to a mammal the bicyclic compounds of the invention.

Another aspect of this invention is a method of treating a human to alleviate the pathological effects of atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy and anastomosis of vascular grafts; wherein the method comprises administering to said human the novel bicyclic compound of this invention.

DETAILED DESCRIPTION OF THE INVENTION

The term "alkyl" used herein refers to a monovalent straight or branched chain radical of from one to ten carbon atoms, including, but not limited to methyl, ethyl, n-propyl, isopropyl, n-butyl, isobutyl, tert-butyl, n-hexyl, and the like.

The term, "halosubstituted alkyl" as used herein refers to an alkyl group as just defined, substituted by one, two or three halogen atoms selected from fluorine, chlorine, bromine, and iodine. Examples of such groups include chloromethyl, bromoethyl, trifluoromethyl, and the like.

The term, "aryl", when used alone means a homocyclic aromatic radical whether or not fused. Preferred aryl groups include phenyl, napthyl, biphenyl, phenanthrenyl, naphthacenyl, and the like.

The term, "substituted aryl", denotes an aryl group substituted with one, two, or three substituents chosen from halogen, hydroxy, protected hydroxy, cyano, nitro, $C_1$–$C_{10}$ alkyl, $C_1$–$C_{10}$ alkoxy, trifluoromethyl, amino, aminomethyl, and the like. Examples of such groups are 4-chlorophenyl, 2-methylphenyl, 3-methyl-4-hydroxyphenyl, and 3-ethoxyphenyl.

The term, "arylalkyl", means one, two or three aryl groups having the number of carbon atoms designated, appended to an alkyl radical having the number of carbon atoms designated. A typical arylalkyl group is the benzyl group.

The term "alkenyl" as used herein refers to a monovalent straight or branched chain radical of from two to six carbon atoms containing a carbon double bond including, but not limited to, 1-propenyl, 2-propenyl, 2-methyl-1-propenyl, 1-butenyl, 2-butenyl and the like.

The term, "alkylene" as used herein refers to a divalent straight or branched chain group of from one to ten carbon atoms, including but not limited to, —CH$_2$—, —(CH$_2$)$_2$—, —(CH$_2$)$_3$—, —CH(CH$_3$)—, —CH(C$_2$H$_5$)—, —CH(CH$_3$)CH$_2$—, and the like.

The term "alkenylene" as used herein refers to a divalent straight or branched chain group of from two to ten carbon atoms containing a carbon-carbon double bond, including but not limited to, —CH=CH—, —C(CH$_3$)=CH—, CH=CH—CH$_2$—, —CH=C(CH$_3$)—CH$_2$—, —CH$_2$CH(CH=CH$_2$)CH$_2$ and the like.

The term, "alkynylene" as used herein refers to a divalent straight or branched chain group of from two to ten carbon atoms containing a carbon-carbon triple bond, including but not limited to,

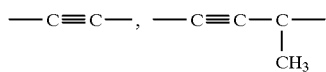

and the like.

The term, "amidino" refers to the radical having the structural formula;

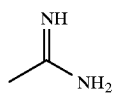

The term, "basic radical" refers to an organic radical which is a proton acceptor. Illustrative basic radicals are amidino, piperidyl, guanidino, and amino.

The term, "basic group" refers to an organic group containing one or more basic radicals. A basic group may comprise only an basic radical.

The term, "acid radical" refers to an organic radical which is a proton donor. Illustrative acid radicals include;

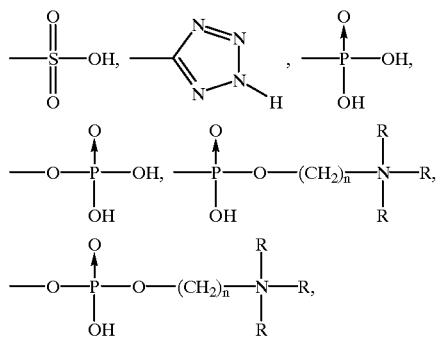

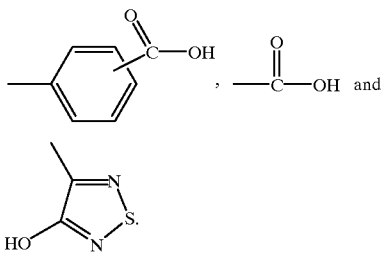

The term, "acidic group" is an organic group containing one or more acid radicals. An acidic group may comprise only an acid radical.

Compounds of the Invention:

Compounds of this invention have the general formula (I) shown below:

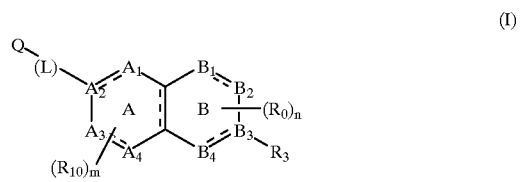

(I)

and all pharmaceutically acceptable salts, solvates and prodrug derivatives thereof.

The bicyclic nucleus of (I) is formed from the fusion of two six membered rings "A" and "B" having carbon bridging atoms. The dashed lines in the structural formula (I) signify the optional presence of an additional bond, that is, unsaturation that will lend aromatic character to the ring structure. It will be understood that the bridging carbon atoms will either be unsubstituted or substituted (with hydrogen) depending on the degree of unsaturation in the bicyclic ring system. The B ring atoms $B_1$, $B_2$, $B_3$, $B_4$ of formula (I) are independently selected from carbon, oxygen, sulfur, and nitrogen, with the proviso that at least two of $B_1$, $B_2$, $B_3$, $B_4$ are carbon. Thus, for example, the bicyclic nucleus of the compounds of the invention may be formed from ring systems inclusive of, but not limited to, any of the nuclei (a through r) depicted below:

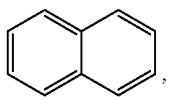
(a)

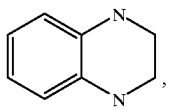
(b)

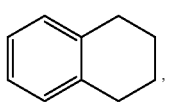
(c)

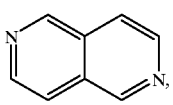
(d)

(e) 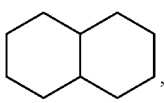

(f) 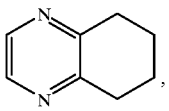

(g) 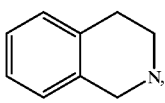

(h) 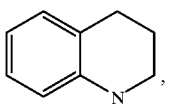

(i) 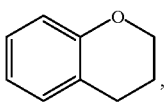

(j) 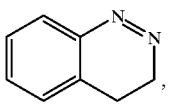

(k) 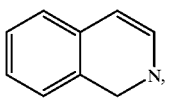

(l) 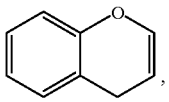

(m) 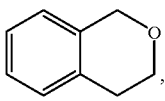

(n) 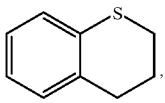

(o) 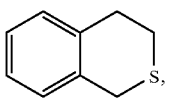

(p) 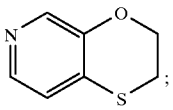

(q) 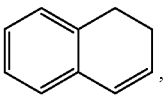

(r) 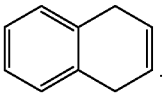

The most preferred nuclei for the compounds of this invention are isoquinoline, isoquinolone, naphthalene, tetrahydronapthalene, tetralone, dihydronaphthalene, and benzopyran.

The substituent $R_3$ is an acidic group or a pharmaceutically acceptable salt or solvate thereof, (or a prodrug derivative of said acidic group) and preferably is an acidic group containing carboxyl functionality. The $R_3$ group may be the sole substituent of ring atom $B_3$. Alternatively, when the $B_3$ atom can accept two bonds, these bonds may be satisfied by a double bond on the $R_3$ group (with the $R_3$ double bond attached directly to the B ring of formula I), or another $R_3$ group, or a group selected from hydrogen, $C_1$–$C_{10}$ alkyl, $C_1$–$C_{10}$ halosubstituted alkyl, $C_2$–$C_{10}$ alkenyl, $C_2$–$C_{10}$ alkynyl, $C_3$–$C_{10}$ cycloalkyl, aryl, $C_7$–$C_{12}$ aralkyl, hydroxy, $C_1$–$C_{10}$ alkoxy, $C_1$–$C_{10}$ aralkoxy, carboxy, acyl, cyano, halo, nitro, and sulfo.

$R_3$, the acidic group, is preferably selected from the group having members represented by the following formulae:

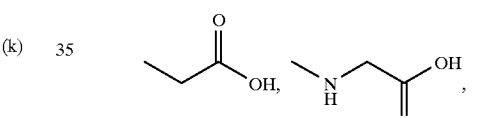

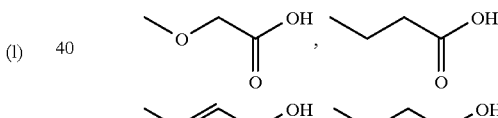

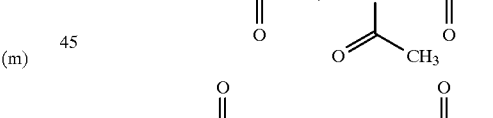

The substituents $R_0$ are the same or different on each atom $B_1$, $B_2$, and $B_4$ and the same or different between atoms $B_1$, $B_2$, and $B_4$ and are independently selected from hydrogen, $C_1$–$C_{10}$ alkyl, $C_1$–$C_{10}$ halosubstituted alkyl, $C_2$–$C_{10}$ alkenyl, $C_2$–$C_{10}$ alkynyl, $C_3$–$C_{10}$ cycloalkyl, aryl, $C_6$–$C_{12}$ arylalkyl, hydroxy, $C_1$–$C_{10}$ alkoxy, $C_6$–$C_{12}$ arylalkoxy, amino, substituted amino, carbamyl, carboxy, acyl, cyano, halo, nitro, sulfo; with the proviso that only one of $B_1$, $B_2$, and $B_4$ may also be substituted with =O or =S.

The number, n, of $R_0$ substituents attached to the atoms $B_1$, $B_2$, and $B_4$ of the B ring is an integer from 2 to 6 and depends on the sum of the number of unsatisfied bonds present in the individual atoms $B_1$, $B_2$, and $B_4$. Thus, for example, where the B ring is saturated, $B_2$ is oxygen, and $B_1$ and $B_4$ are carbon, then no $R_0$ substituent will be present on atom $B_2$ as shown in structural formula Ia below:

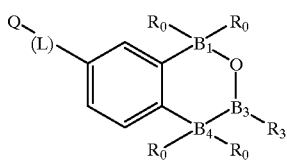

(Ia)

For B rings having unsaturation, the number of unsatisfied bonds present in the individual atoms $B_1$, $B_2$, and $B_4$ is decreased and the number of $R_0$ substituents required is correspondingly less. Thus, for example, where the B ring is unsaturated, $B_2$ is nitrogen, and $B_1$ and $B_4$ are carbon, then no $R_0$ substituent will be present on $B_2$ as shown in structural formula Ib below:

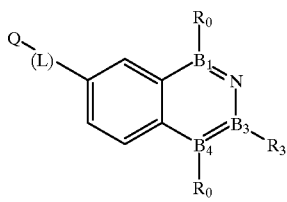

(Ib)

When the B ring has one $R_0$ substituent which is carbonyl, then preferred bicyclic nuclei of the invention include, but are not limited to, any of structures (s) through (x) depicted below:

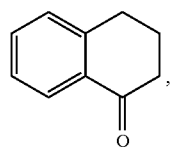

(s)

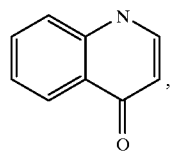

(t)

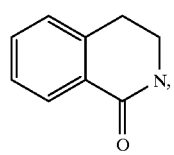

(u)

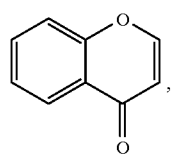

(v)

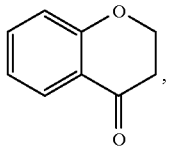

(w)

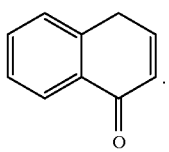

(x)

The A ring atoms $A_1$, $A_2$, $A_3$, and $A_4$ are independently selected from carbon, oxygen, sulfur, and nitrogen, with the proviso that at least two of $A_1$, $A_2$, $A_3$, and $A_4$ are carbon.

The substituents $R_{10}$ are the same or different on each atom $A_1$, $A_3$, and $A_4$ and the same or different between atoms $A_1$, $A_3$ and $A_4$, and are independently selected from hydrogen, $C_1$–$C_{10}$ alkyl, $C_1$–$C_{10}$ halosubstituted alkyl, $C_2$–$C_{10}$ alkenyl, $C_2$–$C_{10}$ alkynyl, $C_3$–$C_{10}$ cycloalkyl, aryl, $C_6$–$C_{12}$ arylalkyl, hydroxy, alkoxy, $C_6$–$C_{12}$ arylalkoxy, carboxy, acyl, cyano, halo, nitro, and sulfo; with the proviso that only one of $A_1$, $A_3$, and $A_4$ may also be substituted with =O or =S when two sites are available for substitution on a single atom (viz., when one or more of the dashed lines in the A ring of Formula I are absent and an A atom is carbon).

The number, m, or $R_{10}$ substituents attached to the atoms $A_1$, $A_3$, and $A_4$ of the A ring is an integer from 2 to 6 and depends on the sum of the number of unsatisfied bonds present in the individual atoms $A_1$, $A_3$, and $A_4$ in a manner analogous to the substitution of $R_0$ groups on the B ring as described above. The atom, $A_2$, of the A ring is substituted by linking group —(L)— alone when $A_2$ has only one unsatisfied bond, however, when $A_2$ has two unsatisfied bonds the second bond may be satisfied by a group selected from hydrogen, alkyl, halosubstituted $C_1$–$C_{10}$ alkyl, $C_2$–$C_{10}$ alkenyl, $C_2$–$C_{10}$ alkynyl, $C_3$–$C_{10}$ cycloalkyl, aryl, $C_7$–$C_{12}$ arylalkyl, hydroxy, $C_1$–$C_{10}$ alkoxy, $C_7$–$C_{12}$ arylalkoxy, acyl, cyano, halo, nitro, sulfo, and a basic group.

The linking group —(L)— attached to the $A_2$ atom of the A ring and is (i) a bond, or (ii) a divalent substituted or unsubstituted chain of from 1 to 10 atoms (viz., there are 1 to 10 atoms in the chain between the linking divalent bonds, with all other atoms pendent from these chain atoms). For example, when —(L)— is a bond the compound of the invention may have the structural formula Ic as follows:

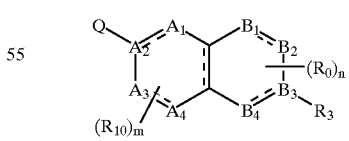

(Ic)

Alternatively, when —(L)— is the linking group

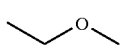

the compound of the invention may have the structural formula Id as follows:

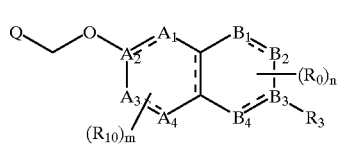
(Id)

Alkylene, alkenylene and alkynylene groups are suitable as linking groups. Preferred linking groups have 1 to 4 chain atoms and correspond to the general formulae:

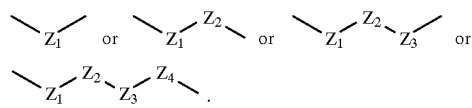

where $Z_1$, $Z_2$, $Z_3$, and $Z_4$ are atoms selected from the group consisting of carbon, nitrogen, sulfur, and oxygen. Linking groups containing three chain atoms such as,

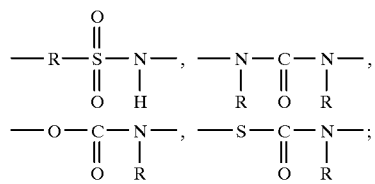

where R is hydrogen or alkyl, may be used.

Particularly preferred are linking groups containing two chain atoms such as;

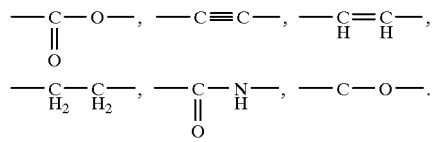

The linking group;

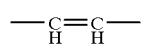

has cis and trans forms and both such forms and their mixtures in all proportions are within this invention.

Asymmetric linkers, for example, the linkers

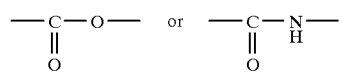

may be reversed in their point of attachment between the nucleus A ring and the basic group Q, as depicted in formulae (Ie) and (If) below:

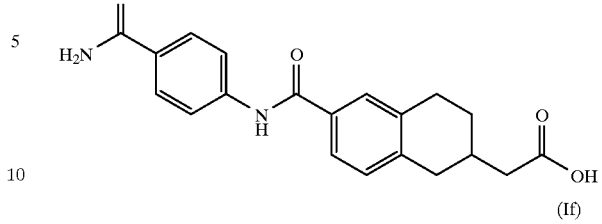
(Ie)

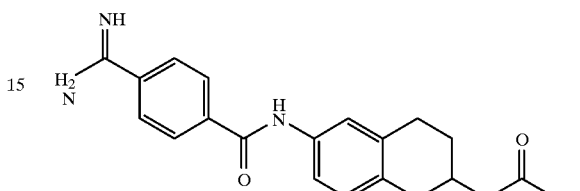
(If)

Suitable basic radicals include amino, imino, amidino, aminomethyleneamino, iminomethylamino, guanidino, aminoguanidino, alkylamino, dialkylamino, trialkylamino, alkylideneamino, pyranyl, pyrrolyl, imidazolyl, pyrazolyl, pyridyl, pyrazinyl, pyrimidinyl, pyridazinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, pteridinyl, 4aH-carbozolyl, carbozolyl, beta-carbolinyl, phenanthridinyl, acridinyl, pyrimidinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, or any of the preceding substituted with amino, imino, amidino, aminomethyleneamino, iminomethylamino guanidino, alkylamino, dialkylamino, trialkylamino, or alkylideneamino groups. Preferred basic radicals are selected from amino, piperidyl, guanidino, and amidine.

Basic group Q is an organic group containing at least one basic radical. A preferred Q group is represented by the formula;

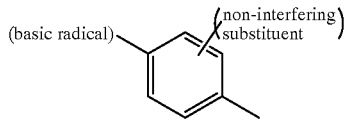

as, for example, the specific basic group;

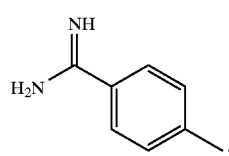

Another preferred basic group is represented by the formula:

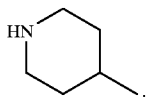

Preferred Formulae of Compounds of the Invention:

A preferred embodiment of the compound of the invention is represented by formula II, below:

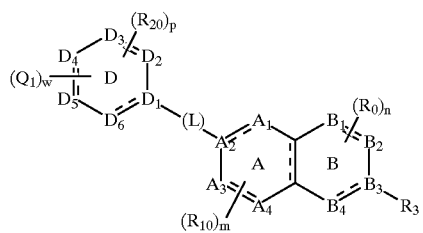

(II)

In formula II the basic group on atom $A_2$ of the nucleus has two parts, namely, (i) a six membered ring, D, which attaches to linking group —(L)—, and (ii) basic group(s), $Q_1$, (where w is an integer from 1 to 3) attached to the D ring.

Atoms; $D_1$, $D_2$, $D_3$, $D_4$, $D_5$ and $D_6$ are independently selected from carbon, nitrogen, oxygen, or sulfur; with the proviso that at least two of $D_1$, $D_2$, $D_3$, $D_4$, $D_5$ and $D_6$ are carbon. Preferred ring structures having pendant $Q_1$ are those where atoms $D_1$, $D_2$, $D_3$, $D_4$, $D_5$ and $D_6$ form a cyclic ring selected from the group consisting of benzene, pyridine, piperidine, 1,2-piperazine, 1,3-piperazine, 1,4-piperazine, pyran, thiopyran, thiabenzene, cyclohexene, and cyclohexane, with benzene being the most preferred.

Suitable basic groups $Q_1$ contain one or more nitrogen atoms and include amino, imino, amidino, aminomethyleneamino, iminomethylamino, guanidino, aminoguanidino, alkylamino, dialkylamino, trialkylamino, alkylideneamino, pyranyl, pyrrolyl, imidazolyl, pyrazolyl, pyridyl, pyrazinyl, pyrimidinyl, pyridazinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, pteridinyl, 4aH-carbazolyl, carbozolyl, beta-carbolinyl, phenanthridinyl, acridinyl, pyrimidinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, or any of the preceding substituted with amino, imino, amidino, aminomethyleneamino, iminomethylamino, guanidino, alkylamino, dialkylamino, trialkylamino, or alkylideneamino groups. Preferred nitrogen containing groups are selected from amino, piperidyl, guanidino, and amidino radicals. The most preferred basic group $Q_1$ is selected form an organic radical containing amidino functionality or the amidino group itself.

The substituents $R_{20}$ are the same or different on each atom $D_2$, $D_3$, $D_5$, and $D_6$ and the same or different between atoms $D_2$, $D_3$, $D_5$, and $D_6$ and are independently selected from hydrogen, alkyl, halosubstituted alkyl, alkenyl, alkynyl, cycloalkyl, aryl, arylalkyl, hydroxy, alkoxy, aralkoxy, amino, substituted amino, carbamyl, carboxy, acyl, cyano, halo, nitro, and sulfo. The number, p, of substituents $R_{20}$ is an integer from 0 to 8 depending on the sum of the number of unsatisfied bonds present in the individual atoms $D_2$, $D_3$, $D_5$, and $D_6$.

These preferred compounds of the invention contain one or more amino, guanidine, or amidine group(s), $Q_1$.

Preferred compounds of this invention are based on benzamidine substituted isoquinoline, isoquinolone, naphthalene, tetrahydronaphthalene, dihydronaphthalene, benzopyran, and tetralone nuclei, as partially illustrated in formulae (III) through (VII) below:

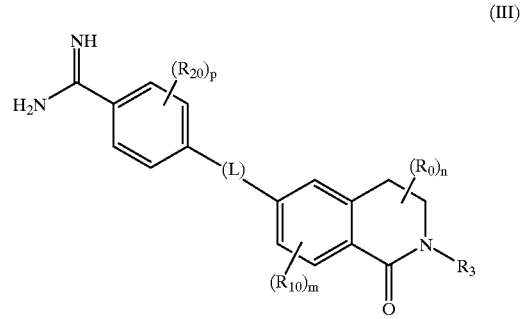

(III)

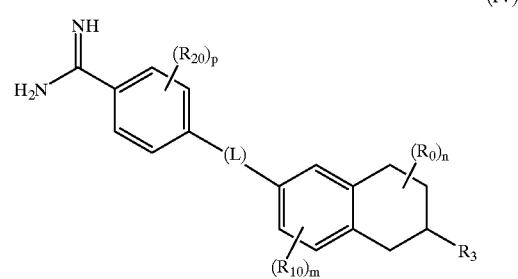

(IV)

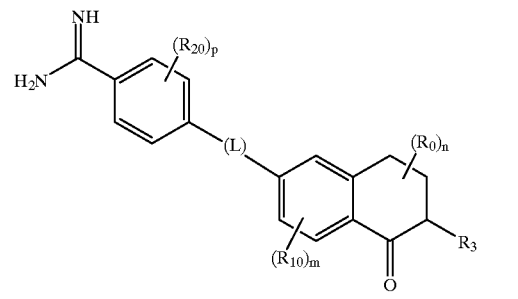

(V)

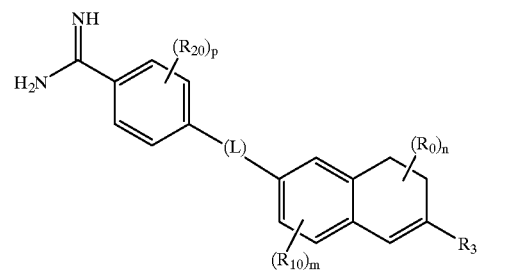

(VI)

-continued

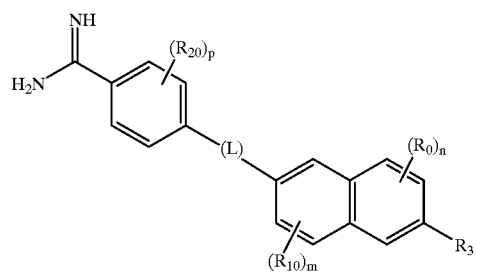

(VII)

where —(L)—, n, m, p, $R_0$, $R_3$, $R_{10}$ and $R_{20}$ are as previously defined. Most preferred are compounds where $R_{10}$ and $R_{20}$ are hydrogen and —(L)— has 2 carbon atoms.

Specific compounds of the invention of the isoquinoline type which are highly preferred are represented by the following structural formulae X to XXXIa or a pharmaceutically acceptable salt, solvate or prodrug derivative thereof:

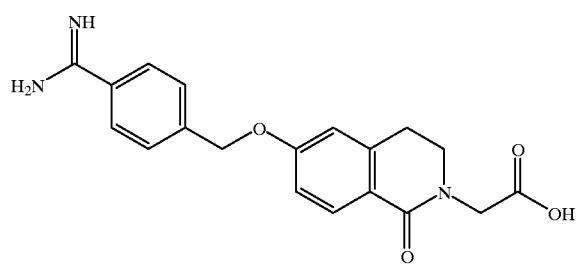

(X)

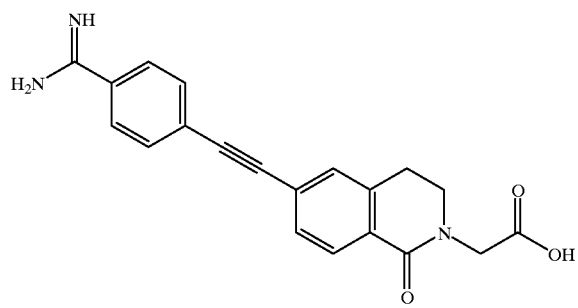

(XI)

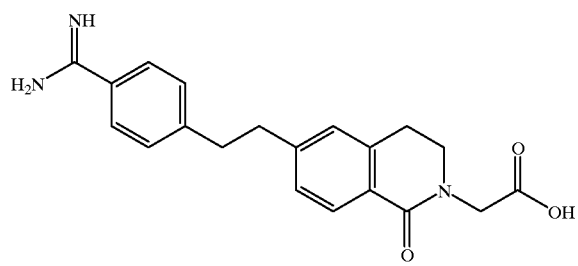

(XII)

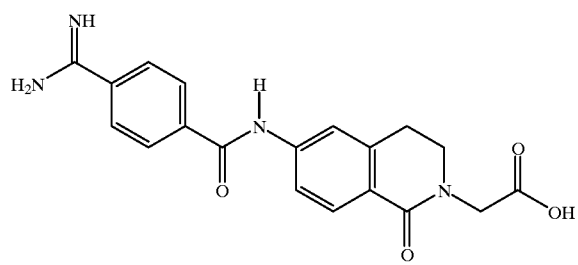

(XIII)

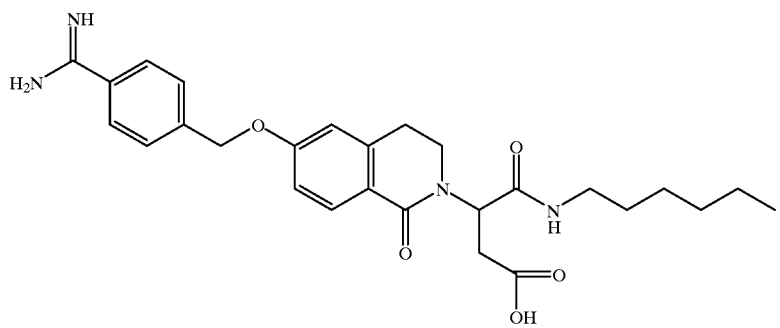
(XIV)
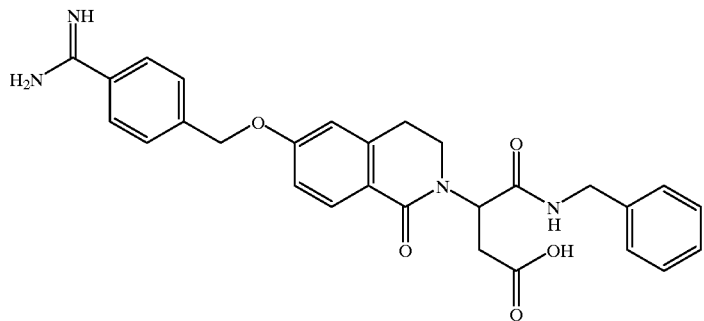
(XV)
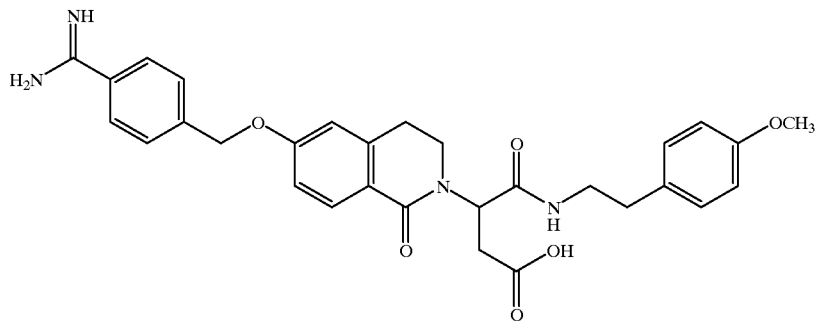
(XVI)
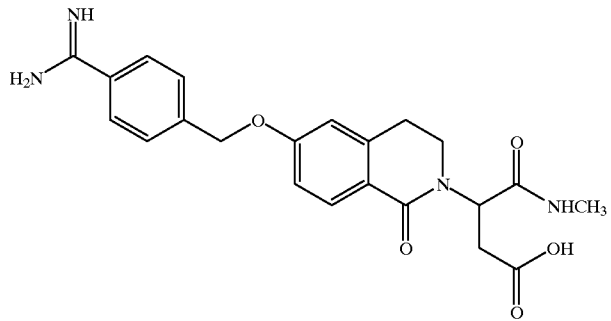
(XVII)

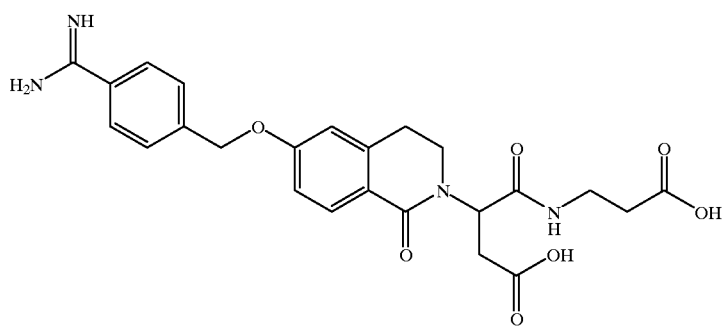
(XVIII)
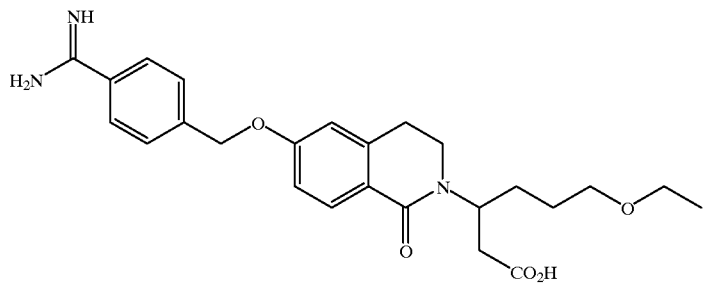
(XIX)
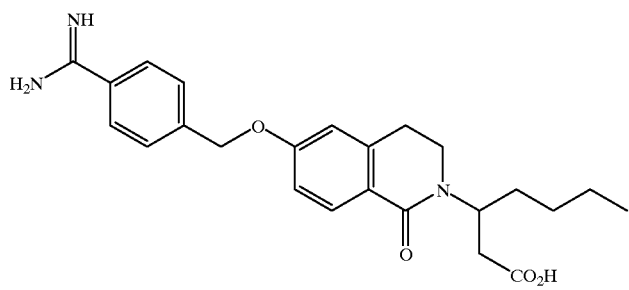
(XX)
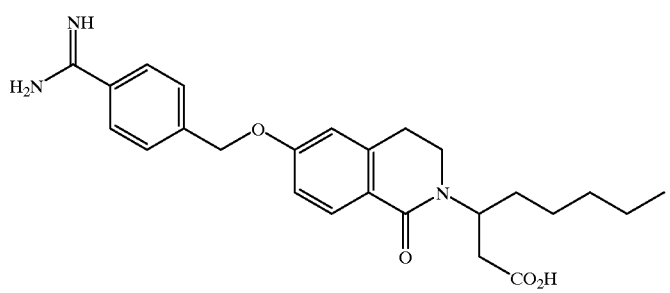
(XXI)
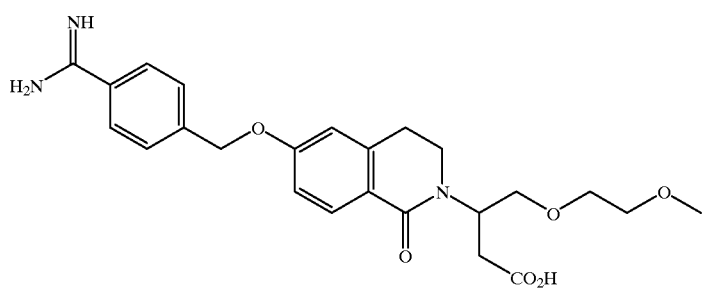
(XXII)

(XXIII)
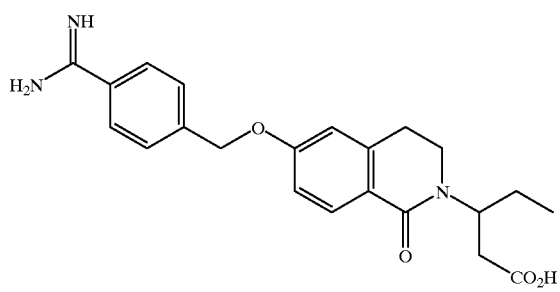
(XXIV)
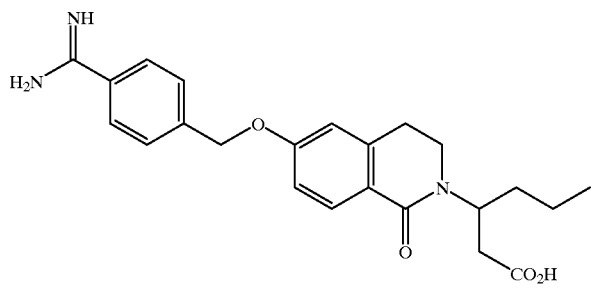
(XXIX)
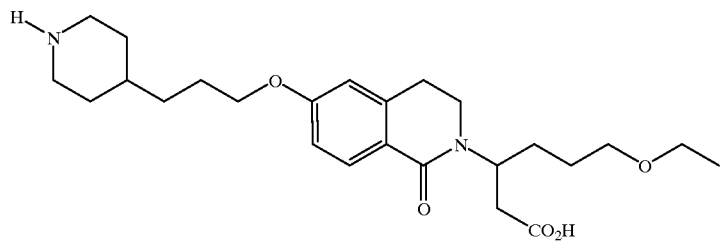
(XXX)
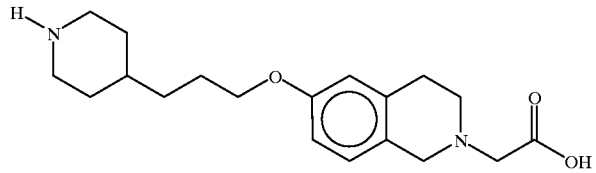
(XXXI)
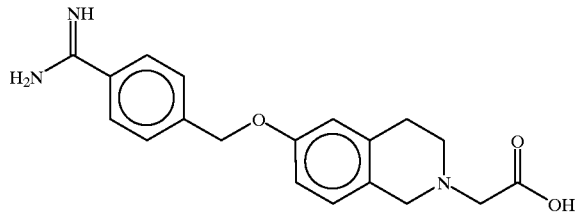
(XXXIa)
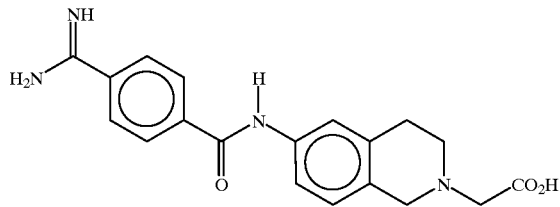
and mixtures of compounds (X) to (XXXIa).
Other specific compounds of the invention of the naphthalene/tetralin-type which are highly preferred are represented by the following structural formulae XXXII to XLIX or a pharmaceutically acceptable salt, solvate or prodrug derivatives thereof:

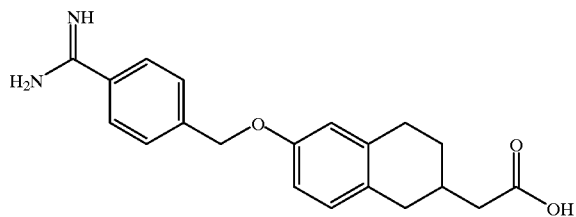
(XXXII)
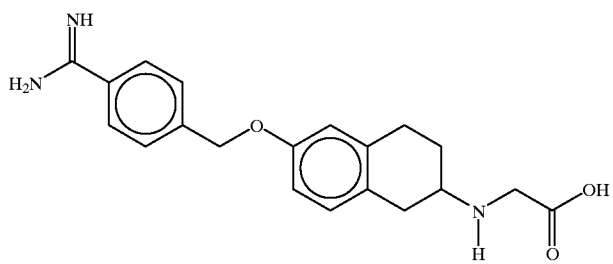
(XXXIII)
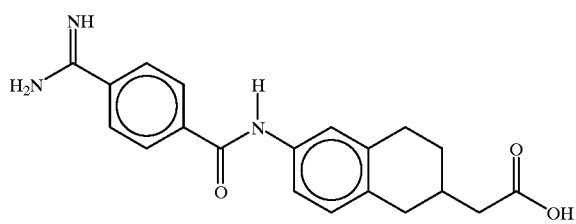
(XXXIV)
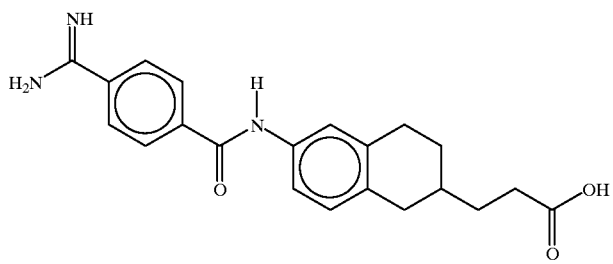
(XXXV)
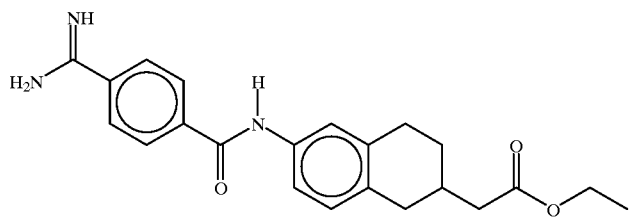
(XXXVI)
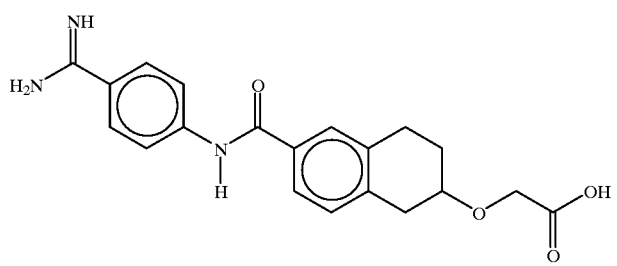
(XXXVII)

-continued
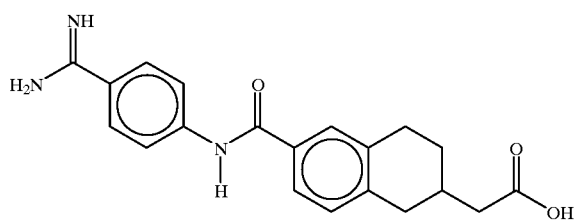
(XXXVIII)
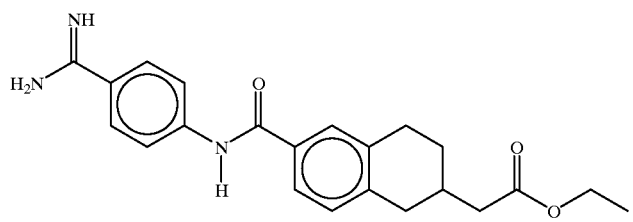
(XXXIX)
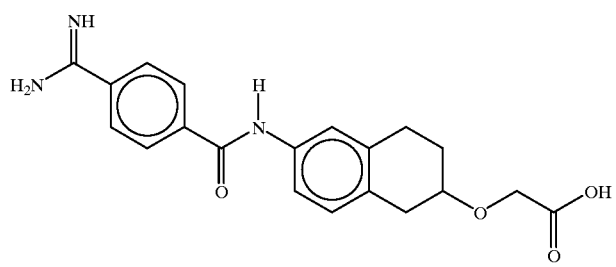
(XL)
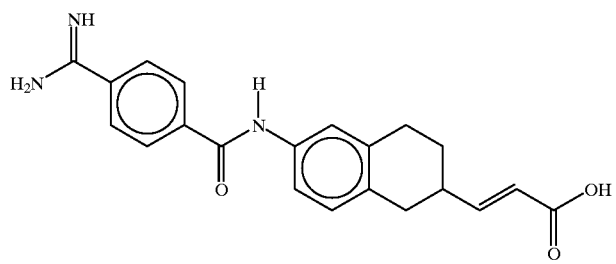
(XLI)
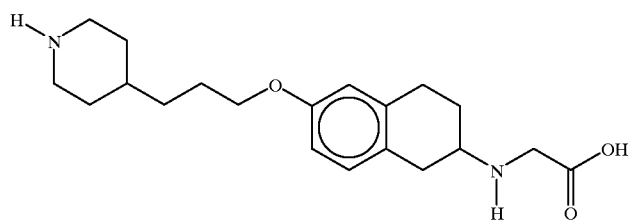
(XLII)
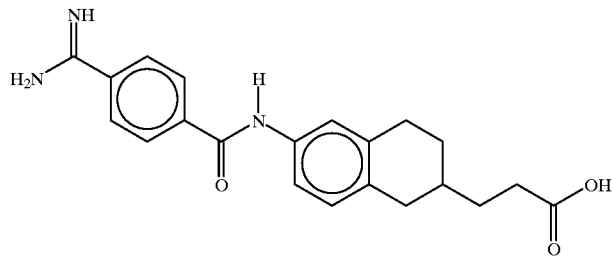
(XLIII)

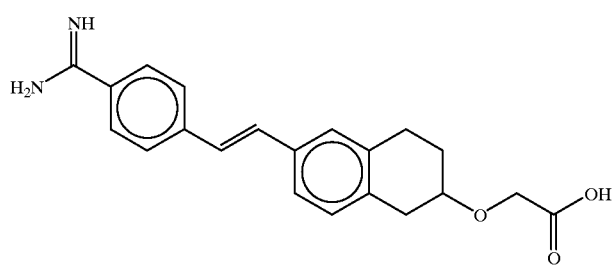
(XLIV)
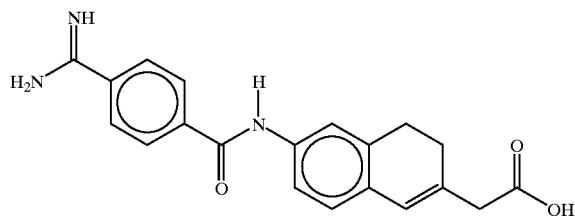
(XLV)
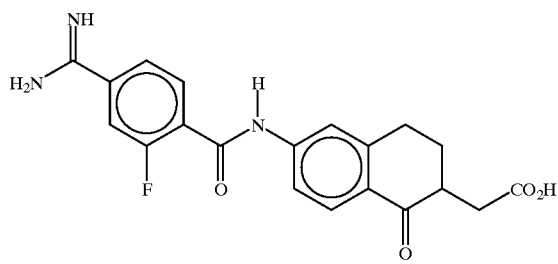
(XLVI)
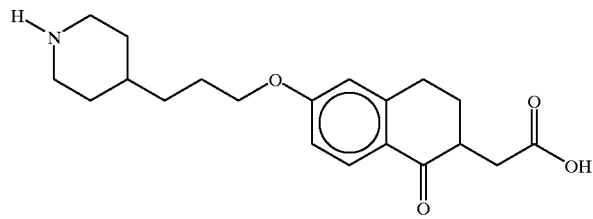
(XLVII)
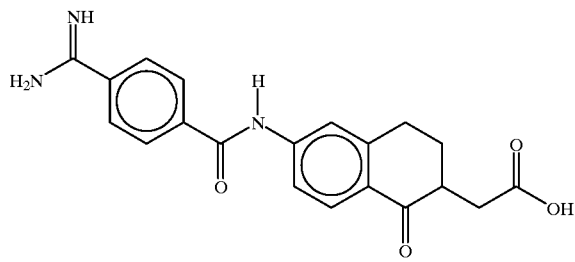
(XLVIII)
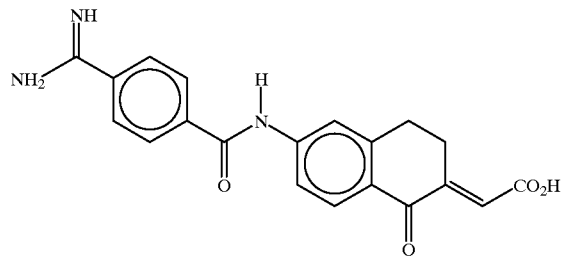
(XLIX)
and mixtures of compounds (XXXII) through (XLIX).

Other preferred specific compounds of the invention are represented by the following structural formulae L to LXIII and all pharmaceutically acceptable salts, solvates and pro-drug derivatives thereof:
(L)
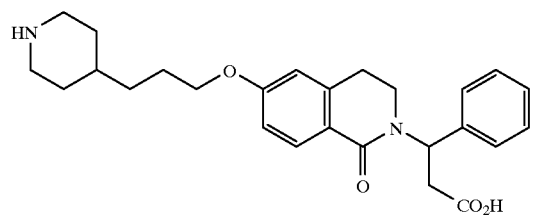
(LI)
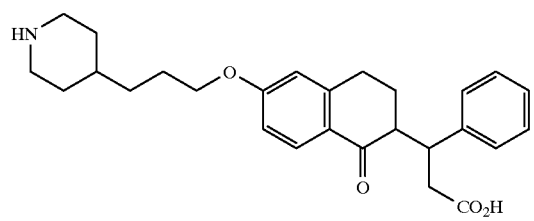
(LII)
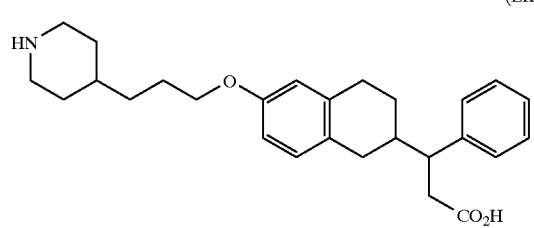
(LIII)
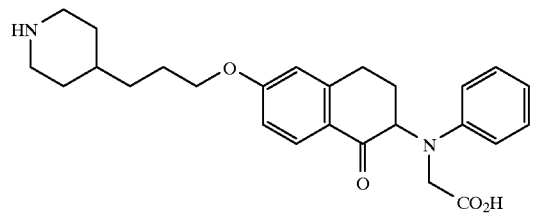
(LIV)
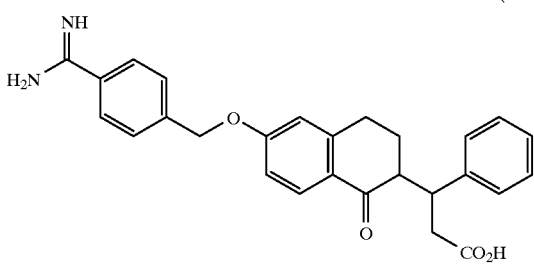
(LV)
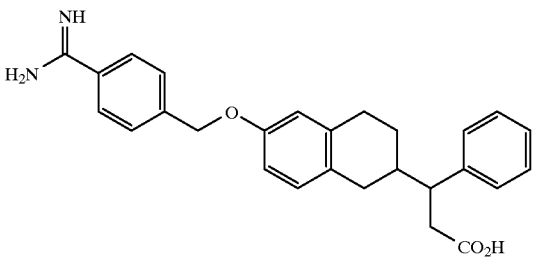
(LVI)
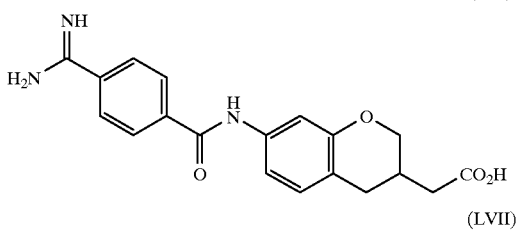
(LVII)
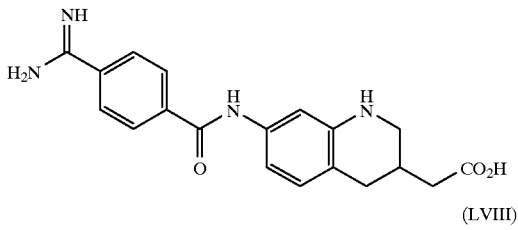
(LVIII)
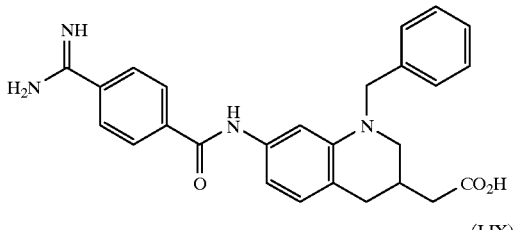
(LIX)
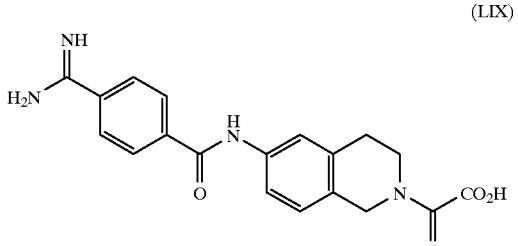
(LX)
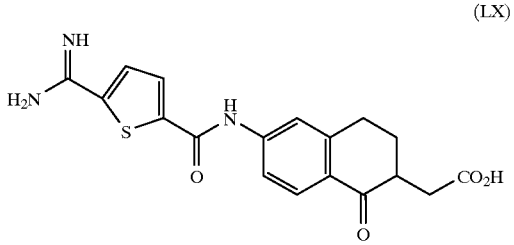

-continued

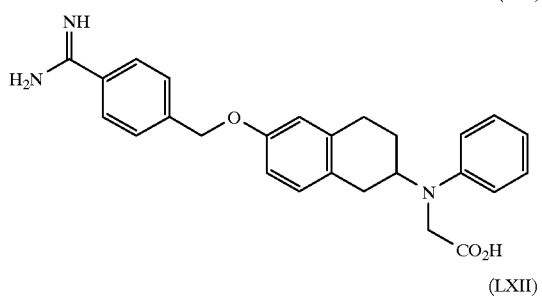
(LXI)

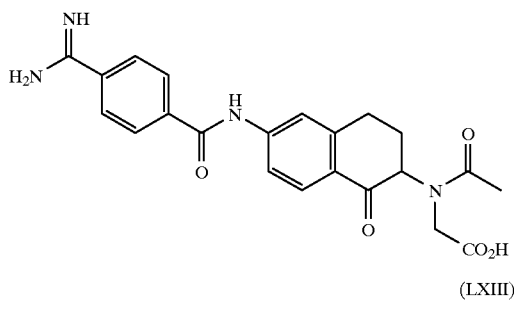
(LXII)

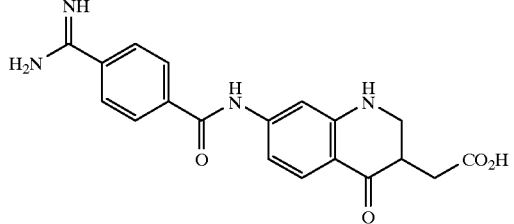
(LXIII)

and mixtures of any of (L) to (LXIII).

The compounds of the invention possess at least one acidic functional substituent (viz., $R_3$ of Formula I) and, as such, are capable of forming salts. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an anion exchange resin on the salt cycle.

Included within the definition of pharmaceutically acceptable salts are the relatively non-toxic, inorganic and organic base addition salts of compounds of the present invention, for example, ammonium, quaternary ammonium, and amine actions, derived from nitrogenous bases of sufficient basicity to form salts with the compounds of this invention (see, for example, S. M. Berge, et. al., "Pharmaceutical Salts," J. Phar. Sci., 66: 1–19 (1977)).

The basic portion of the compounds of the invention (viz., group Q of formula I and group $Q_1$ of formula II) may be reacted with suitable organic or inorganic acids to form salts of the invention. Representative salts include those selected from the group comprising:

Acetate
Benzenesulfonate
Benzoate
Bicarbonate
Bisulfate
Bitartrate
Borate
Bromide
Camsylate
Carbonate
Chloride
Clavulanate
Citrate
Dihydrochloride
Edetate
Edisylate
Estolate
Esylate
Fumarate
Gluceptate
Gluconate
Glutamate
Glycollylarsanllate
Hexylresorcinate
Hydrabamine
Hydrobromide
Hydrochloride
Hydroxynaphthoate
Iodide
Isothionate
Lactate
Lactobionate
Laurate
Malate
Malseate
Mandelate
Mesylate
Methylbromide
Methylnitrate
Methylsulfate
Mucate
Napsylate
Nitrate
Oleate
Oxalate
Palmitate
Pantothenate
Phosphate
Polygalacturonate
Salicylate
Stearate
Subacetate
Succinate
Tannate
Tartrate
Tosylate
Trifluoroacetate
Trifluoromethane sulfonate
Valerate The compounds of the formula (I) can also be in the form of zwitterions, since they contain both acidic and basic functionality and are capable of self-protonation.

Certain compounds of the invention possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrugs are derivatives of the compounds of the invention which have metabolically cleavable groups and become by solvolysis or under physiological conditions the compounds of the invention which are pharmaceutically active in vivo. For example, ester derivatives of compounds of this invention are often active in vivo, but not in vitro. Other derivatives of the compounds of this invention have activity in both their acid and acid derivative forms, but the acid derivative form often offers advantages of solubility, tissue compatibility, or delayed release in the mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with an amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters.

Particularly preferred are the ethyl esters of the compounds of the invention (per formula I), as for example, the compounds represented by the formulae XXXVIA and XLVIIIa shown below:

Method of Making Compounds of the Invention

General synthesis schemes 1 through 8 shown below are used to prepare the compounds of the invention.

The following abbreviations are used throughout the synthesis Schemes and Examples:

| | |
|---|---|
| TBAF | tetra-butyl ammonium fluoride |
| Tf | (triflate) - trifluoromethane sulfonate |
| Boc | tertiary-butoxy carbonyl |
| Bn | benzyl |
| Bu$^t$ | tertiary butyl |
| DMF | dimethyl formamide |
| TFA | trifluoroacetic acid |
| Cbz | benzyloxycarbonyl |
| EDCI | 1-(3-dimethylaminopropyl)-3-ethyl carbodiimide |
| DMAP | dimethylaminopyridine |
| LHMDS | lithium hexamethyl disilazane |
| THF | tetrahydrofuran |
| DIBAH | diisobutyl aluminum hydride |
| Boc$_2$O | di-tert-butyl dicarbonate |
| HMDS | hexamethyl disilazane |
| TSOH | p-toluene sulfonic acid |
| MCPBA | meta-chloro-peroxy benzoic acid |
| NMO | 4-methylmorphoilne-N-oxide |
| TFAA | Trifluoroacetic anhydride |
| TBSCL | tert-butyl dimethyl silyl chloride |

General Comments:

The reactions described in reaction schemes 1, 2, 3, 4, 5, 6, 7, and 8 are carried out using standard chemical methodologies described and referenced in standard textbooks. Starting materials are commercially available reagents and reactions are carried out in standard laboratory glassware under reaction conditions of standard temperature and pressure, except where otherwise indicated.

(XXXVIa)

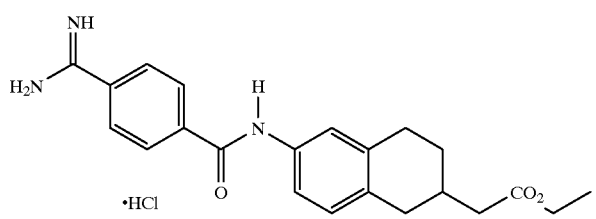

and (XLVIIIa)

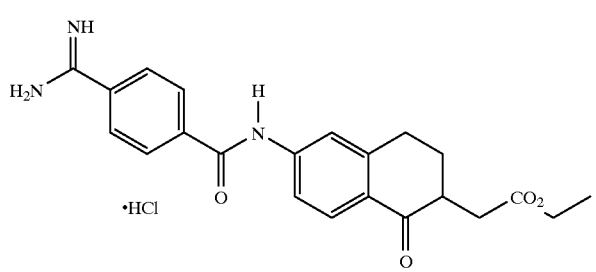

Scheme 1

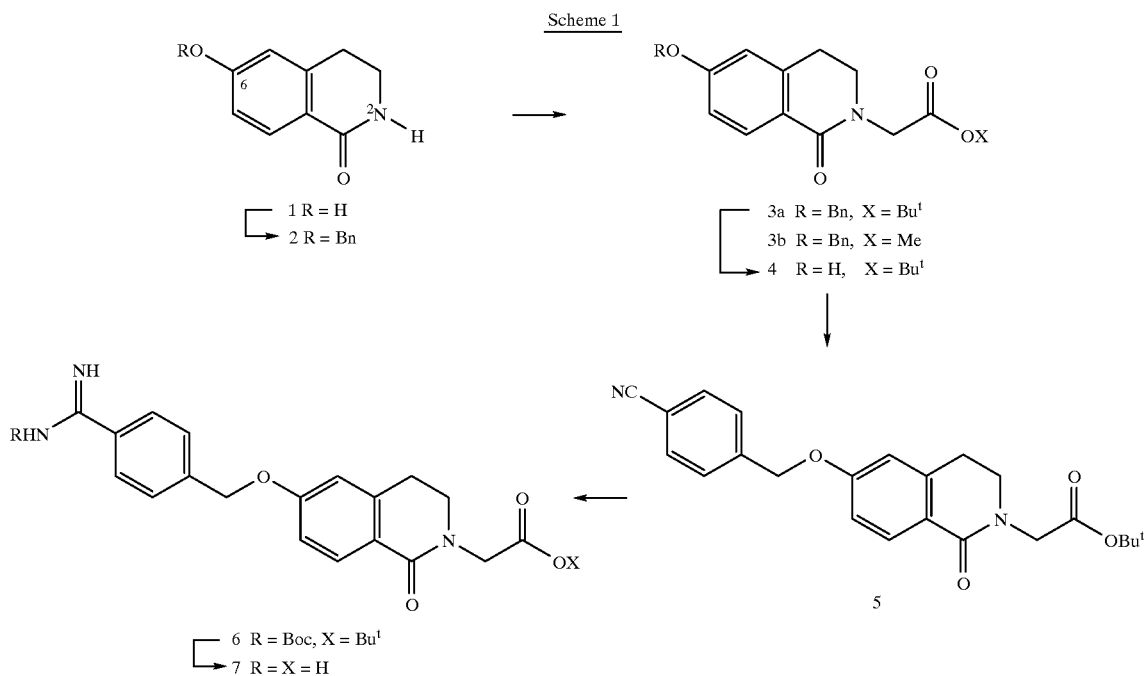

Scheme 1 teaches a method of preparing 2,6-disubstituted isoquinolones having an ether linked arginine isostere at $C_6$ and an acetic acid residue at position 2. In the first step of Scheme 1, isoquinoline (1) reacts with benzyl bromide in the presence of potassium carbonate in refluxing acetone to give a benzyl protected phenol (2). This compound reacts with sodium hydride and is then alkylated on nitrogen with either alpha-bromo tert-butyl acetate or alpha-bromo methyl acetate to give a 2-substituted isoquinolone (3a) (6-benzyloxy-3,4-dihydro-1-oxo-2(1H)isoquinolone acetic acid-1,-dimethylethyl ester) or (3b). The $C_6$ benzyl group is subsequently removed with hydrogen and palladium and subsequent alkylation of the 6-hydroxy group is accomplished with $K_2CO_3$ and alkyl bromide to give the di-substituted isoquinolone (5). Compound (5) is then transformed into the Boc protected amidine (6) using a series of reactions, namely; (i) reacting the nitrile with $H_2S$, (ii) alkylating the intermediate thioamide with methyl iodide, (iii) reacting the intermediate thioimidate with ammonium acetate, and (iv) thereafter Boc protecting the formed amidine to give compound (6). Compound (6) is deprotected with neat TFA giving (7) as the TFA salt.

Scheme 2

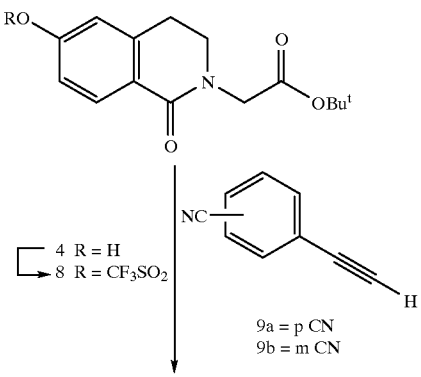

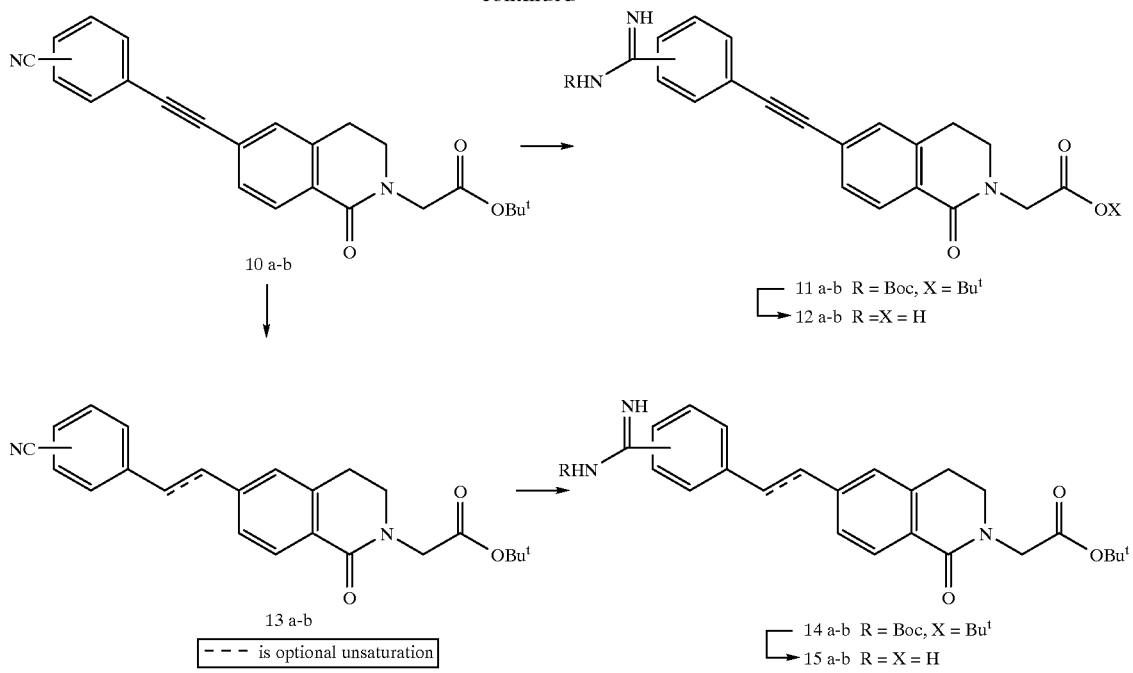

Scheme 2 describes a synthesis method suitable to give carbon substitution at position $C_6$ of the bicyclic nucleus. In this scheme compound (4) (6-hydroxy-3,4-dihydro-1-oxo-2 (1H) isoquinolone acetic acid-1,1-dimethylethyl ester) from Scheme 1 is transformed into the triflate (8) using triflic anhydride and pyridine. The compound is thereafter reacted with the acetylenic compound (9a) or (9b) in the presence of palladium to give acetylene linked benzonitrile (10a) or (10b). Compound (10a) or (10b) is transformed again with the same set of procedures used to transform compound (5) (6-[(4 cyanophenyl) methoxy]-3,4-dihydro-1-oxo-2(1H) isoquinolone acetic acid, -1,1-dimethyl ethyl ester) to compound (6) (6-[[4-(1,1-dimethylethoxycarbonyl minoiminomethyl)phenyl]methoxy]-3,4-dihydro-1-oxo-2 (1H)isoquinolone acetic acid-1,1-dimethyl ethyl ester) to yield the amidine product (11a) or (11b). Compounds (11a) or (11b) may also be deprotected again with TFA to give compound (12a) or (12b). Alternatively, intermediate (10a) or (10b) can be either partially or fully hydrogenated as shown in the scheme giving the alkylene or alkenylene linked compound (13a) or (13b). Compound (13a) or (13b) is again transformed using the nitrile to amidine conversion previously described (Scheme 1, steps 5>6), giving compound (14a) or (14b) which is subsequently deprotected with TFA to give compound (15a) or (15b).

Scheme 3

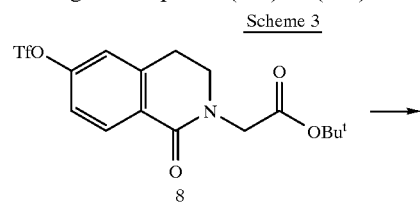

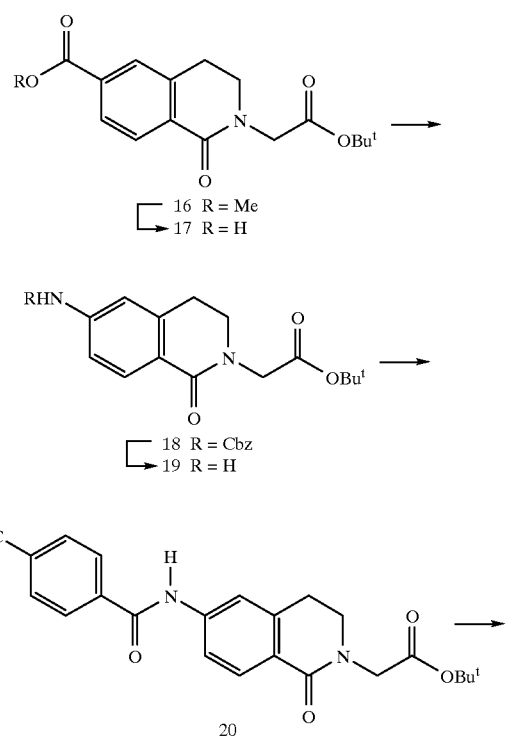

-continued

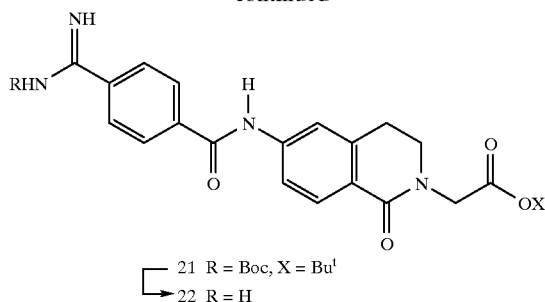

21 R = Boc, X = Bu$^t$
22 R = H

Scheme 3 describes the preparation of isoquinolones containing nitrogen substitution at $C_6$. This scheme starts with triflate (8) whose preparation was previously described in Scheme 2. The triflate is transformed to aryl ester (16) via the use of palladium, carbon monoxide and methanol. The ester (16) is then saponified with lithium hydroxide in aqueous THF. The free acid (7) is then subjected to a Curtius rearrangement (viz., formation of an isocyanate by thermal decomposition of acyl azides). The required acyl azide is formed with a triphenyl phosphoryl azide and then pyrolized in situ to give an isocyanate which is then trapped with benzyl alcohol giving Cbz protected aniline (18). Aniline (18) is then transformed into free amine (19) with catalytic hydrogenation. Amine (19) is then acylated with paracyanobenzoic acid in the presence of EDCI and DMAP giving the amide-linked compound (20). Compound (20) is then transformed into the Boc protected amidine (21) again using the conditions of Scheme 1 and that compound is then deprotected with TFA to give compound (22).

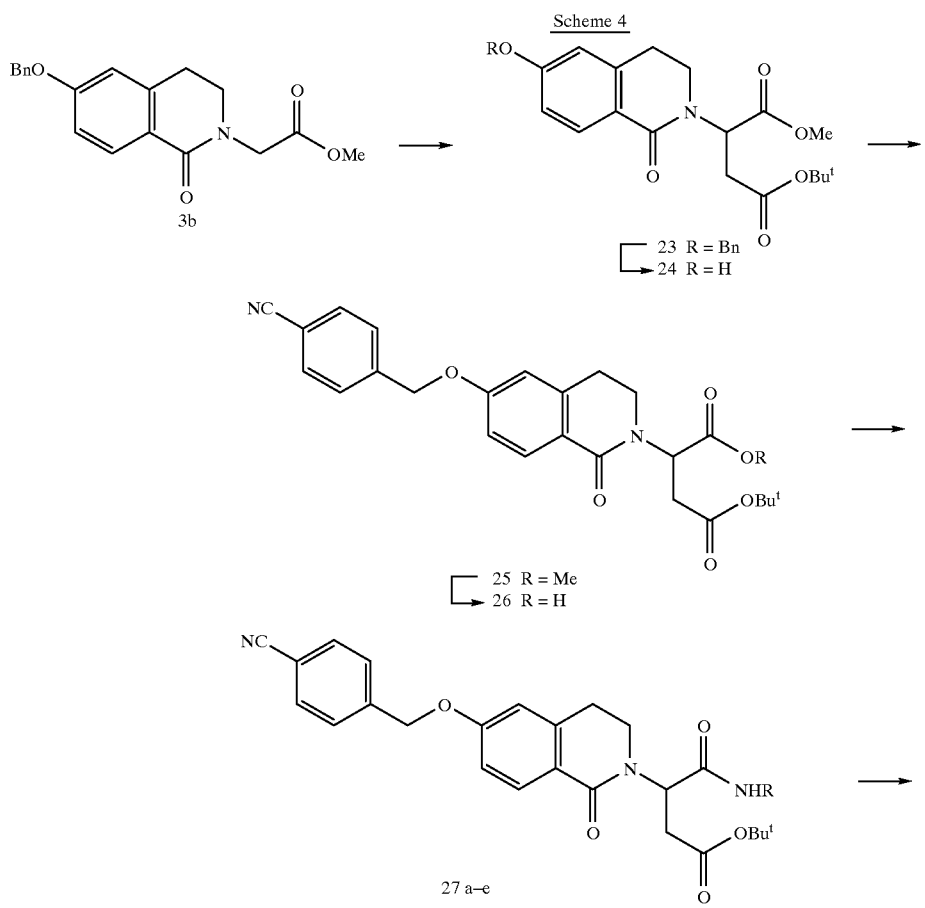

Scheme 4

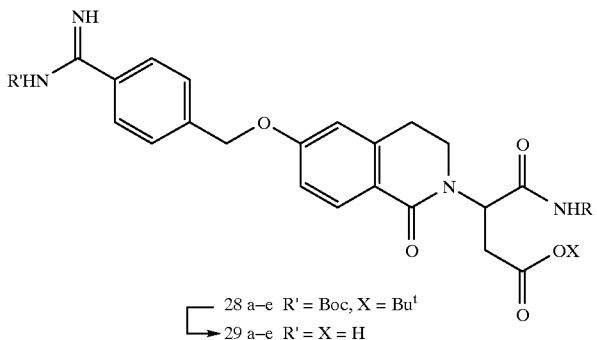

- 28 a–e  R' = Boc, X = Bu$^t$
- 29 a–e  R' = X = H

Amines (a) to (e):

(a) - hexyl amine
(b) - benzyl amine
(c) - p-methoxy phenethyl amine
(d) - methyl amine
(e) - beta-amino-t-butylalanine Scheme 4 describes how to make 2,6-disubstituted isoquinilones in which the 2-position is substituted with an aspartic acid moiety. Scheme 4 starts with compound (3b) whose preparation is described in Scheme 1. Compound (3b) is deprotenated with LHMDS and the resulting anion is quenched with alpha-bromo-t-butyl acetate to give compound (23). The 6-benzyl group of compound (23) is removed with palladium and hydrogen to give the free phenol (24). Compound (24) is then alkylated as described for the preparation of compound (5) in Scheme 1. The methyl ester (25) is then saponified with lithium hydroxide in THF to give the free carboxylate (26). The free carboxylate is then coupled with a variety of amines in the presence of EDCI and DMAP to give the half amide esters (27a) thru (27e). The half amide esters (27a) thru (27e) are then transformed again using the same protocol as previously described in Scheme 1 (steps 5–6)to give a Boc protected amidines (28a) thru (28e). The Boc protected amidine is then deprotected with TFA to give compounds (29a) thru (29e).

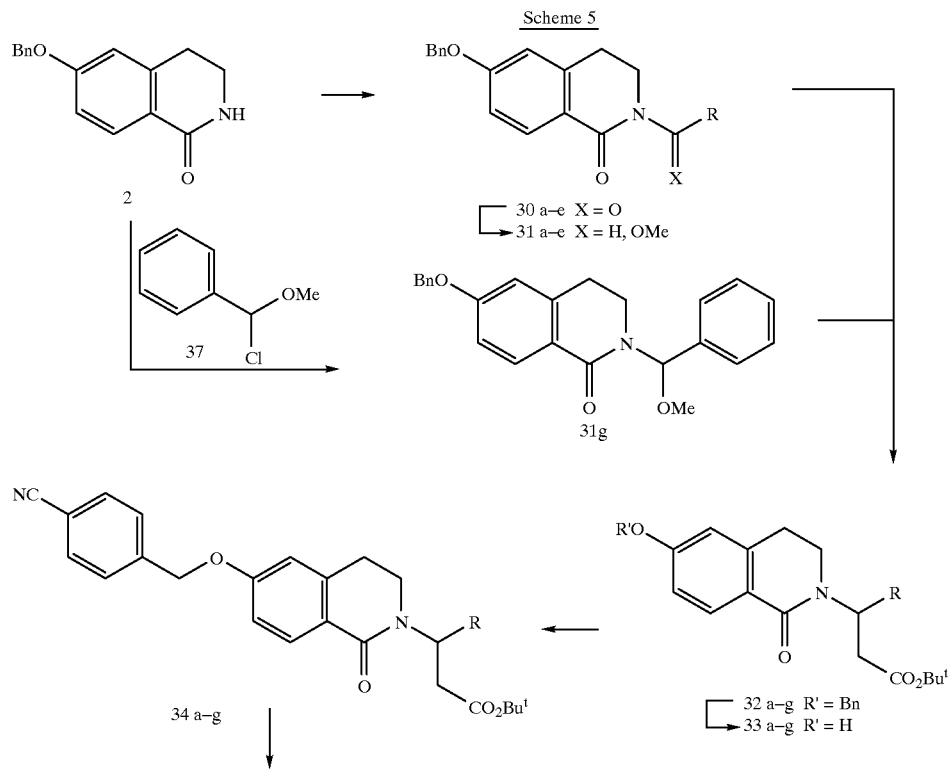

Scheme 5

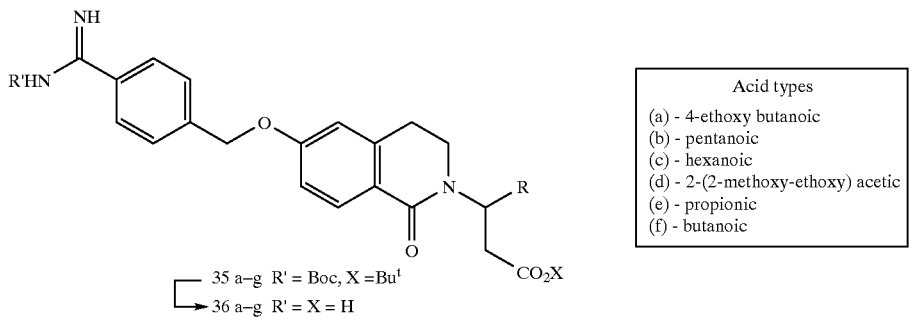

35 a–g  R' = Boc, X = Bu$^t$
36 a–g  R' = X = H

Acid types
(a) - 4-ethoxy butanoic
(b) - pentanoic
(c) - hexanoic
(d) - 2-(2-methoxy-ethoxy) acetic
(e) - propionic
(f) - butanoic Scheme 5 describes the preparation of 2,6-di-substituted isoquinilones n which the 2-position is substituted by an aspartate isostere. Scheme 5 compounds differ from the compounds prepared in Scheme 4 in that the R group of the Scheme 5 compound (36) does not contain an amide linkage like the Scheme 4 compounds (29a) thru (29e). Compound (2), the starting material, is prepared by the method of Scheme 1, then acylated with a variety of activated acids (acid halides or anhydrides) to give the corresponding imides (30a) thru (30e). Thereafter the imide is selectively reduced at its exocyclic carbonyl with DIBAH and then entrapped with acidic methanol to give alpha-methoxy amides (31a) thru (31e). Alternatively, alpha-methoxy amides (31) can be prepared by reacting the sodium salt of (2) with an appropriate alpha chloro ether (37). All of the alpha-methoxy amides (31a) thru (31g) are reacted with boron trifluoride etherate in the presence of a ketene acetal to give the beta,beta-di-substituted propionates (32a) through (32g). Thereafter, the benzyl group is removed from the 6 position by catalytic hydrogenation and phenols can be alkylated again in the same manner as shown in Scheme 1 (steps 4>5) to give the ether linked nitriles (34a) to (34g). That nitrile can then be converted to the Boc protected amidine (35a) to (35g) as shown in Scheme 1 (steps 5>6), Thereafter, deprotection gives the final compounds (36a) to (36g).

Scheme 6

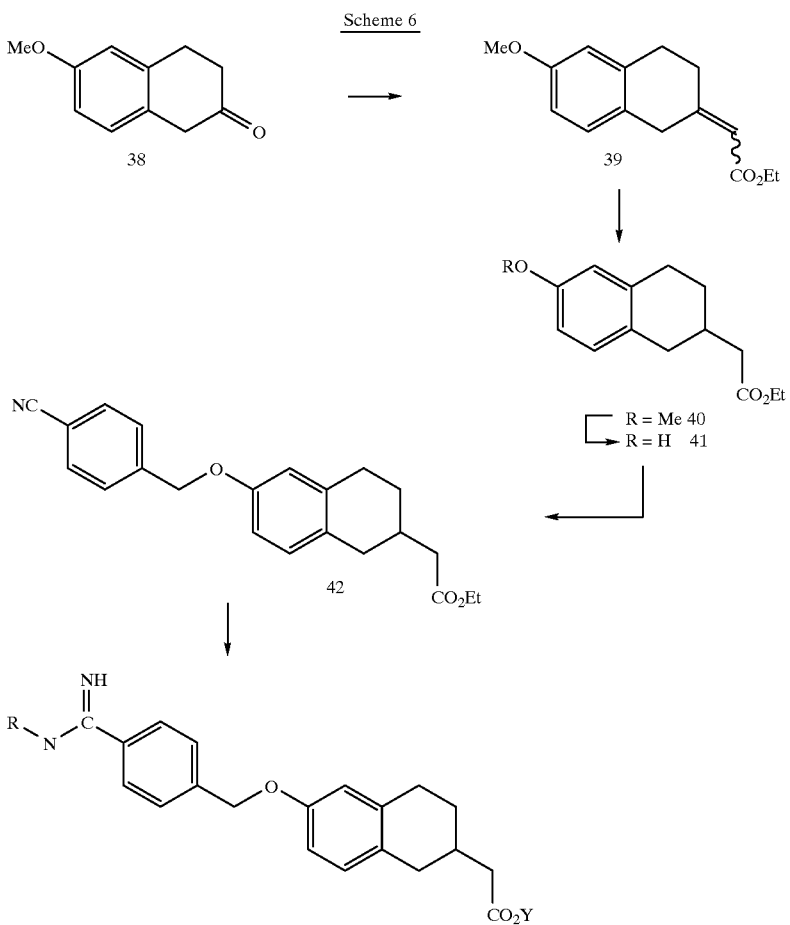

| R = Bu$^t$ | Y = Et | 43 |
| R = Bu$^t$ | Y = H  | 44 |
| R = H      | Y = H  | 45 |

Scheme 6 describes the preparation of compounds of the invention having a tetralin nucleus. 6-methoxy-2-tetralone (38) is reacted with tert-butyl diethylphosphono acetate to give unsaturated ester (39). Subsequent hydrogenation removes the unsaturation to give compound (40). Compound (40) is treated with boron tribromide and the crude product is reesterified with HCl and ethanol to give (41). The phenol (41) is then alkylated in the same manner as shown in Scheme 1 (step 4–5) giving (42). The nitrile can then be converted to the Boc protected amidine (43) as shown in Scheme 1 (step 5–6). The amidino ester (43) is then saponified with sodium hydroxide to give compound (44), which then is later deprotected with TFA and anisole to give the final product (45).

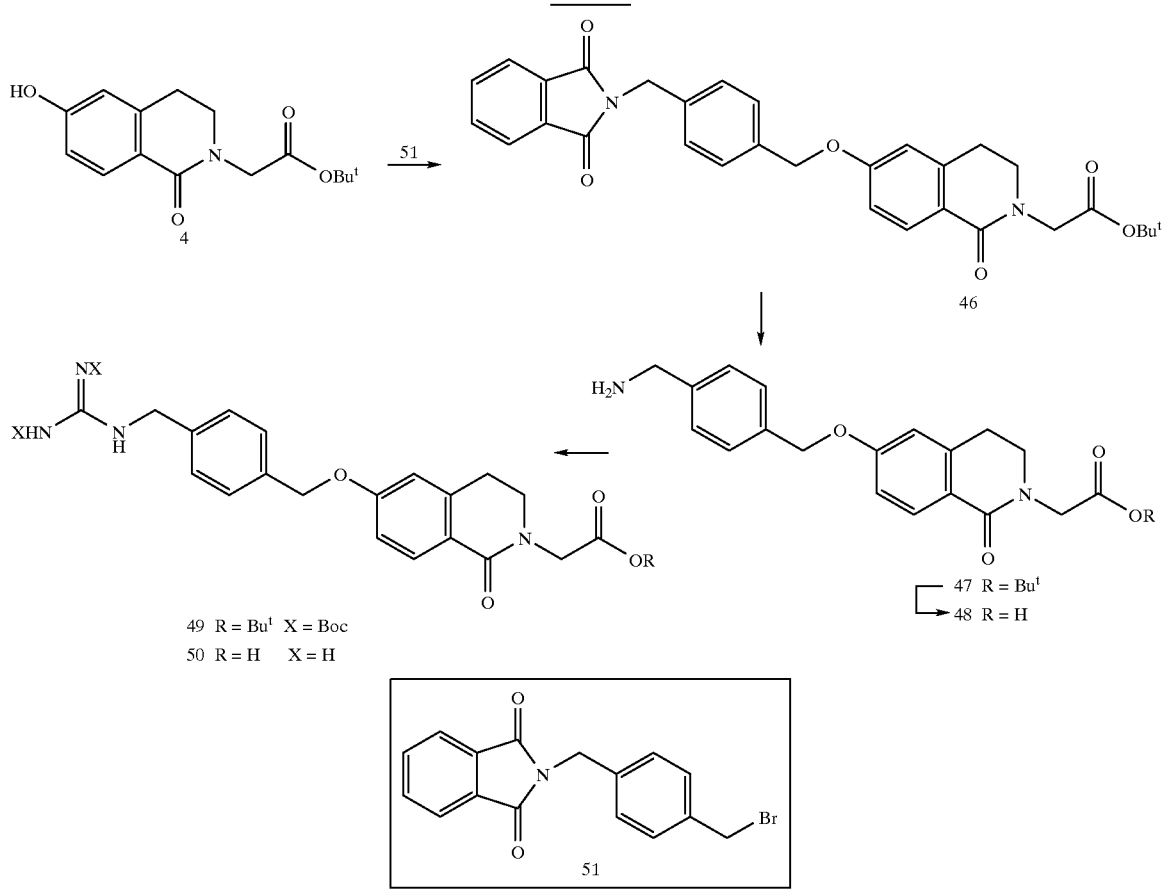

Scheme 7 describes the preparation of compounds of the invention having a guanidine group as the basic functionality. Phenol (4), prepared in scheme 1, is alkylated with bromide (51) (prepared from the dibromide and potassium pthalimide) giving adduct (46). This compound is deprotected with aqueous hydrazine giving amine (47). Compound (47) is transformed into protected guanidine (49) with N,N'-bis(tert-butoxy carbonyl)-S-methyl-isothiourea. Compound (49) is deprotected with TFA giving product (50) as the trifluoroacetate salt.

Scheme 8

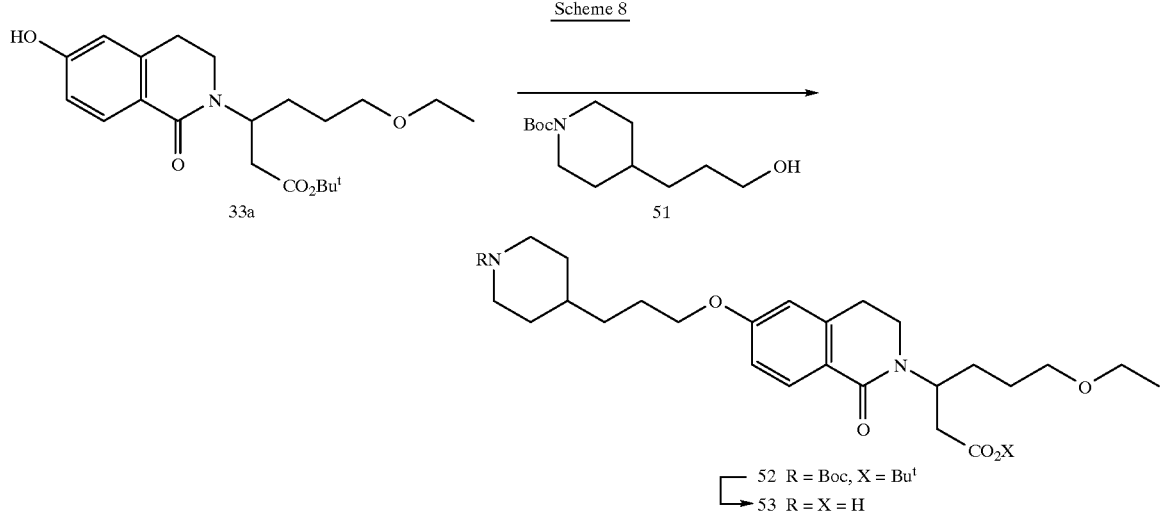

Scheme 8 describes the preparation of compounds of the invention having an amine group as the basic functionality.

Compound (33a), prepared in scheme 5, is coupled with alcohol (51) (prepared from 3-(4-pyridyl)-propanol using standard protocols) using triphenyl phosphene and diethyl azodicarboxylate giving compound (52). Compound (52) is deprotected with neat TFA giving product (53) as the TFA salt.

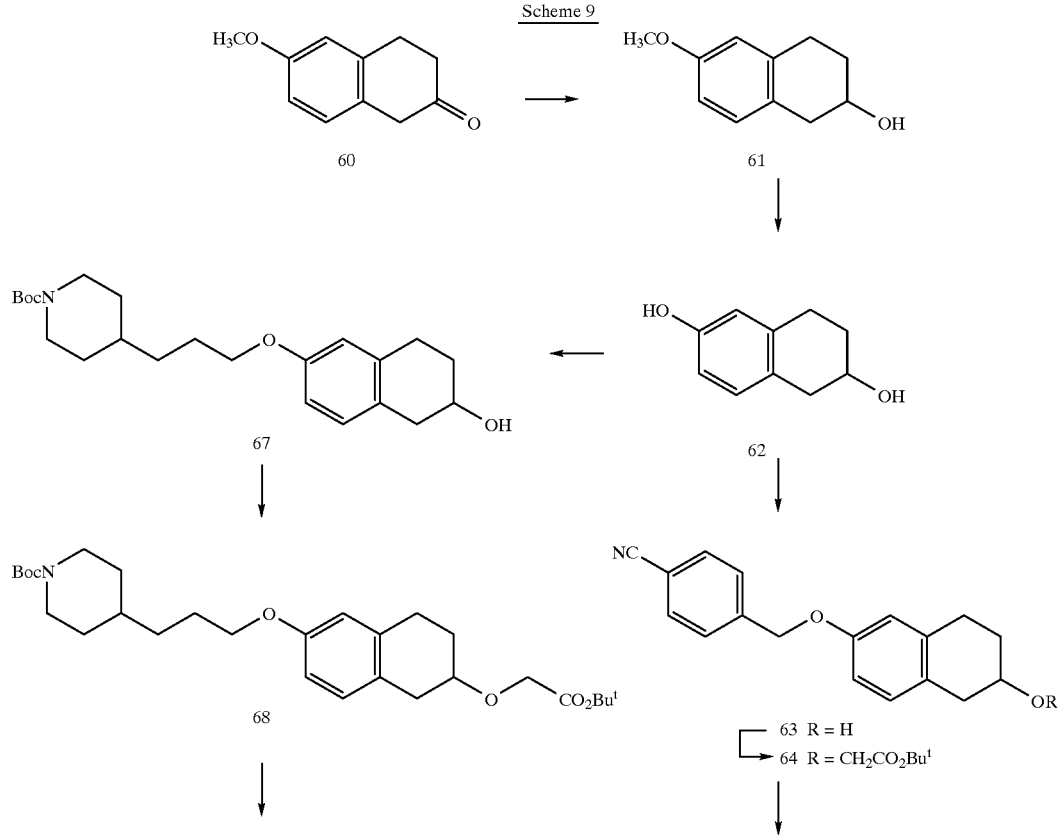

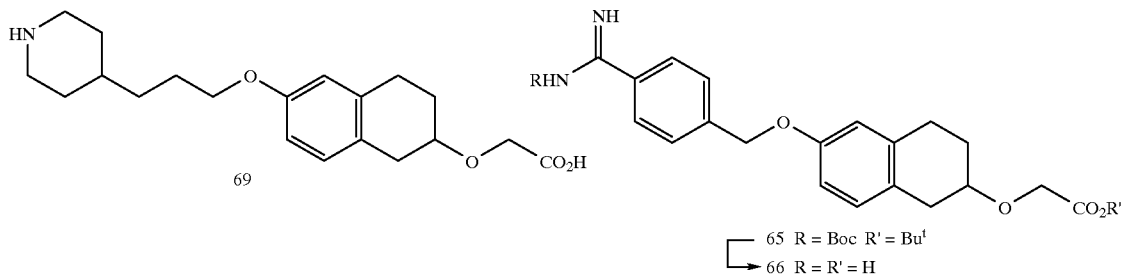

65 R = Boc R' = Bu$^t$
66 R = R' = H

Scheme 9 describes the preparation of 2–6 disubstituted tetralins in which the 2 position is occupied by an α-alkoxyacetic acid residue and the 6 position retains either an ether linked benzamidine or an ether linked 4-alkylpiperidine moiety. The scheme begins with 6-methoxy-2-tetralone (60) which is sequentially treated with NaBH$_4$ and then with DIBAH giving dihydoxy compound 62. The phenolic hydroxyl can be selectively alkylated with either α-bromo-p-tolunitrile or the appropriate 4-alkylpiperidine giving compounds 63 and 67 respectively. Both compounds are then alkylated with tert-butyl bromoacetate under phase transfer conditions providing 64 and 68. Nitrile 64 is converted to the Boc protected amidine 65 and then to product 66 using the same sequence of reactions described in Scheme 1. Compound 68 is converted to the fully deprotected 69 by treatment with TFA.

Scheme 10

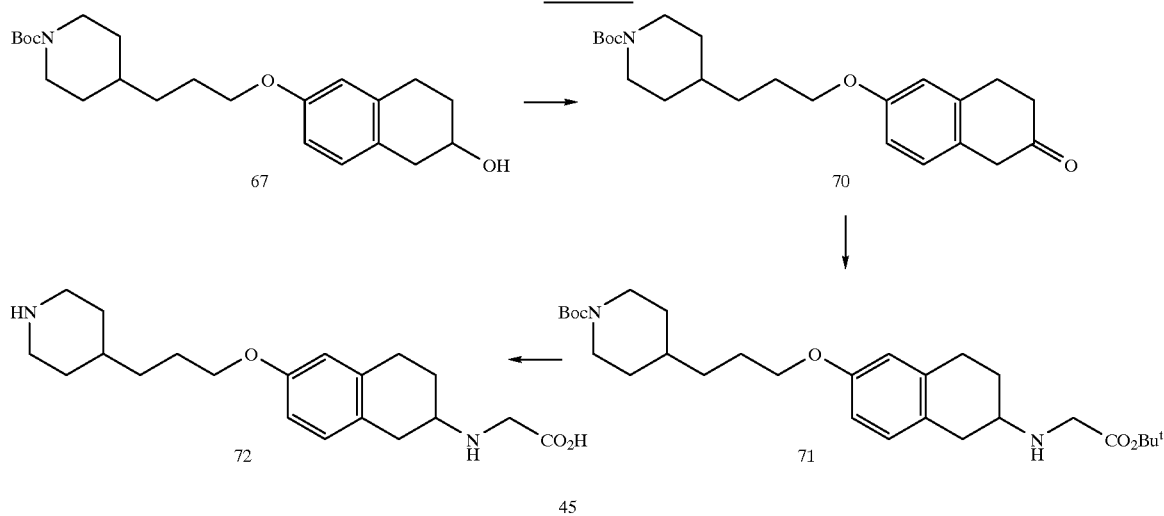

Scheme 10 outlines the preparation of 2,6-disubstituted tetralins in which an α-aminoacetic acid moiety resides at position 2 and an ether linked 4-alkylpiperidiene emanates from position 6. Alcohol 67, prepared in Scheme 9, is oxidized with DMSO and TFAA using the conditions of Swern giving ketone 70 which is reductively aminated with glycine tert-butyl ester giving 71. This material is then deprotected with TFA giving 72.

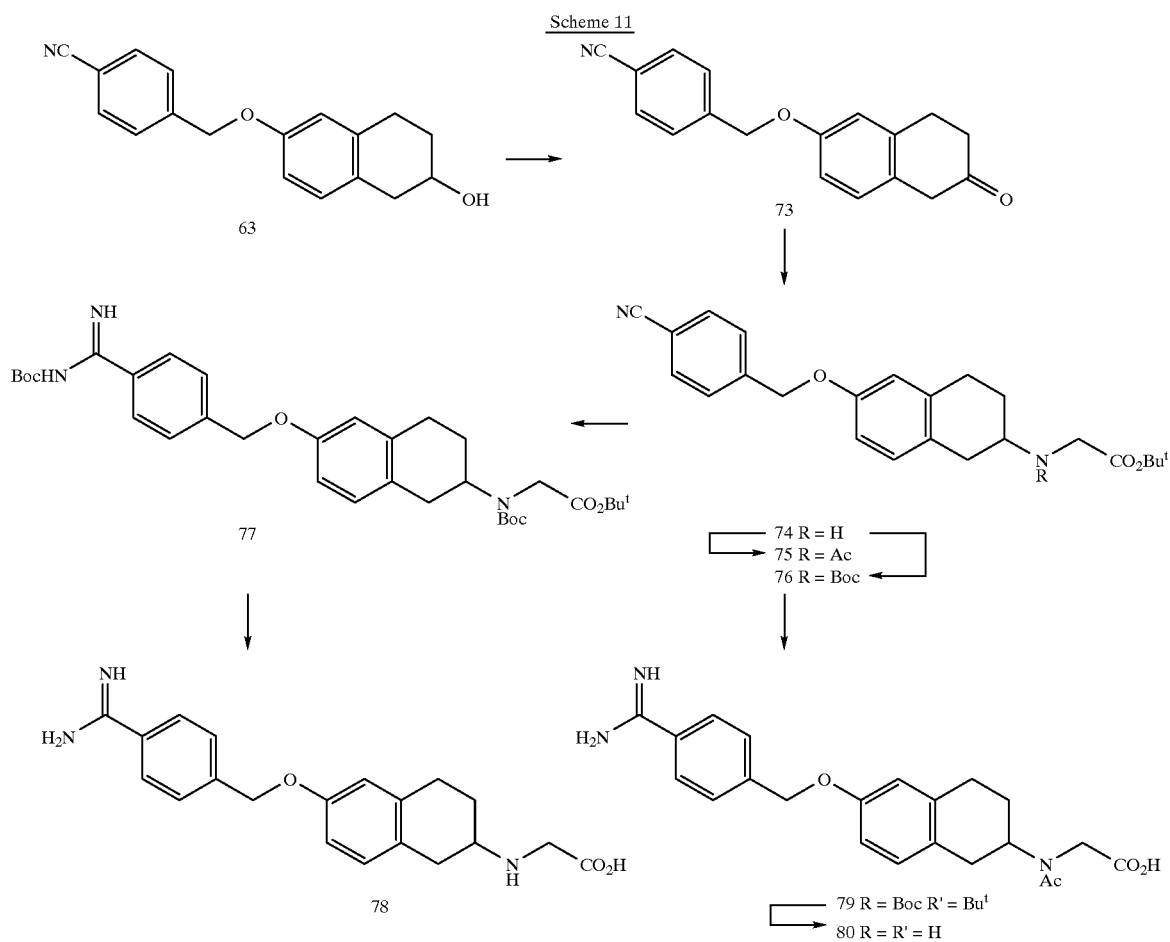

Scheme 11 outlines the preparation of 2,6-disubstituted tetralins in which the 2 position retains an α-aminoacetic acid residue and the 6 position is occupied by an ether linked benzamidine. The synthesis starts with alcohol 63 (Scheme 9) which is oxidized with TFAA and DMSO (method of Swern) giving ketone 73. This material is then reductively aminated with glycine tert-butyl ester giving 74. The secondary nitrogen is then either Boc protected (76) or acylated (75). The Boc derivative is then transformed into protected amidine 77 using the same sequence of reactions outlined in Scheme 1. The material is then fully deprotected with TFA giving 78. In a like manner, the acetyl derivative 75 is transformed into 80.

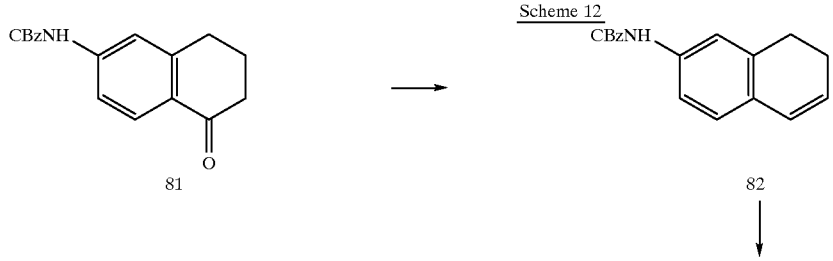

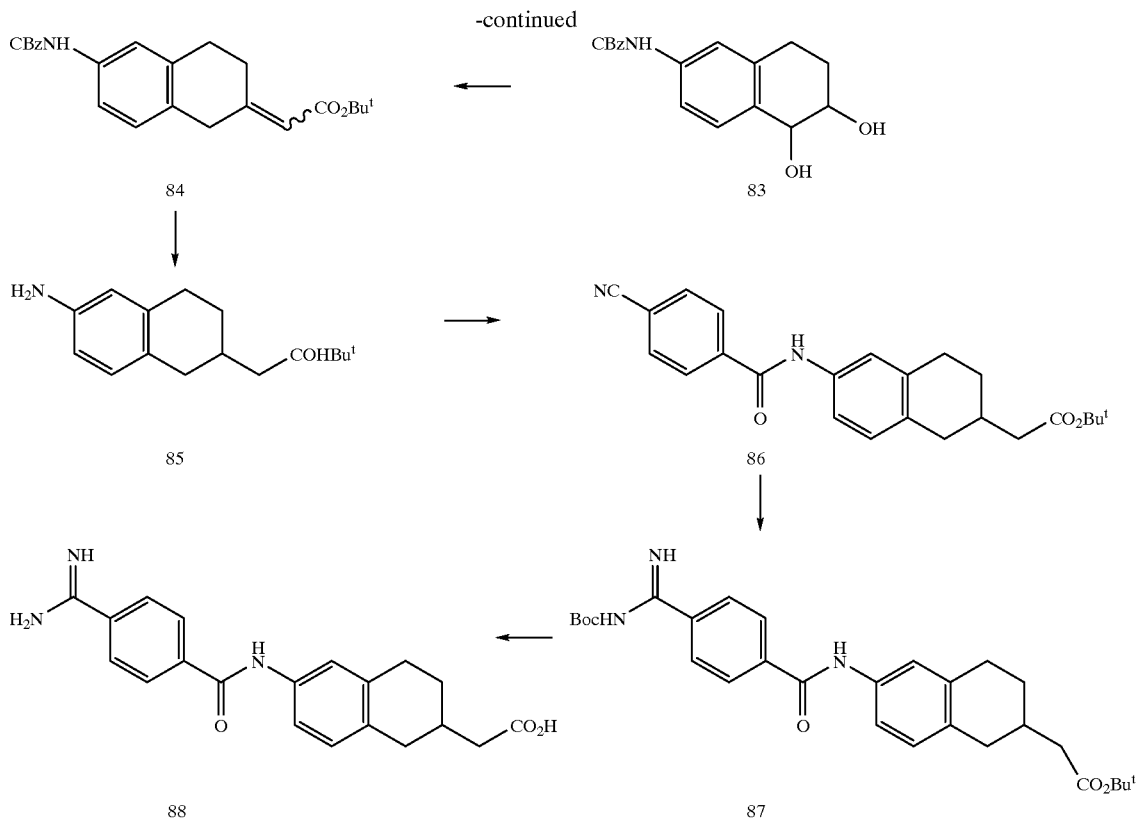

Scheme 12 outlines the preparation of tetralins having an acetic acid residue at $C_2$ and an amide linked benzamidine at $C_6$. In the first step, tetralone 81 is reduced with $NaBH_4$ and the resultant unstable alcohol is dehydrated with TsOH in benzene giving dihydronapthalene 82. Osymylation of 82 affords diol 83 which is then subjected to the action of TsOH in refluxing benzene. The unstable 2-tetralone thus formed is not isolated but rather allowed to react with the sodium salt of tert-butyl diethylphosphonoacetate giving unsaturated ester 84 as a mixture of olefin isomers. This material is subjected to hydrogenation over palladium which effects saturation of the olefin and removal of the CBz group providing aniline 85. Acylation of 85 with 4-cyanobenzoic acid is accomplished with the aid of EDCI and the resulting amide 86 is transformed into the Boc protected amidine 87 using conditions previously described in Scheme 1. Removal of the Boc moiety and cleavage of the tert-butyl ester is accomplished with TFA giving 88.

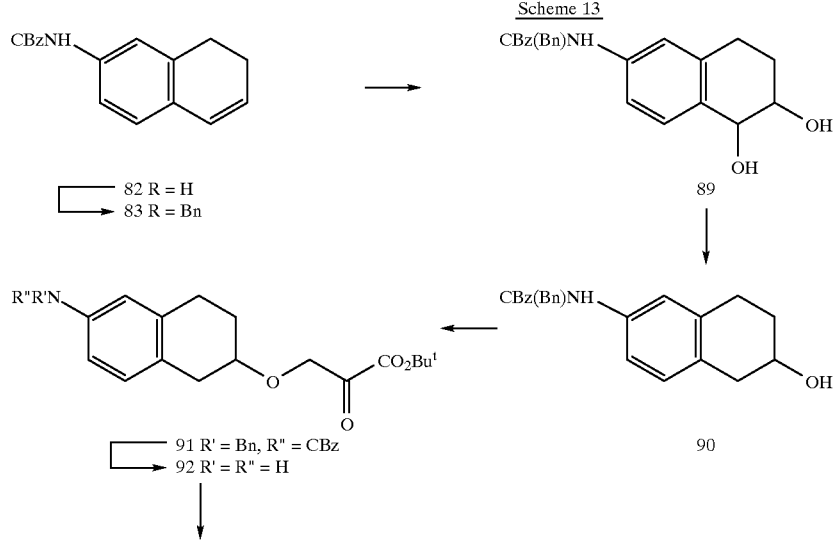

Scheme 13

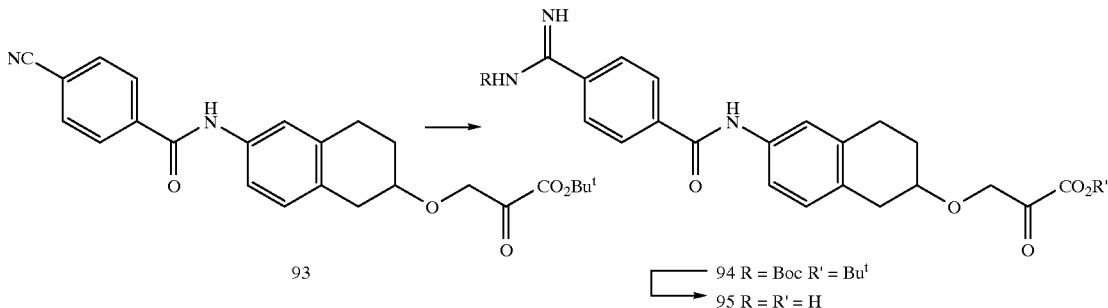

94 R = Boc R' = Bu$^t$
95 R = R' = H

Scheme 13 describes the preparation of tetralin derivatives in which position 2 is substituted with an α-alkoxyacetic acid moiety and position 6 is substituted by an amide linked benzamidine. In this scheme, compound 82 from Scheme 12 is allowed to react with NaH and benzylbromide giving tertiary carbamate 88. This material is then subjected to osmylation and dehydration in the same manner as described for compound 83 in Scheme 12. The formed unstable 2-tetralone is immediately reduced to alcohol 90 with NaBH$_4$. This material is alkylated with tert-butyl bromoacetate under phase transfer conditions resulting in ether 91. Catalytic hydrogenation liberates the 6-amino moiety (92) which is acylated with 4-cyanobenzoic acid in the presence of EDCI giving 93. Nitrile 93 is transformed into Boc protected amidine 94 using the series of transformations described in Scheme 1. Simultaneous deprotection of the amidine and acid moieties is accomplished with TFA giving final product 95.

Scheme 14

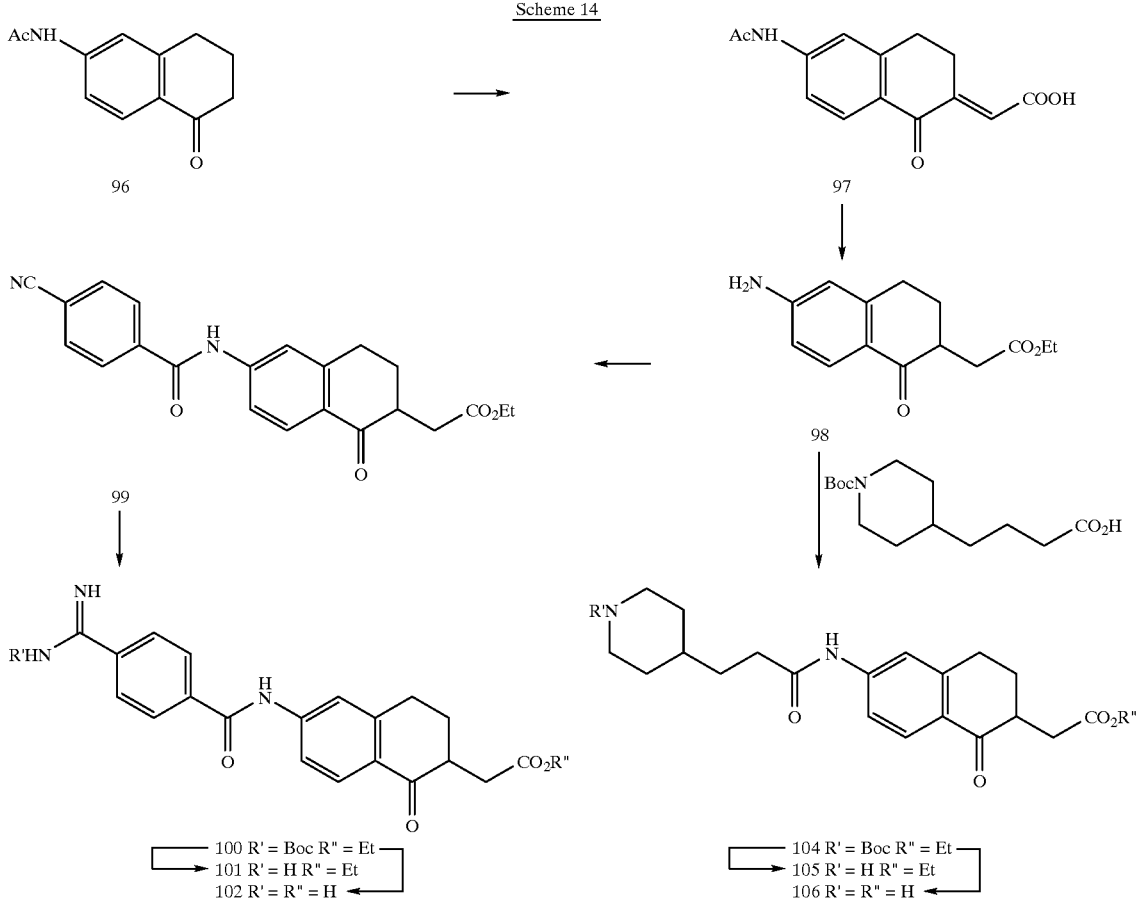

100 R' = Boc R" = Et
101 R' = H R" = Et
102 R' = R" = H

104 R' = Boc R" = Et
105 R' = H R" = Et
106 R' = R" = H

Scheme 14 outlines the synthesis of tetralins bearing an acetic acid moiety at position 2 and either an amide linked benzamidine or amide linked 4-alkylpiperidine at position 6. The scheme starts with tetralone 96 which is allowed to react with glyoxylic acid in the presence of NaOH yielding condensation product 97. The unsaturated ester 97 is reduced with Zn in HOAc and the resulting compound is transformed into aniline 98 by first removing the acetate with 6N HCl and then esterifying the acid moiety with ethanolic HCl. This material is then acylated with 4-cyanobenzoic acid via the agency of EDCI giving 99. The nitrile moiety of 99 is converted to Boc protected amidine 100 using the series of reactions described in Scheme 1. Saponification of the ester moiety with NaOH followed by treatment with TFA gives 102.

Compounds containing an amide linked 4-alkylpiperdine can be prepared by acylating aniline 98 with 103 giving analog 104. Saponification of ester 104 followed by TFA deprotection of the piperidine gives 106.

Scheme 15 teaches a method of preparing tetralone derivatives in which position 2 is occupied by an unsaturated acid and position 6 is substituted by either an amide linked benzamidine or a 4-akylpiperidine. In the first step, compound 97 (scheme 14) can be converted to aniline 107 by removing the acetate with 6N HCl and subsequent esterification with ethanolic HCl. This material can then be acylated with either 4-cyanobenzoic acid or the appropriate 4-alkylpiperidine (103). In the former case, the nitrile 111 can be transformed into amidine 112 using the same sequence of reactions described in Scheme 1. Saponification of 112 followed by treatment with TFA should yield 114. Piperidine adduct 108 can be subjected to saponification and TFA deprotection providing 110 in a similar manner.

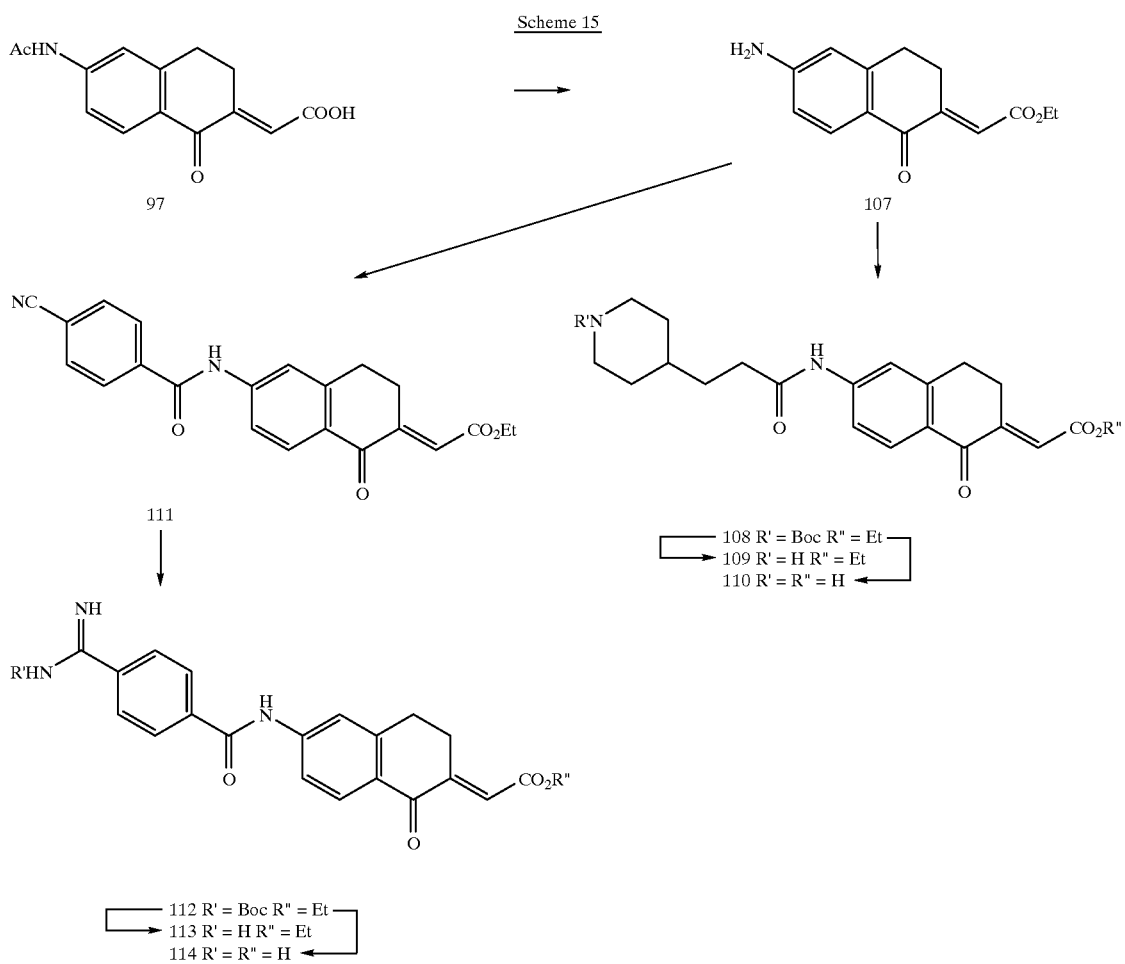

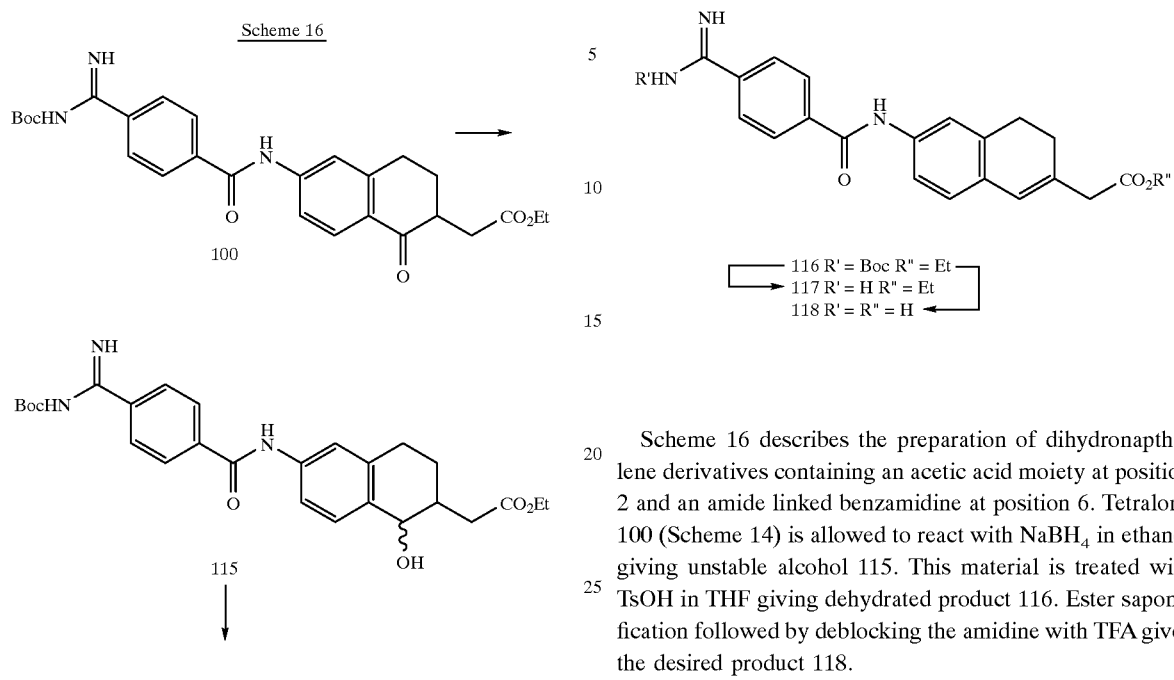

Scheme 16 describes the preparation of dihydronapthalene derivatives containing an acetic acid moiety at position 2 and an amide linked benzamidine at position 6. Tetralone 100 (Scheme 14) is allowed to react with NaBH$_4$ in ethanol giving unstable alcohol 115. This material is treated with TsOH in THF giving dehydrated product 116. Ester saponification followed by deblocking the amidine with TFA gives the desired product 118.

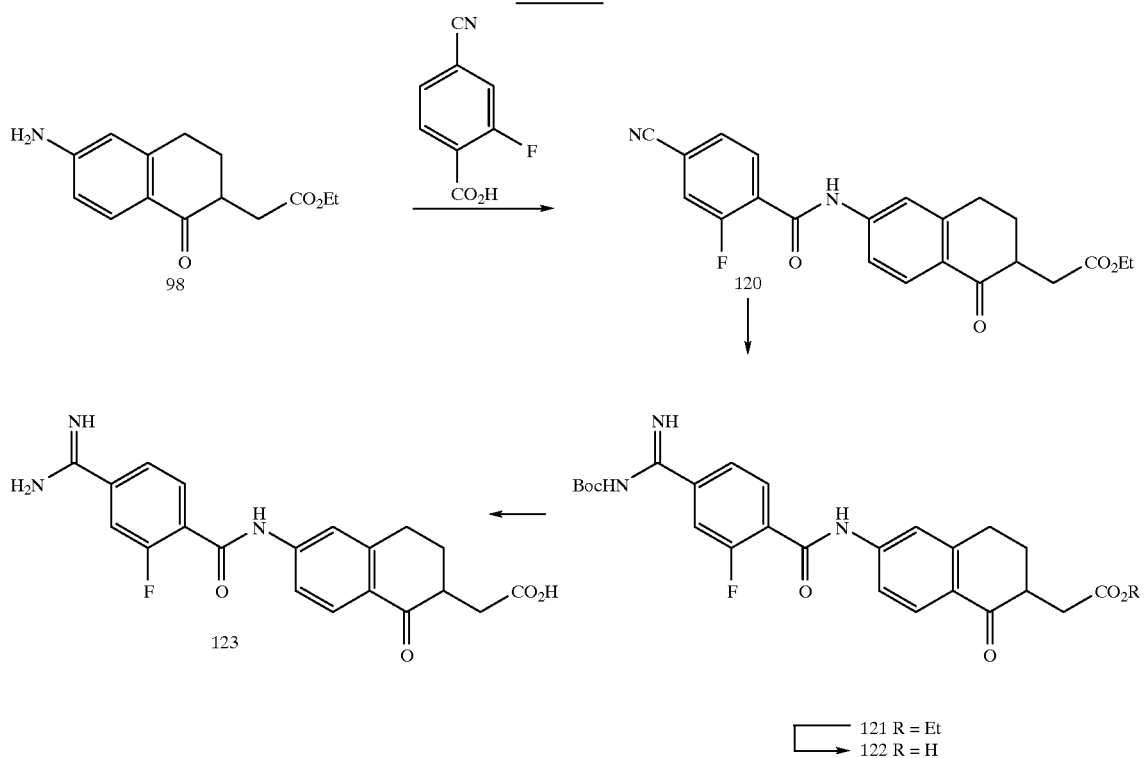

Scheme 17 outlines the general preparation of 2,6-disubstituted tetralones in which the 2 position is substituted with an acetic acid residue and the 6 position contains an amide-linked halogen-substituted benzamidine. Aniline 98 (prepared in Scheme 14) is allowed to react with benzoic acid 119 (prepared from 4-amino-2-fluoro-toluene using standard methods) in the presence of EDCI and DMAP. The resulting amide (120) is transformed into Boc protected amidine 121 using the same procedures outlined in Scheme 1. The ester moiety is then hydrolyzed giving acid 122 and then treatment with TFA provides compound 123.

In the first step of Scheme 18, bromonapthalene 124 is subjected to transmetalation with t-BuLi and the resulting anion is quenched with ethyl oxalate. The resulting adduct 125 is then reduced with $NaBH_4$ and the formed alcohol is acylated with acetic anhydride. Catalytic hydrogenation removes the benzilic acetate and liberates the 6-hydroxy moiety giving compound 126. The free phenol is then alkylated with α-bromo-p-tolunitrile in the presence of $K_2CO_3$ giving disubstituted naphthalene 127. The nitrile moiety is then transformed into the Boc protected amidine 128 using the same sequence of reactions previously

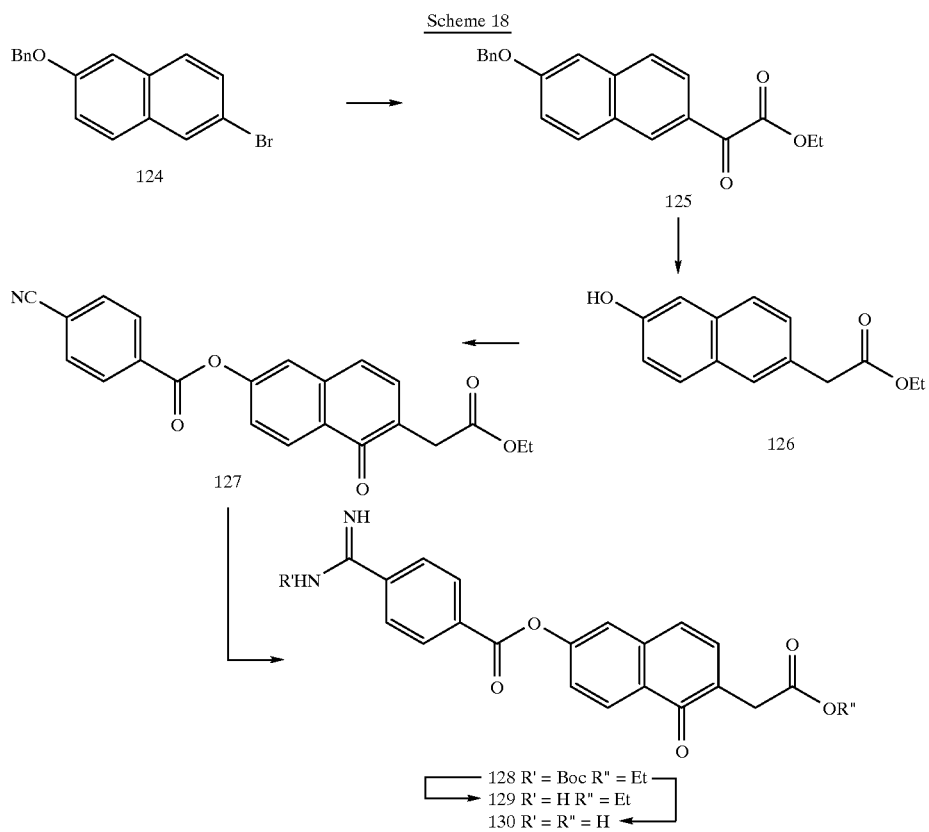

Scheme 18

Scheme 18 teaches a method of preparing 2,6-disubstituted napthalenes having an acetic acid residue at position 2 and an ether linked arginine isostere at position 6.

described in Scheme 1. Saponification of the ester in 128 followed by removal of the Boc group with TFA gives final compound 130.

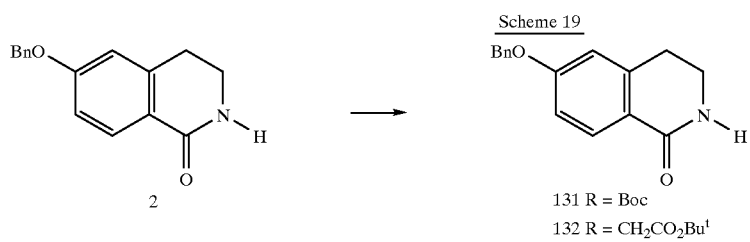

Scheme 19

-continued

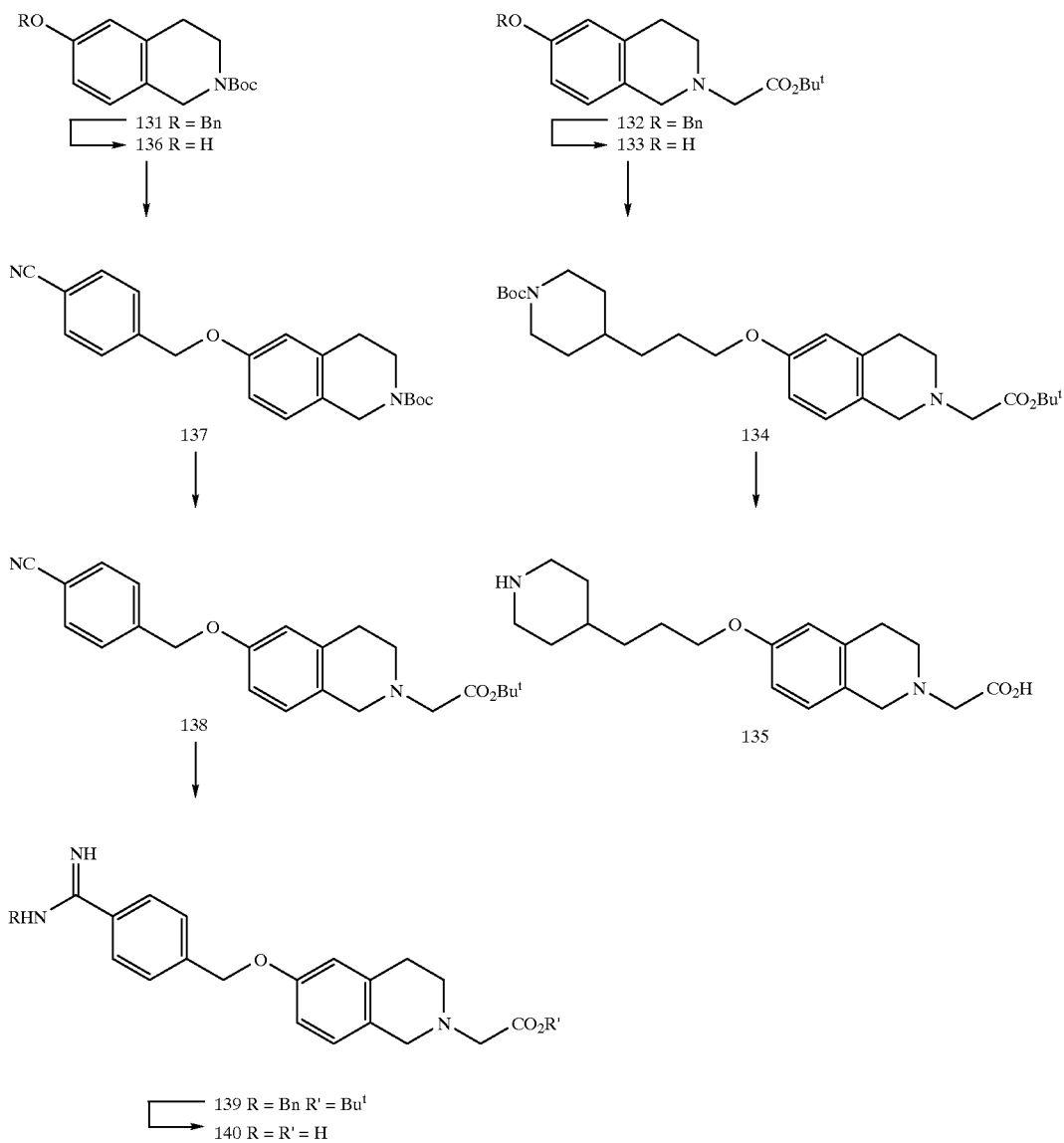

Scheme 19 describes the preparation of disubstituted tetrahydroisoquinoline derivatives bearing an acetic acid moiety at position 2 and either an ether linked benzamidine or 4-alkyl piperidine moiety at position 6 The initial isoquinoline nucleus is prepared by LiAlH$_4$ reduction of benzyl protected isoquinolone 2 (Scheme 1). This material was processed by either Boc protection giving compound 131 or alkylated with tert-butyl bromoacetate resulting in the formation of 132. The Boc protected material was subjected to hydrogenation which liberated the C$_6$ phenol which was then alkylated with α-bromotolunitrile giving adduct 137.

The Boc group of this compound was cleaved with TFA and the resulting amine was then alkylated with tert-butyl bromoacetate giving compound 138. This compound was transformed into the Boc protected amidine 139 and then to the deprotected variant 140 using the procedures outlined in Scheme 1. The N-alkylated compound 132 was similarly subjected to hydrogenation and the resulting phenol was alkylated with the appropriate 4-alkylpiperidine giving 134. This material was deprotected with TFA giving 135.

Scheme 20

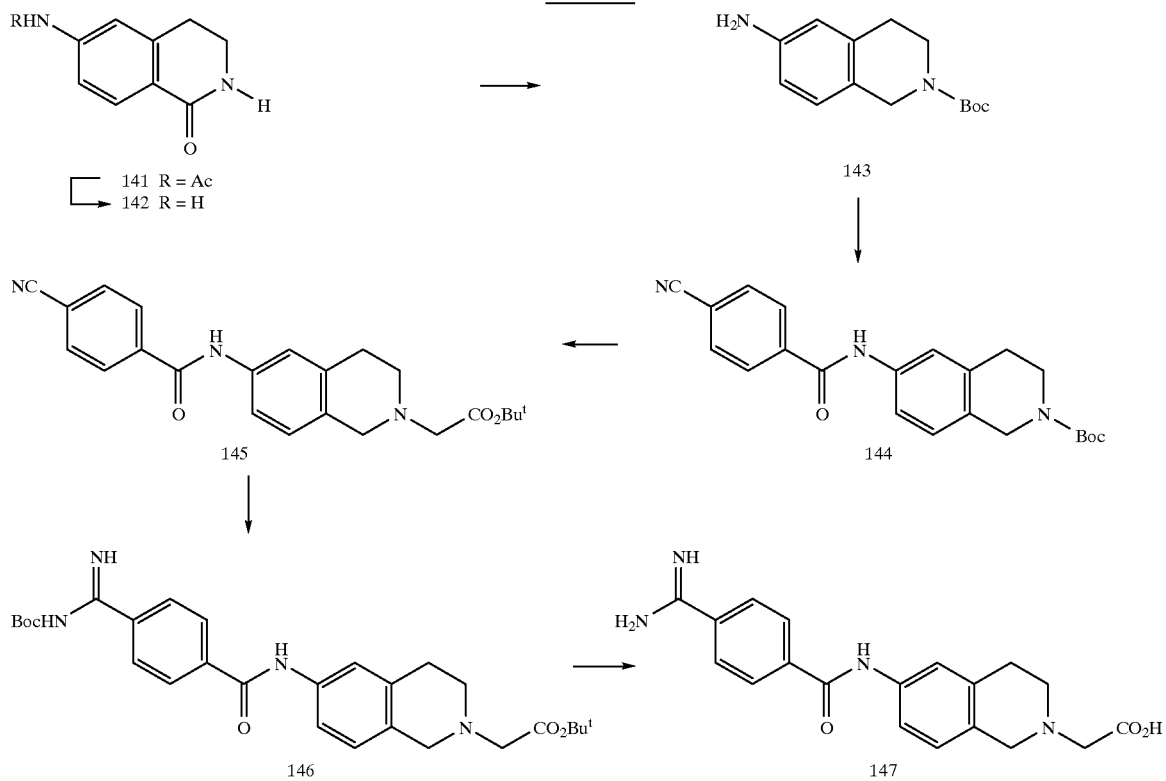

Scheme 20 teaches how to prepare 2,6-disubstituted tetrahydroisoquinoline derivatives bearing an acetic acid residue at position 2 and an amide linked benzamidine at position 6. The synthesis begins with acidic hydrolysis of the 6-acetamido group of isoquinolone 141 giving aniline 142. The crude material is then subjected to the action of benzyl bromide and $K_2CO_3$ in $CH_3CN$ giving a mixture of mono and di-benzyl protected isoquinolones. This mixture is subjected to $LiAlH_4$ reduction forming the tetrahydroisoquinoline which is immediately treated with di-tert-butyl dicarbonate. The formed Boc protected material is then hydrogenated over palladium providing aniline 143. This material is acylated with p-cyanobenzoic acid giving 144. Treatment of this material with TFA gives the secondary amine which is alkylated with tert-butyl bromoacetate providing 145. Conversion of 145 to the Boc protected amidine 146 and then to its deprotected congener 147 is accomplished using the same procedures as outlined in Scheme 1.

Scheme 21

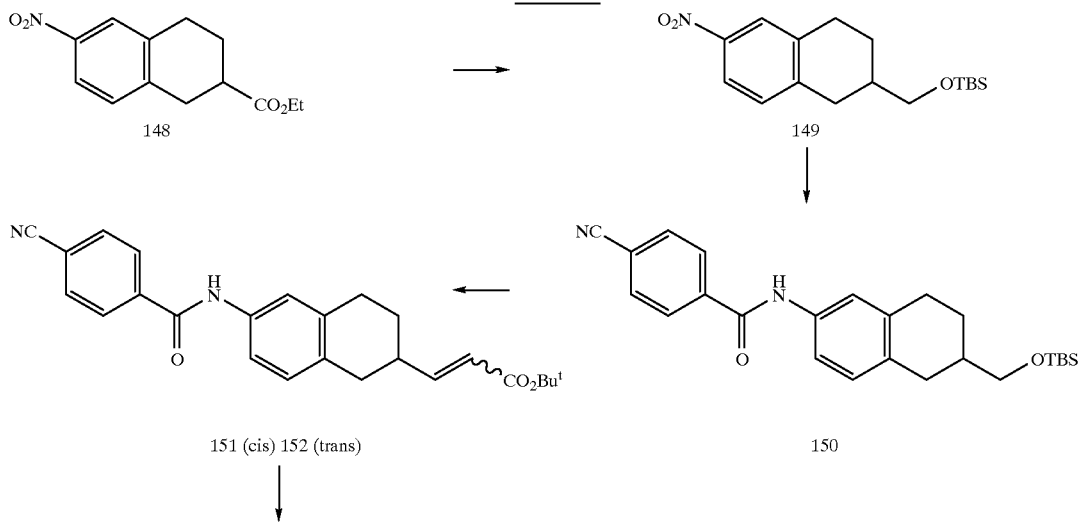

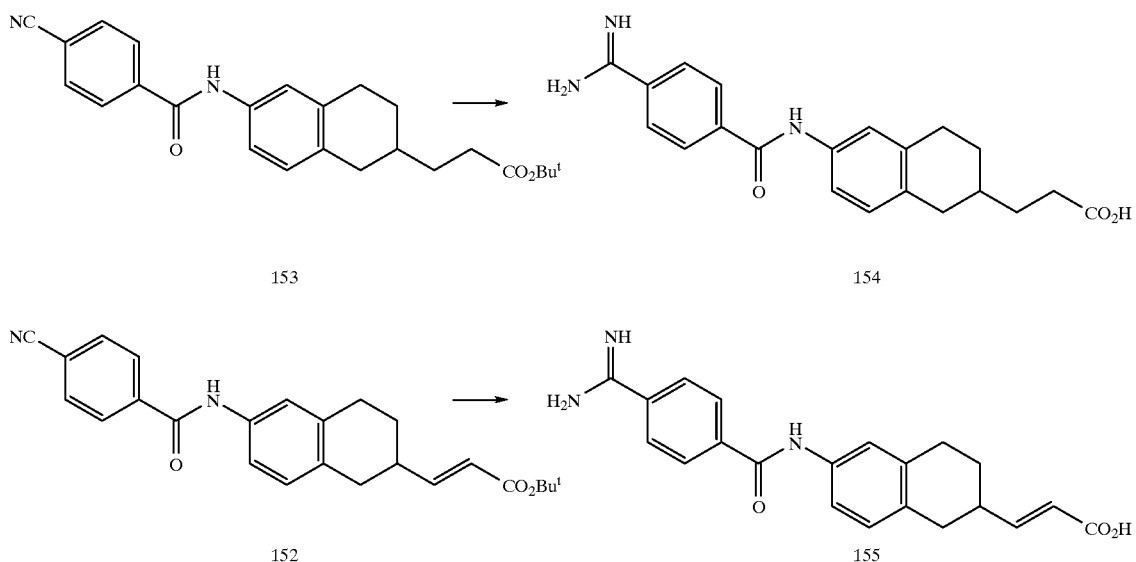

Scheme 21 describes a synthesis method suitable for the formation of 2,6-disubstituted tetralins containing a propionate or propenoate moiety at position 2 and an amide linked benzamidine at position 6. In the first step, nitro ester 148 is reduced with LiBH$_4$ and the resultant alcohol is protected as its TBS ether. Compound 149 is then subjected to hydrogenation and the formed aniline is immediately treated with EDCI and p-cyanobenzoic acid giving amide 150. The silyl group of 150 is removed and the derived alcohol is subjected to oxidation with DMSO and oxalyl chloride (method of Swern). The aldehyde thus formed is not purified, rather it is allowed to react with the sodium salt of t-butyl diethylphosphonoacetate which yields a separable mixture of 151 (cis) and 152 (trans) olefin isomers. The trans isomer 152 is converted to the Boc protected amidine and then to deprotected compound 155 using the sequence described in Scheme 1. The cis isomer is subjected to hydrogenation over palladium to give saturated analog 153. This material is also converted to the Boc protected amidine and then to its deprotected congener 154 as described in Scheme 1.

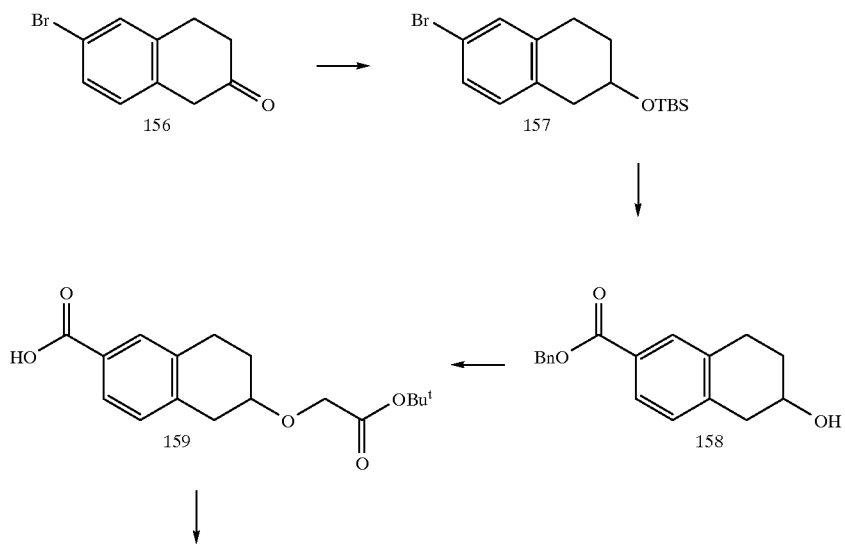

Scheme 22

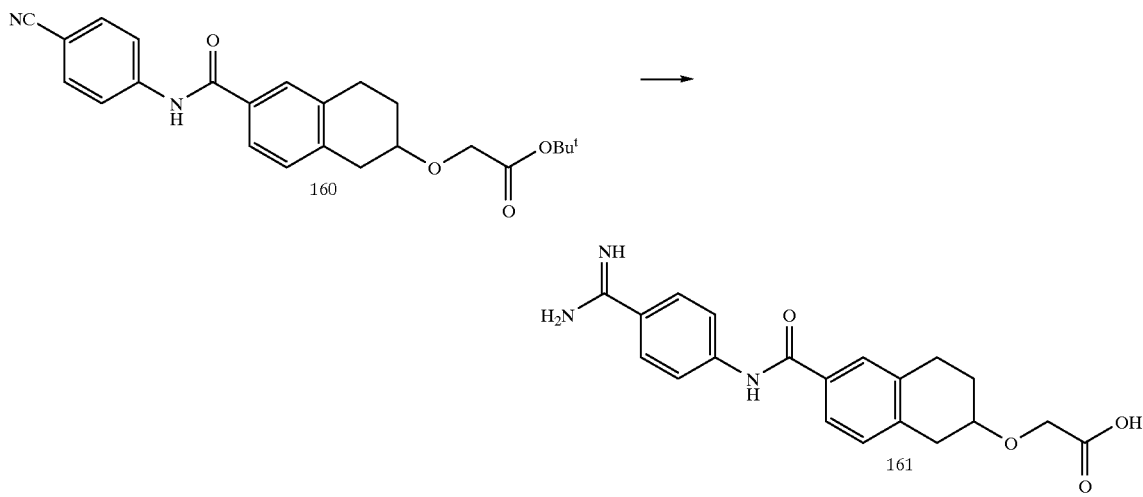

Scheme 22 describes a synthesis method for disubstituted tetralins bearing an α-alkoxyacetic acid residue at $C_2$ and a $C_6$ carboxyl linked benzamidine. This scheme begins with 6-bromo-2-tetralone (156) which is reduced with $NaBH_4$ and the resultant alcohol protected as its tert-butyldimethylsilyl (TBS) ether giving 157. Treatment of this compound with t-BuLi effects halogen metal exchange and the formed anion is quenched with $CO_2$. The resulting carboxylate is immediately transformed into the benzyl ester with benzyl alcohol and EDCI. The TBS group is removed during workup with TBAF affording alcohol 158. The free secondary hydroxyl is alkylated with tert-butyl bromoacetate using phase transfer conditions and the 6-carboxylate is liberated via catalytic hydrogenation affording 159. Amide 160 is the result of allowing 159 to react with 4-cyanoaniline in the presence of EDCI and DMAP. Nitrile 160 is converted to the BOC protected amidine and thereafter to the fully deprotected 161 using conditions outlined in Scheme 1.

Scheme 23

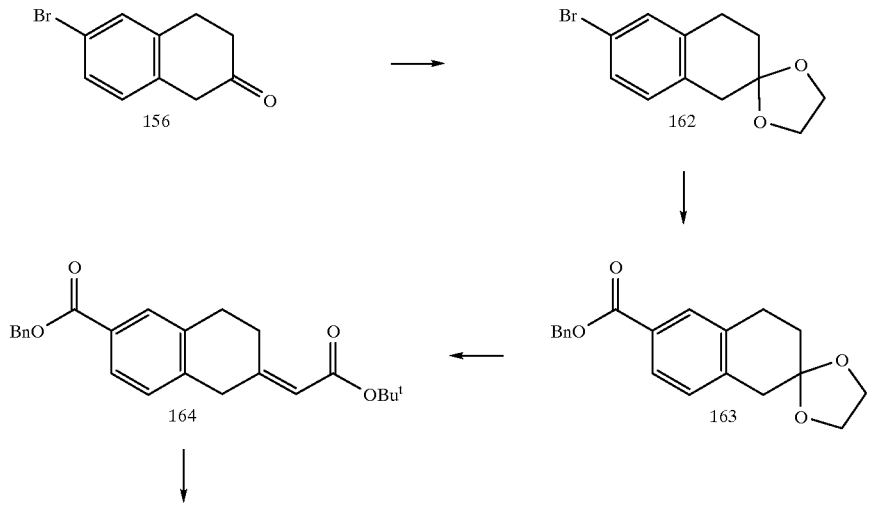

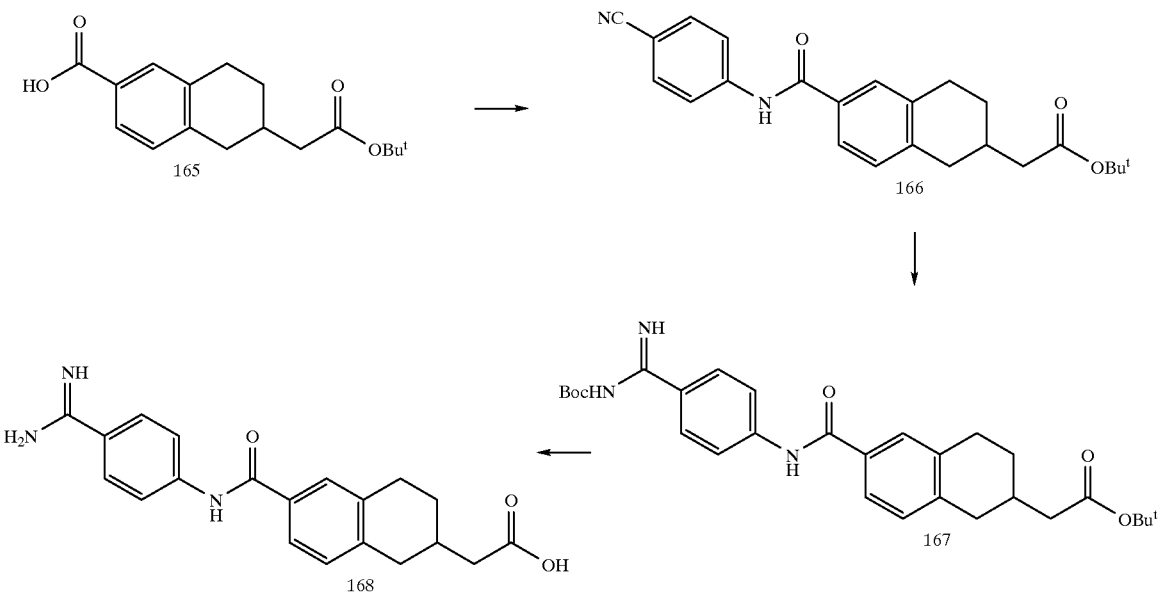

Scheme 23 outlines the preparation of tetralins having an acetic acid residue at $C_2$ and a $C_6$ carboxyl linked benzamidine. In the first step, bromotetralone 156 is treated with ethylene glycol and TsOH under dehydrating conditions giving ketal 162. This material is treated with tBuLi and the resulting anion is quenched with $CO_2$. The formed acid is immediately esterified with benzyl alcohol and EDCI giving 163. The spiro ketal contained in 163 is cleaved with aqueous HCl in acetone and the formed ketone is allowed to react with the sodium salt of tert butyl diethylphosphonoacetate giving 164 as a mixture of olefin isomers. Catalytic hydrogenation over Pd removes the unsaturation and liberates the $C_6$ carboxylate giving acid 165. Condensation of this compound with 4-aminobenzonitrile gives amide 166. Conversion of 166 to Boc protected amidine 167 and then to final compound 168 is accomplished using the same sequence outlined in Scheme 1.

Scheme 24

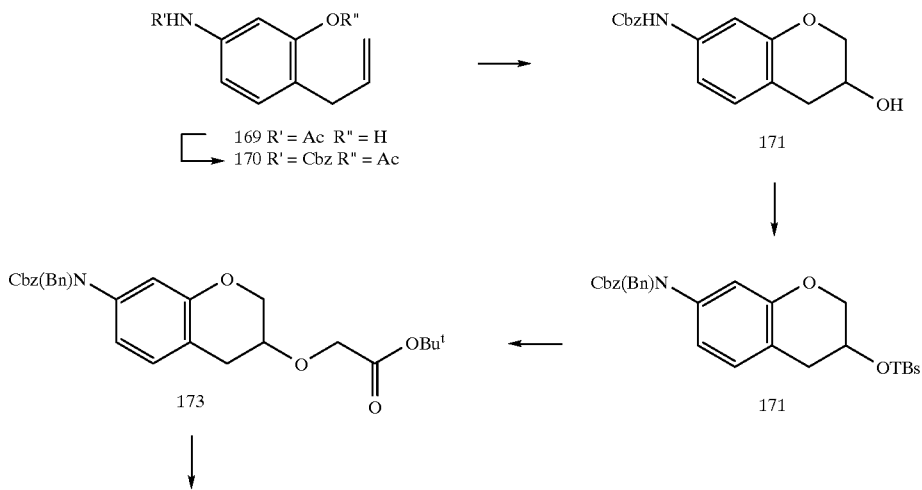

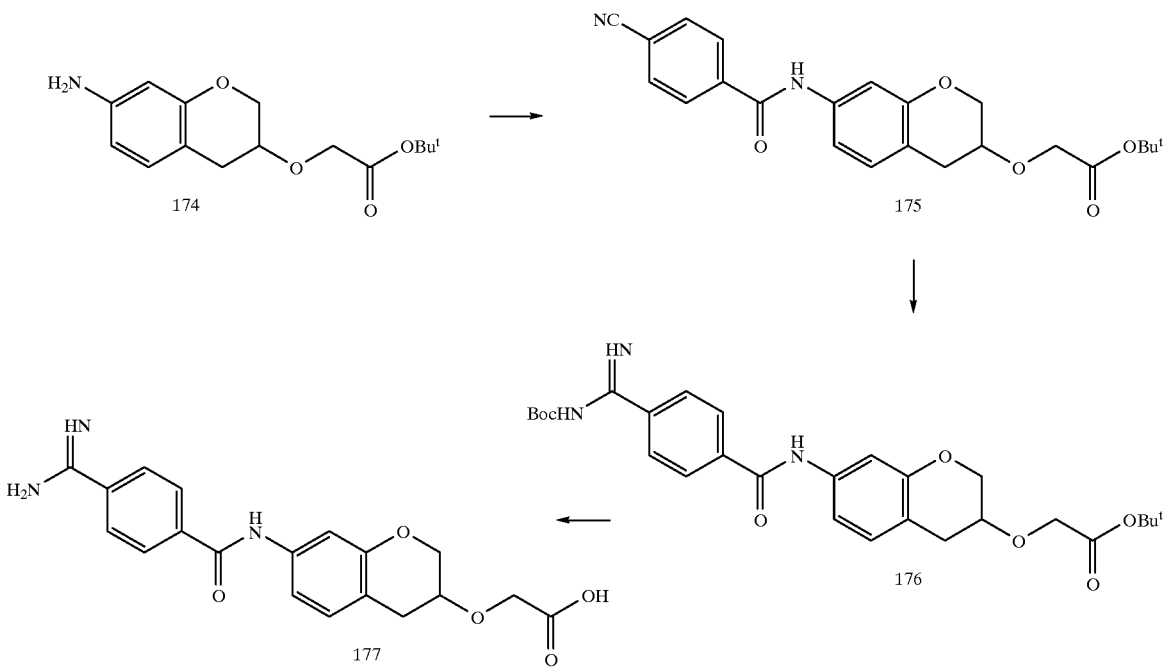

Scheme 24 describes the preparation of 3,7-disubstituted benzopyrans in which the 3-position is substituted with an α-alkoxyacetic acid moiety and the 7 position is substituted with an amide linked benzamidine. The synthesis begins with the allyl substituted aromatic 169. Acetamide hydrolysis is effected with NaOH in EtOH (Claisons alkali) and the resulting aniline is re-protected as its CBz counterpart. The free phenol is then acylated with acetic anhydride giving 170. The olefin is reacted with MCPBA giving the corresponding epoxide which is rearranged in the presence of NaI giving a mixture of 3-hydroxy and 3-acetoxy benzopyrans.

This mixture is created with LiOH giving alcohol 171. The alcohol moiety of 171 is then converted to its TBS ether and the resulting compound is alkylated on nitrogen to give fully protected 172. Liberation of the $C_3$ hydroxy with TBAF followed by alkylation with tert-butyl bromoacetate under phase transfer condition gives 173. Catalytic hydrogenation provides aniline 174 which is acylated with 4-cyanobenzoic acid, providing amide 175. This material is first converted to the corresponding protected benzamidine 176 and then to its deblocked congener 177 using the same sequence of events outlined in Scheme 1.

Scheme 25

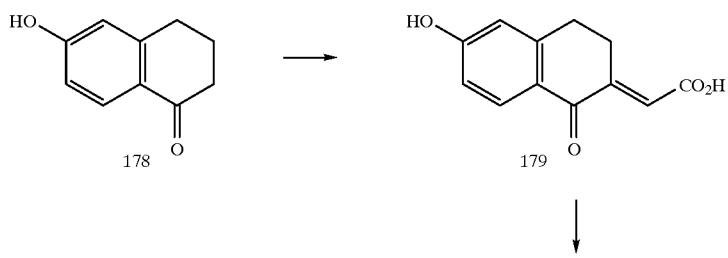

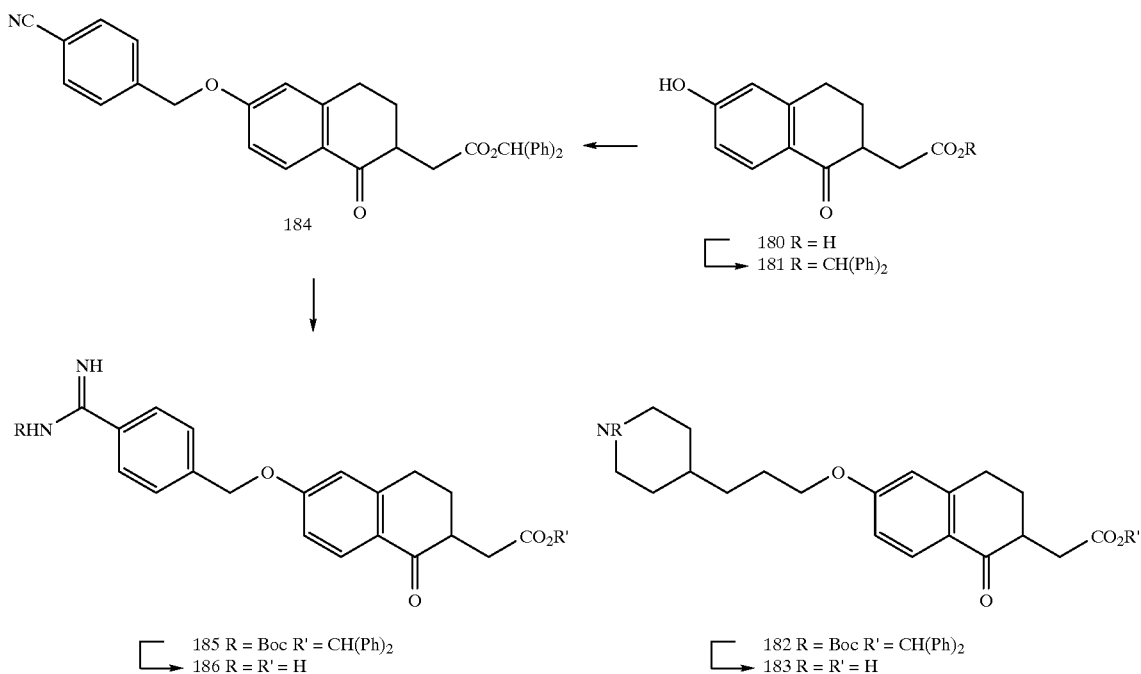

Scheme 25 outlines the preparation of 2,6-disubstituted tetralones in which the 2 position is substituted by an acetic acid moiety and the 6 position is substituted by either an alkoxy-linked benzamidine or alkoxy-linked 4-alkylpiperidine. In the first step, tetralone 178 is treated with NaOH and glyoxylic acid giving adduct 179. This material is reduced with Zn in acetic acid and the resulting acid (180) is reacted with diphenyldiazomethane giving benzhydryl ester 181. The free phenol can then be alkylated with α-bromo-p-tolunitrile to give 184 or with the appropriate 4-alkylpiperdine giving 182. Nitrile 184 is then converted to the corresponding Boc protected amidine 185 and then to the fully deprotected compound 186 using the same sequence of reaction outlined in Scheme 1. Compound 182 is deprotected with TFA giving compound 183.

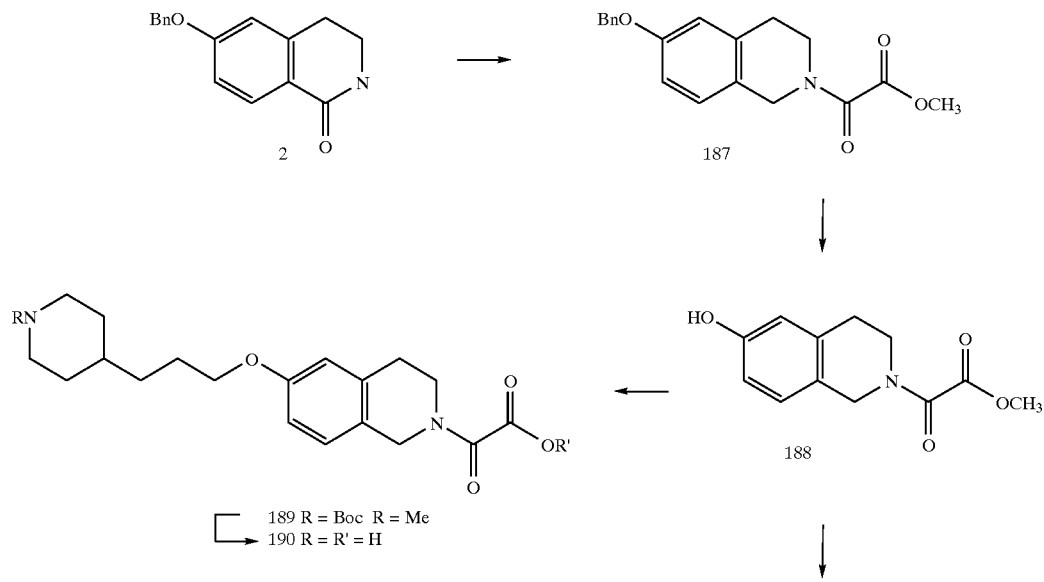

Scheme 26

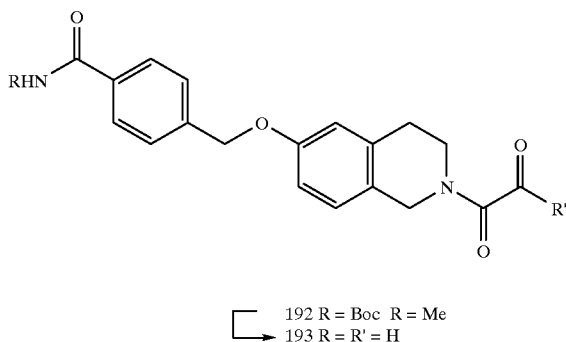

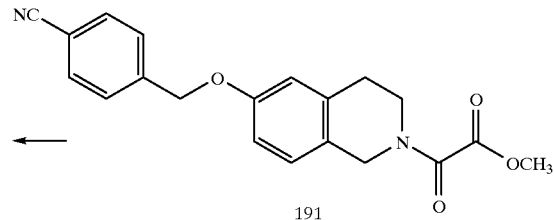

192 R = Boc  R = Me
193 R = R' = H

Scheme 26 teaches a method to prepare tetrahydroisoquinolins in which the 2-position is substituted by an oxamic acid residue and the 6-position contains an ether linked benzamidine. In the first step, isoquinolone 2 is treated with LiAlH$_4$ and the resulting product of reduction is acylated with methyl oxalylchloride giving compound 187. This material is subjected to hydrogenation and the resulting phenol is alkylated with either α-bromotolunitrile or the appropriate 4-alkylpiperidine giving compounds 191 and 189 respectively. The nitrile moiety of 191 is transformed into Boc protected amidine 192 using the same procedures described in scheme 1. This material is then saponified with NaOH and the resulting acid is treated with TFA giving 193. Compound 190 is prepared using a similar saponification deprotection sequence.

The following examples describe the preparation of compounds of the invention (unless otherwise indicated).

EXAMPLES

The following examples are provided to enable one skilled in the art to practice the present invention. These examples, however, are not to be read as limiting the scope of the invention as it is defined by the appended claims.

The reference numbers used in the following Examples refer to the corresponding compound shown in the preceding reaction Schemes 1 through 26:

Example 1

Preparation of 6-[[4-(aminoiminomethyl)phenyl]methoxy]-3,4-dihydro-1-oxo-2(1H)-isoquinolineacetic acid trifluoroacetate, a compound represented by the formula (7):

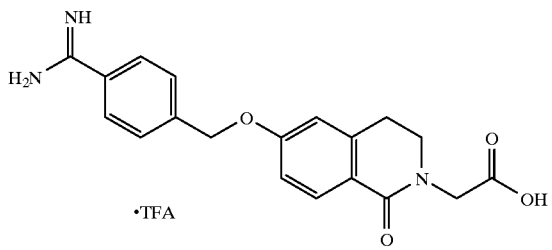

Part A:

A mixture of phenol (1) (6-hydroxy-3,4-dihydro-1-oxo-2(1H)isoquinolone (1.0 g, 6.14 mmol), benzyl bromide (1.0 g, 6.14 mmol) K$_2$CO$_3$ (0.93 g, 6.74 mmol), and acetone (15 mL) was maintained at reflux for 12 hours and then allowed to cool to room temperature. The mixture was then diluted with EtOAc and washed with H$_2$O. The organic material was dried (MgSO$_4$) and concentrated. The crude residue was recrystallized from EtOAc/Hexanes giving 1.53 g (98%) of (2) (6-benzyloxy-3,4-dihydro-1-oxo-2(1H)isoquinolone) as a white solid.

Part B:

To a solution of lactam (2) (0.1 g, 0.39 mmol) in THF (4 mL) was added sodium hydride (0.017 g of a 60% dispersion in mineral oil, 0.43 mmol). The resulting mixture was maintained at reflux for 1 hour and then allowed to cool to room temperature. The mixture was then treated with tert-butyl bromoacetate (0.07 g, 0.43 mmol). After one hour the reaction was quenched by the addition of H$_2$O (10 mL) and the resulting mixture was extracted with EtOAc. The combined extracts were dried (using MgSO$_4$) and concentrated. The crude material was purified by chromatography (silica gel, 2:1 Hexane:EtOAc) to give 0.14 g (99%) of (3a) as a white solid.

Part C:

A mixture of (3a) (0.13 g, 0.37 mmol), Pd/C (0.14 g, 10% on carbon), and EtOAc (5 mL) was stirred under an atmosphere of hydrogen (balloon) for 1.5 hours and then filtered. The filtrate was concentrated giving 0.13 g (100%) of (4) as an essentially pure white solid.

Part D:

A mixture of (4) (1.00 g, 3.60 mmol), α-bromo-p-toluninitrile (0.71 g, 3.60 mmol), K$_2$CO$_3$ (0.50 g, 3.60 mmol), and acetone (35 mL) was maintained at reflux for 4 hours and then allowed to cool to room temperature. The resulting mixture was concentrated and the residue chromatographed on silica (1:1 hexane-EtOAc) giving 1.38 g (98%) of (5) as a clear oil.

Part E:

A mixture of (5) (0.385 g, 0.982 mmol) pyridine (5.5 mL), and Et$_3$N (0.55 mL) was saturated with H$_2$S and allowed to stand for 2 days. This solution was then diluted with H$_2$O and the resulting mixture was extracted with EtOAc and the extracts concentrated. The crude isolate was taken up in a mixture of acetone (5 mL) and CH$_3$I (2.5 mL) and maintained at reflux for 1 hour. This mixture was allowed to cool to room temperature and then concentrated. The crude isolate was taken up in MeOH (5 mL) and treated with NH$_4$OAc. The resulting solution was maintained at 60° C. for 2 hours and then concentrated. The crude isolate was then taken up in a solution of THF/H$_2$O (1:1 6 mL) and treated with K$_2$CO$_3$ (0.179 g, 1.30 mmol) and Boc$_2$O (0.202 g, 0.95 mmol) and the resulting mixture was stirred at room temperature for 2 hours. The reaction mixture was then diluted with EtOAc and washed with water. The organic material was then concentrated and the crude isolate was purified by chromatography (silica gel 200–400 mesh, 30:1 CHCl$_3$-MeOH) giving 0.311 g (62%), of (6) as a clear oil.

Part F:

A mixture of (6) (0.311 g, 0.612 mmol) and TFA (5 mL) was maintained at room temperature for 1 hour and then concentrated. The residue was taken up in H$_2$O and the mixture was washed with Et$_2$O. The remaining aqueous material was lyophilized giving 0.31 g of (7) a white solid.

$^1$H NMR (300 MHz, CD$_3$OD) 3.03 (t, J=6.5 Hz, 2H), 3.68 (t, J=6.5 Hz, 2H), 4.29 (s, 2H), 5.30 (s, 2H), 6.94 (d, J=1.9 Hz, 1H), 7.0 (dd, J=1.9, 8.6 Hz, 2H), 7.69 (d, J=8.5 Hz, 2H), 7.84 (d, J=8.5 Hz, 2H), 7.87 (d, J=8.6 Hz, 1H), IR (CHCl$_3$) 2928, 1695, 1435, 1286 cm$^{-1}$, MS (FAB) m/e 354.1451 (354.1454 calc'd for C$_{19}$H$_{20}$N$_3$O$_4$).

Example 2

Preparation of 6-[[4-(aminoiminomethyl)phenyl] ethynyl]-3,4-dihydro-1-oxo-2(1H)-isoquinolineacetic acid trifluoroacetate, a compound represented by the formula (12a):

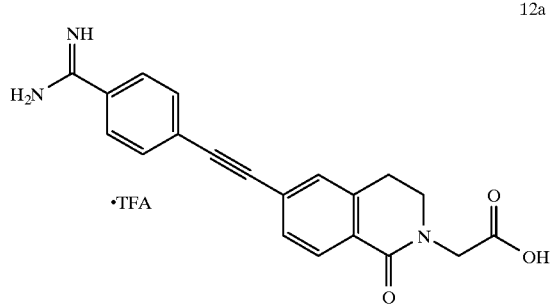

12a

Part A:

To a solution of (4) (9.5 g, 34.2 mmol) and freshly distilled pyridine (250 mL) was added trifluoromethanesulfonic anhydride (5.8 mL, 34.2 mmol) at 0° C. The resulting solution was allowed to warm to room temperature and then quenched by the addition of H$_2$O (125 mL). The mixture was extracted with EtOAc and the extract dried (MgSO$_4$) and concentrated. The crude material was purified by chromatography (silica gel, 4:1 hexane:ethyl acetate) to give 11.54 g (82.4%) of (8) (6-[[(trifluoromethyl)sufonyl] oxy]-3,4-dikydro-1-oxo-2(1H)isoquinolone acetic acid-1,1-dimethyl ester) as a white solid.

Part B:

A mixture of (8) (0.325 g, 0.79 mmol), (9a) (0.141 g, 1.11 mmol), bis (triphenylphosphine)-palladium (II) chloride (0.014 g, 0.02 mmol), anhydrous DMF (2.5 mL), and freshly distilled Et$_3$N (0.5 mL) was stirred at 90° C. for 1 hour. At this time, H$_2$O (25 mL) was added and the mixture was extracted with EtOAc (2×75 mL). The extracts were dried over MgSO$_4$ and concentrated. The crude material was purified by column chromatography (silica gel, 5:2 hexane:EtOAc) to give 0.173 g (57%) of (10a) as an orange solid.

Part C:

Following the general procedure used for the preparation of (6), (Example 1, part E) compound (11a) was prepared in 53% yield starting from 0.13 g of (10a).

Part D:

Following the general procedure employed for the preparation of (7), Example 1, part F compound (12a) (6-[[4-(aminoiminomethyl)phenyl]ethynyl]-3,4-dihydro-1-oxo-2 (1H)-isoquinolineacetic acid trifluoroacetate) was prepared in 76% yield starting from 0.089 g of (11a).

$^1$H NMR (300 MHz, CD$_3$OD) 3.11 (t, J=6.6 Hz, 2H), 3.73 (t, J=6.5 Hz, 2H), 4.34 (s, 2H), 7.51 (s, 1H), 7.55 (d, J=7.8 Hz, 1H), 7.78 (d, J=8.7 Hz, 2H), 7.83 (d, J=7.4 Hz, 2H), 7.97 (d, J=8.0 Hz, 1H); IR (KBr) 3355, 3085, 1709, 1610, 1183 cm$^{-1}$; MS(FAB) m/e 348.1332 (348.1348 calc'd for C$_{20}$H$_{18}$N$_3$O$_3$).

Example 3

Preparation of 6-[2-[4-(aminoiminomethyl)phenyl]ethyl]-3,4-dihydro-1-oxo-2(1H)-isoquinolineacetic acid trifluoroacetate, a compound represented by the formula (15a).

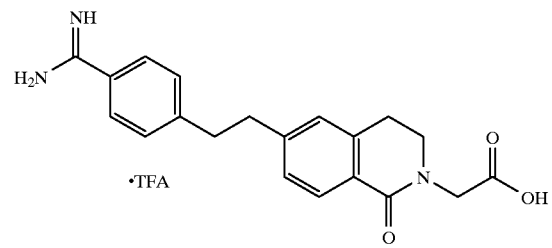

15a

Part A:

A mixture of (10a) (0.10 g, 0.26 mmol), Pd/C (0.10 g of 10% on carbon), and EtOAc (15 mL) was stirred under an atmosphere of hydrogen (balloon) for 1.5 hours and then filtered and concentrated to give 0.10 g, (100%) of (13a) as an off white solid.

Part B:

Following the general procedure employed in the preparation of (6),(Example 1, part E) compound (14a) was prepared in 78% yield starting from 0.095 g of (13a).

Part C:

Following the general procedure employed for the preparation of (7) (Example 1, part F), compound (15a) was prepared in 60% yield starting from 0.09 g of (14a).

$^1$H NMR (300 MHz, CD$_3$OD) 3.01 (m, 6H), 3.64 (t, J=6.6 Hz, 2H), 4.28 (s, 2H), 7.10 (m, 3H), 7.39 (d, J=8.2 Hz, 2H), 7.67 (d, 8.2 Hz, 2H), 7.77 (d, J=8.4 Hz, 1H); IR (KBr) 3337, 3112, 1641, 1210, 1188 cm$^{-1}$. MS(FAB) m/e 352.1655 (352.1661 calc'd for C$_{20}$H$_{22}$N$_3$O$_3$).

Example 4

Preparation of 6-[[4-(aminoiminomethyl)benzoyl] amino]-3,4-dihydro-1-oxo-2(1H)-isoquinolineacetic acid trifluoroacetate, a compound represented by the formula (22):

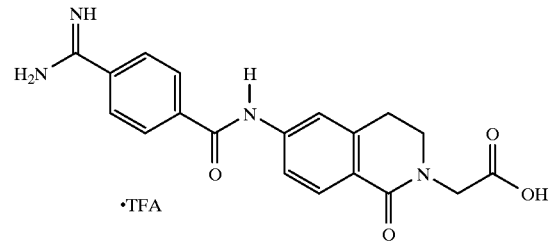

22

Part A:

A solution of (8) (Example 2, part A) (5.0 g, 12.2 mmol), DMF(25 mL), palladium (II) acetate (0.082 g, 0.37 mmol), triphenylphosphine (0.19 g, 0.73 mmol), freshly distilled Et$_3$N (3.4 mL, 24.4 mmol), and anhydrous MeOH (9.9 mL 244 mmol) was stirred under an atmosphere of CO (balloon)

at 65° C. for 15 hours. The reaction mixture was then allowed to cool and diluted with H$_2$O. The resulting mixture was extracted with EtOAc (2×100 mL). The combined extracts were dried (MgSO$_4$) and concentrated. The crude material was purified by column chromatography (silica gel; 3:1 Hexane:EtOAc) to afford 2.80 g (72%) of (16) (6-(methoxy carbonyl)-3,4-dihydro-1-oxo-2(1H)isoquinolone acetic acid-1,1-dimethyl ester) as an off-white solid.

Part B:

A solution of (16) (2.8 g, 8.7 mmol) and THF (87 mL) was treated with aqueous LiOH (87 mL of a 0.1N solution, 8.7 mmol) and the resulting solution was maintained at room temperature for 1 hour. The reaction mixture was then concentrated to ½ volume and extracted with EtOAc. A portion of the aqueous material was then acidified (pH=5) with 1N HCl and this mixture was then extracted with EtOAc. The combined extracts were then dried (MgSO$_4$) and concentrated affording 0.37 g of (17) as a viscous oil. The remaining aqueous material was lyopholized providing 2.06 g of (17) as the lithium salt.

Part C:

A solution of (17) (0.200 g, 0.66 mmol) and anhydrous toluene (50 mL) was treated with diphenyl-phosphorylazide (282.3 ml, 1.31 mmol) and freshly distilled Et$_3$N (0.18 mL, 1.31 mmol) and the resulting solution was maintained at 85° C. for 2 hours. The reaction was then allowed to cool to room temperature where it was treated with benzyl alcohol (0.14 mL, 1.31 mmol) and stirred for an additional hour. The reaction mixture was then concentrated and the crude isolate was purified by column chromatography (silica gel, 1:1 hexane:EtOAc) to yield 0.21 g (79%) of (18) (6-[(benzyloxy carbonyl)amino]-3,4-dihydro-1-oxo-2(1H) isoquinolone acetic acid-1,1-dimethyl ester) as a white solid.

Part D:

A mixture of (18) (0.20 g, 0.49 mmol), EtOH (20 mL), EtOAc (20 mL), and Pd/C (0.2 g of 10% on C) was stirred under an atmosphere of hydrogen (balloon) for 1 hour and then filtered and concentrated giving 0.138 g (100%) of (19) (6-amino-3,4-dihydro-1-oxo-2(1H)isoqunolone acetate acid-1,1-dimethyl ethyl ester) as a white solid.

Part E:

A solution of the (19) (0.125 g, 0.45 mmol), anhydrous dichloromethane (2.5 mL), para-cyanobenzoicacid (0.066 g, 0.45 mmol), 1-(3-dimethylaminopropyl)-3-ethyl-carbodiimide hydrochloride (EDCI) (0.095 g, 0.50 mmol) and 4-dimethylaminopyridine (DMAP) (10.0 mg) was maintained at room temperature for 2 hours and then concentrated. The crude isolate was purified by column chromatography (silica gel; 2:1 EtOAc:hexane) to give 0.176 g (96%) of a (20) as a white solid.

Part F:

Following general procedure employed for the synthesis of (6) (Example 1, part E), compound (21) was prepared in 36% yield starting from 0.17 g of (20).

Part G:

Following the general procedure employed for the synthesis of (7) (Example 1, part F), compound (22) was prepared in 76% yield starting from 0.07 g of (21).

$^1$H NMR (300 MHz, CD$_3$OD) 3.09 (t, J=6.6 Hz, 2H), 3.72 (t, J=6.6 Hz, 2H), 4.32 (s, 2H), 7.67 (d, 1H), 7.80 (br s , 1H), 7.94 (d, J=8.3 Hz, 3H), 8.16 (d, J=8.2 Hz, 2H); IR (CHCl$_3$) 3354, 3007, 1634, 1538, 1196 cm$^{-1}$; MS (FD) m/e 367. Anal. Calc'd for C$_{21}$H$_{19}$F$_3$N$_4$O$_6$: C, 52.50; H, 3.99; N, 11.66. Found: C, 52.62; H, 4.21: N, 11.41.

Example 5

Preparation of (+−)-6-[[4-(aminoiminomethyl)phenyl]methoxy]-3,4-dihydro-1-oxo-beta[hexylaminocarbonyl]-2(1H)-isoquinolone propanoic acid trifluoroacetate, a compound represented by the formula (29a).

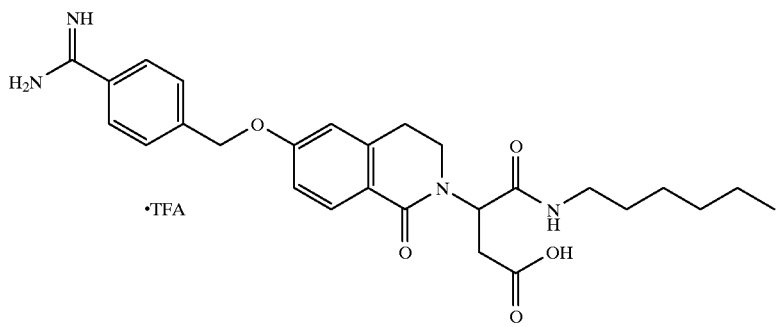

29a

Part A:

Following the procedure outlined for the preparation of (3a) (Example 1, part B), (3b) was prepared in 60% yield starting from lactam (2) and methyl bromoacetate.

Part B:

A solution of (3b) (1.95 g, 6.0 mmol) and THF (10 mL) was added to a solution of LHMDS (prepared from n-BuLi and HMDS according to standard protocols, 6.6 mmol) and THF (10 mL) at −78° C. After 1 hour, the solution was treated with tert-butyl bromoacetate (1.1 mL, 6.6 mmol) and allowed to warm to room temperature. The mixture was diluted with EtOAc (100 mL) and washed with H$_2$O. The organic material was dried (MgSO$_4$) and concentrated. Chromatography (silica gel, 200–400 mesh, 2:1 hexanes/EtOAc) gave 2.17 g (82%) of (23) as a clear oil.

Part C:

Following the procedure employed for the preparation of (4), (Example 1, part C) compound (24) was prepared in 94% yield starting from 2.17 g of (23).

Part D:

A mixture of (24) (1.79 g, 5.12 mmol), alpha-bromo-p-tolunitrile (1.11 g, 5.64 mmol), K$_2$CO$_3$ (0.78 g, 5.64 mmol), Bu$_4$NI (cat.) and DMF (10 mL) was stirred at 80° C. for 3 hours and then allowed to cool to room temperature. The mixture was then diluted with EtOAc (100 mL) and washed with H$_2$O. The organic material was concentrated and the crude isolate was purified by chromatography (silica gel, 200–400 mesh, 1.5:1 Hexanes/EtOAc) giving 2.32 g (98%) of (25) as a clear oil.

Part E:

A mixture of (25) (0.46 g, 1.0 mmol), aqueous LiOH (11 mL of a 0.1N solution, 1.1 mmol) and THF (11 mL) was stirred at room temperature for 3 hours and then concentrated to ½ volume. The remaining aqueous material was washed once with $Et_2O$ and then acidified to pH 3 with 1N HCl. This mixture was extracted with EtOAc and the combined extracts were concentrated. The crude residue was taken up in $CH_2Cl_2$ (5 mL) and treated with hexylamine (0.15 mL, 1.1 mmol), EDCI (0.28 g, 1.5 mmol), and DMAP (cat). The resulting mixture was maintained at room temperature for 4 hours and then diluted with EtOAc and washed with $H_2O$. The organic material was concentrated and the crude residue was purified by chromatography (silica gel, 200–400 mesh, 1:1 hexanes/EtOAc) giving 0.52 g (92%) of (27a) as a clear oil.

Part F:

Following the procedure employed for the preparation of (6) (Example 1, part E), (28a) was prepared in 75% yield starting from 0.52 g of (27a).

Part G:

Following the procedure for the preparation of (7) (Example 1, part F), (29a) was prepared in 82% yield starting from 0.47 g of (28a).

$^1$H NMR (300 MHz, $CD_3OD$) 0.83 (m, 3H), 1.27 (m, 6H), 1.45 (m, 2H), 2.71 (dd, J=8.0, 15.9 Hz, 1H), 3.1 (m, 5H), 3.59 (m, 2H), 5.28 (s, 2H), 5.48 (t, J=7.7 Hz, 1H), 6.90 (d, J=2.0 Hz, 1H), 6.98 (dd, J=2.0, 8.7 Hz, 1H), 7.70 (d, J=8.2 Hz, 2H), 7.83 (d, J=8.2 Hz, 2H), 7.90 (d, J=8.7 Hz, 1H); IR (KBr) 3331, 1668, 1605, 1278, 1188 $cm^{-1}$; MS (FAB) m/e 495.2612 (495.2607 calc'd for $C_{27}H_{35}N_4O_5$).

Example 6

Preparation of (+−)-6-[[4-(aminoiminomethyl)phenyl]methoxy]-3,4-dihydro-1-oxo-beta[[(phenylmethyl)amino]carbonyl]-2(1H)-isoquinolinepropanoic acid trifluoroacetate, a compound represented by the formula (29b).

Part A:

Following the procedure employed for the preparation of (27a) (Example 5, part E), (27b) was prepared in 84% yield starting from 0.46 g of (26) (Example 5, part E) and 0.12 g of benzyl amine.

Part B:

Following the procedure employed for the preparation of (6) (Example 1, part E), 28b was prepared in 76% yield starting from 0.45 g of (27b).

Part C:

Following the procedure employed for the preparation of (7) (Example 1, part F), (29b) was prepared in 72% yield starting from 0.41 g of (28b).

$^1$H NMR (300 MHz, $CD_3OD$) 2.70 (dd, J=7.2, 16.1 Hz, 1H), 2.90, (br t, J=6.4 Hz, 2H), 3.08 (dd, J=7.9, 15.8 Hz, 1H), 3.60 (m, 2H), 4.30 (dd, J=5.7, 14.9 Hz, 1H), 4.43 (dd, J=6.3, 14.9 Hz, 1H), 5.28 (s, 2H), 5.50 (t, J=7.5 Hz, 1H), 6.87(m, 1H), 6.97 (dd, J=2.0, 8.6 Hz, 1H), 7.25 (m, 5H), 7.71 (d, J=8.3 Hz, 2H), 7.87 (d, J=8.3 Hz, 2H), 7.90 (d, J=8.5 Hz, 1H); IR (KBr) 3333, 3092, 1668, 1604, 1278, 1185 $cm^{-1}$; MS (FAB) m/e 501.2151 (501.2138 calc'd for $C_{28}H_{29}N_4O_5$).

Example 7

Preparation of (+−)-6-[[4-(aminoiminomethyl) phenyl]methoxy]-3,4-dihydro-1-oxo-beta[[(4-methoxyphenylethyl)amino]carbonyl]-2(1H)-isoquinolone propanoic acid trifluoroacetate, a compound represented by the formula (29c).

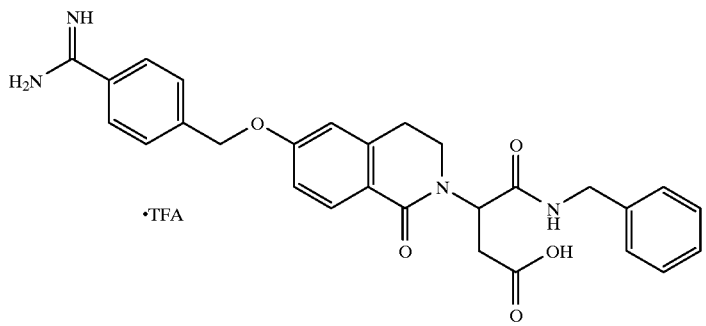

29b

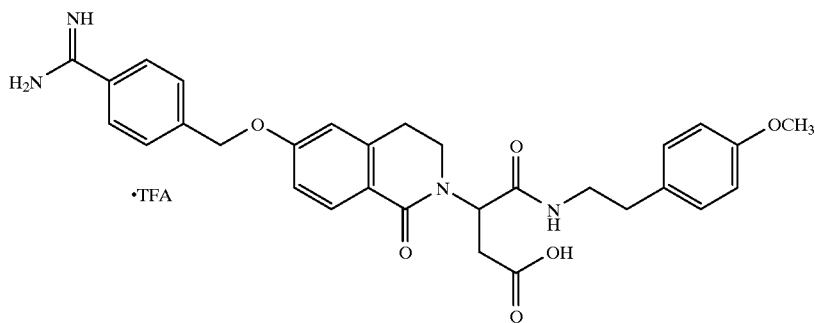

29c

Part A:

Following the general procedure employed for the preparation of (27a) (Example 5, part E), (27c) was prepared in 76% yield starting from 0.46 g of (26) and 0.17 g of p-methoxy phenethylamine.

Part B:

Following the procedure employed for the preparation of (6) (Example 1, part E), (28c) was prepared in 85% yield starting from 0.44 g of (27c).

Part C:

Following the procedure employed for the preparation of (7) (Example 1, part f), (29c) was prepared in 80% yield starting from 0.45 g of (28c).

$^1$H NMR (300 MHz, CD$_3$OD) 2.75 (m, 5H), 3.05 (dd, J=7.4, 15.8 Hz, 1H), 3.30 (m, 2H), 3.50 (m, 2H), 3.66 (s, 3H), 5.30 (s, 2H), 5.47 (t, J=7.7 Hz, 1H), 6.65 (d, J=8.4 Hz, 2H), 6.90 (m, 1H), 6.98 (dd, J=2.2, 8.5 Hz, 1H), 7.05 (d, J=8.4 Hz, 1H), 7.71 (d, J=8.4 Hz, 2H), 7.81 (d, J=8.4 Hz, 2H), 7.90 (d, J=8.5 Hz, 1H).

Example 8

Preparation of (+−)-6-[[4-(aminoiminomethyl)phenyl]methoxy]-3,4-dihydro-beta[(methylamino)carbonyl]-1-oxo-2(1H)-isoquinolinepropanoic acid trifluoroacetate, a compound represented by the formula (29d).

29d

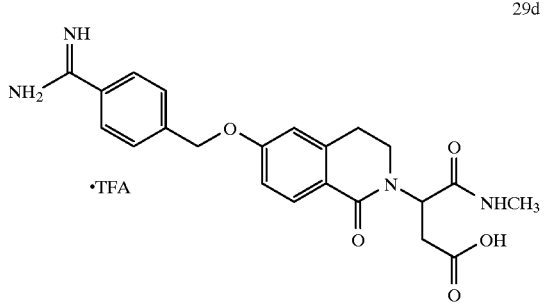

Part A:

Following the general procedure employed for the preparation of (27a), (27d) was prepared in 80% yield starting from 0.46 g of (26), 0.07 g of methylamine hydrochloride, and 0.15 mL of Et$_3$N.

Part B:

Following the procedure employed for the preparation of (6) (Example 1, part E), (28d) was prepared in 63% yield starting from 0.37 g of (27d).

Part C:

Following the procedure employed for the preparation of (7) (Example 1, part F), (29d) was prepared in 76% yield starting from 0.30 g of (28d).

$^1$H NMR (300 MHz, CD$_3$OD) 2.75 (m, 4H), 3.0 (m, 2H), 3.10 (dd, J=7.4, 15.9 Hz, 1H), 3.60 (m, 2H), 5.29 (s, 2H), 5.44 (t, J=7.6 Hz, 1H), 6.90 (d, J=2.2 Hz, 1H), 6.98 (dd J=2.2, 8.4 Hz, 1H), 7.69 (d, J=8.2 Hz, 2H), 7.82 (d, J=8.2 Hz, 2H), 7.89 (d, J=8.4 Hz, 1H); IR (KBr) 3335, 3105, 1668, 1605, 1480, 1278, 1185 cm$^{-1}$; MS (FAB) m/e 425.1819 (425.1825 calc'd for C$_{22}$H$_{25}$N$_4$O$_5$).

Example 9

Preparation of (+−)-6-[[4-(aminoiminomethyl)phenyl]methoxy]-beta[[(2-carboxyethyl)amino]carbonyl-3,4-dihydro-1-oxo-2(1H)-isoquinolinepropanoic acid trifluoroacetate, a compound represented by the formula (29e):

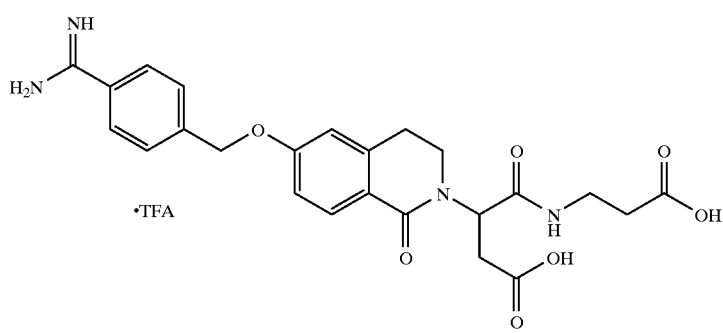

29e

Part A:

Following the general procedure employed for the preparation of (27a) (Example 5, part E), (27e) was prepared in 74% yield starting from 0.46 g of (26), 0.2 g of beta-amino-t-butylalanine hydrochloride, and 0.15 mL of Et$_3$N.

Part B:

Following the procedure employed for the preparation of (6) (Example 1, part E), (28e) was prepared in 65% yield starting from 0.42 g of (27e).

Part C:

Following the procedure employed for the preparation of (7) (Example 1, part F), (29e) was prepared in 89% yield starting from 0.45 g of (28e).

$^1$H NMR (300 MHz, CD$_3$OD) 2.48 (t, J=6.2 Hz, 2H), 2.65 (dd, J=8.2, 15.8 Hz, 1H), 3.05 (m, 3H), 3.35 (m, 2H), 3.50 (m, 2H), 5.28 (s, 2H), 5.49 (t, J=7.7 Hz, 1H), 6.89 (m, 1H), 6.95 (dd, J=2.2, 8.4 Hz, 1H), 7.68 (d, J=8.5 Hz, 2H), 7.84 (d, J=8.5 Hz, 2H), 7.90 (d, J=8.4 Hz, 1H); IR (KBr) 3338, 3108, 1669, 1604, 1278, 1187 cm$^{-1}$; MS (FAB) m/e 483. Anal. Calc'd for C$_{26}$H$_{27}$N$_4$O$_9$F$_3$: C, 52.35; H, 4.56; N, 9.39. Found: C, 52.43; H, 4.82; N, 9.13.

Example 10

Preparation of (+−)-6-[[4-(aminoiminomethyl)phenyl]methoxy]-β-(3-ethoxypropyl)-3,4-dihydro-1-oxo-2(1H)-isoquinolinepropanoic acid trifluoroacetate, a compound represented by the formula (36a):

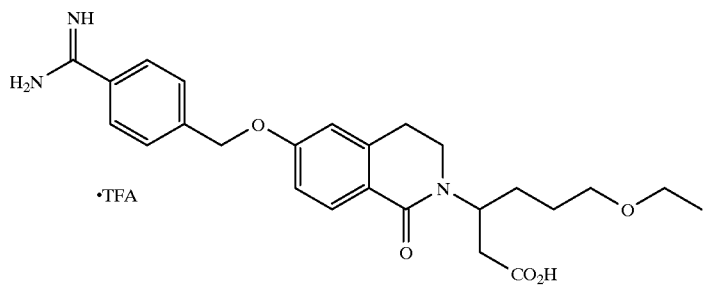

36a

Part A:

A solution of (2) (Example 1, part A), (6.53 g, 25.8 mmol), and THF (100 mL) was treated with NaH (1.13 g of a 60% dispersion in oil, 28.3 mmol) and the resulting mixture was maintained at reflux for 1 hour. The mixture was allowed to cool to room temperature and then was treated with 4-ethoxy-butanoyl chloride (28.4 mmol, prepared from the acid using standard protocols) and DMAP (cat). The resulting mixture was stirred at room temperature for 16 hours and then diluted with EtOAc. The organic mixture was washed with H$_2$O and concentrated. The crude material was purified by chromatography (silica gel, 200–400 mesh, hexanes-EtOAc, 4:1) to give 6.12 g (65%) of (30a) as a clear oil.

Part B:

A solution of (30a) (6.12 g, 16.7 mmol) in THF (10 mL) was treated with DIBAH (3.9 mL, 21.68 mmol) at −78° C. After 1 hour, the reaction was quenched by the addition of methanolic HCl (79 mL of a 1.1M solution). The mixture was then diluted with EtOAc and washed with H$_2$O and saturated aqueous NaHCO$_3$. The organic material was concentrated and the crude residue was purified by chromatography (silica gel, 200–400 mesh, hexanes/EtOAc/Et$_3$N, 3:1:0.01) giving 4.09 g (64%) of (31a) as a clear oil.

Part C:

A mixture of (31a) (3.25 g, 8.48 mmol), dimethyl-t-butylsiloxy-1-t-butoxy-ethene (9.24 g, 42.4 mmol), and CH$_2$Cl$_2$ (30 mL) was treated with BF$_3$.Et$_2$O (1.1 mL, 8.48 mmol) at −78° C. The resulting solution was allowed to warm to room temperature over 2 hours and then was quenched by the addition of saturated aqueous NaHCO$_3$ (20 mL). The resulting mixture was extracted with EtOAc and the extracts were concentrated. The crude product was purified by chromatography (silica gel, 200–400 mesh, hexanes/EtOAc 4:1) giving 3.1 g (78%) of (32a) as a clear oil.

Part D:

Following the procedure employed for the preparation of (4) (Example 1, part C), (33a) was prepared in 88% yield starting from 3.1 g of (32a).

Part E:

Following the procedure employed for the preparation of (25) (Example 5, part D), (34a) was prepared in 95% yield starting from 0.53 g of (33a).

Part F:

Following the procedure employed for the preparation of (6) (Example 1, part E), compound (35a) was prepared in 40% yield starting from 0.71 g of (34a).

Part G:

Following the procedure employed for the preparation of (7) (Example 1, part F), (36a) was prepared in 95% yield starting from 0.32 g of (35a).

$^1$H NMR (300 MHz, CD$_3$OD) 1.15 (t, J=6.9 Hz, 3H), 1.40–1.80 (m, 4H), 2.60 (m, 2H), 2.95 (m, 2H), 3.49 (m, 6H), 5.10 (m, 1H), 5.29 (s, 2H), 6.94 (d, J=2.3 Hz, 1H), 6.97 (dd, J=2.2, 8.7 Hz, 1H), 7.70 (d, J=8.3 Hz, 2H), 7.82 (d, J=8.5 Hz, 2H), 7.85 (d, J=8.8 Hz); IR (KBr) 3334, 3105, 1668, 1604, 1134 cm$^{-1}$; MS (FAB) m/e 454.2380 (454.2342 calc'd for C$_{25}$H$_{32}$N$_3$O$_5$.)

Example 11

Preparation of (+–)-6-[[4-(aminoiminomethyl)phenyl] methoxy]-β-butyl-3,4-dihydro-1-oxo-2(1H)-isoquinolinepropanoic acid trifluoroacetate, a compound represented by the formula (36b):

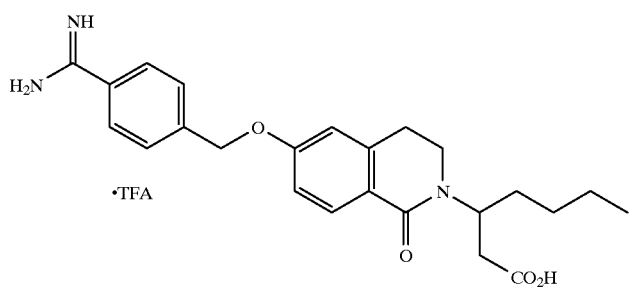

36b

Part A:

Following the procedure employed for the preparation of (30a) (Example 10, part A), (30b) was prepared in 90% yield starting from (2) (0.3 g) and pentanoic anhydride (0.24 g).

Part B:

Following the procedure employed for the preparation of (31a) (Example 10, part B), (31b) was prepared in 83% yield starting from 0.39 g of (30b).

Part C:

Following the procedure employed for the preparation of (32a) (Example 10, part C), (32b) was prepared in 52% yield starting from 0.33 g of (31a).

Part D:

Following the procedure employed for the preparation of (4) (Example 1, part C), (33b) was prepared in 98% yield starting from 0.22 g of (32b).

Part E:

Following the procedure employed for the preparation of (25) (Example 5, part D), (34b) was prepared in 95% yield starting from 0.17 g of (33b).

Part F:

Following the procedure employed for the preparation of (6) (Example 1, part E), (35b) was prepared in 56% yield starting from 0.23 g of (34b).

Part G:

Following the procedure employed for the preparation of (7) (Example 1, part F), (36b) was prepared in 89% yield starting from 0.14 g of (35b).

$^1$H NMR (300 MHz, CD$_3$OD) 0.89 (t, J=7.15 Hz, 3H), 1.35 (m, 4H), 1.65 (m, 2H), 2.60 (m, 2H), 2.95 (m, 2H), 3.50 (m, 2H), 5.05 (m, 1H), 5.29 (s, 2H), 6.95 (m, 2H), 7.70 (d, J=8.4 Hz, 2H), 7.84 (app t, J=8.2 Hz, 3H); IR (KBr) 3333, 3107, 1667, 1604, 1138 cm$^{-1}$; MS (FAB) m/e 424. Anal. Calc'd for C$_{26}$H$_{30}$N$_3$O$_6$: C, 58.10; H, 5.12; N, 7.82. Found: C, 57.85; H, 5.56; N, 7.56.

Example 12

Preparation of (+–)-6-[[4-(aminoiminomethyl)phenyl] methoxy]]-3,4-dihydro-1-oxo-β-pentyl-2(1H)-isoquinolinepropanoic acid trifluoroacetate, a compound represented by the formula (36c).

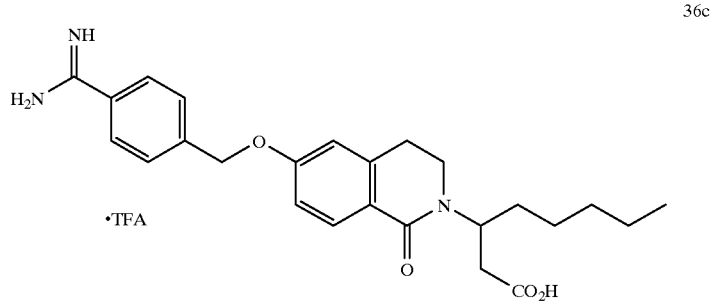

36c

Part A:

Following the procedure employed for the preparation of (30a) (Example 10, part A), (30c) was prepared in 95% yield starting from (2) (0.75 g) and hexanoyl chloride (0.43 g).

Part B:

Following the procedure employed for the preparation of (31a) (Example 10, part B), (31c) was prepared in 64% yield starting from 1.1 g of (30c).

Part C:

Following the procedure employed for the preparation of (32a) (Example 10, part C), (32c) was prepared in 70% yield starting from 0.80 g of (31c).

Part D:

Following the procedure employed for the preparation of (4) (Example 1, part C), (33c) was prepared in 87% yield starting from 0.69 g of (32c).

Part E:

Following the Procedure employed for the preparation of (25) (Example 5, part D), (34c) was prepared in 88% yield starting from 0.13 g of (33c).

Part F:

Following the procedure employed for the preparation of (6) (Example 1, part E), (35c) was prepared in 65% yield starting from 0.18 g of (34c).

Part G:

Following the procedure employed for the preparation of (7) (Example 1, part F), (36c) was prepared in 80% yield starting from (35b).

$^1$H NMR (300 MHz, CD$_3$OD) 0.90 (m, 3H), 1.30 (m, 6H), 1.60 (m, 2H), 1.26 (m, 2H), 2.97 (m, 2H), 3.45 (m, 2H), 5.05 (m, 1H), 5.30 (2, 2H), 6.88 (m, 1H), 6.94 (m, 1H), 7.70 (d, J=8.3 Hz, 2H); 7.83 (d, J=8.4 Hz, 2H), 7.85 (d, J=9 Hz, 1H), IR (KBr) 3335, 3115, 1668, 1481, 1188 cm$^{-1}$; MS (FAB) m/e 438.2366 (438.2393 calc'd for C$_{25}$H$_{32}$N$_3$O$_4$).

Example 13

Preparation of (+−)-6-[[4-(aminoiminomethyl)phenyl] methoxy]-3,4-dihydro-1-oxo-beta-(1,4-dioxyhexyl)-2(1H)-isoquinoline propionoic acid trifluoroacetate, a compound represented by the formula (36d).

Part A:

Following the procedure employed for the preparation of (30a) (Example 10, part A), (30d) was prepared in 81% yield starting from (2) (2.0 g) and 2-methoxyethoxy acetyl chloride (2.35 g).

Part B:

Following the procedure employed for the preparation of (31a) (Example 10, part B), (31d) was prepared in 52% yield starting from 2.35 g of (30d).

Part C:

Following the procedure employed for the preparation of (32a) (Example 10, part C), (32d) was prepared in 42% yield starting with 0.57 g of (31d).

Part D:

Following the procedure employed for the preparation of (4) (Example 1, part C), (33d) was prepared in 96% yield starting from 0.30 g of (32d).

Part E:

Following the procedure employed for the preparation of (25) (Example 5, part D) (34d) was prepared in 91% yield starting from 0.23 g of (33d).

Part F:

Following the procedure employed for the preparation of (6) (Example 1, part E), (35d) was prepared in 15% yield starting from 0.27 g of (34d).

Part G:

Following the procedure employed for the preparation of (7) (Example 1, part F), (36d) was prepared in 98% yield starting from 0.05 g of (35d).

$^1$H NMR (300 MHz, CD$_3$OD): 2.70 (t, J=6.2 Hz, 2H), 2.93 (t, J=6.2 Hz, 2H), 3.30 (s, 3H), 3.47–3.78 (m, 8H), 5.09 (br s, 1H), 5.29 (s, 2H), 6.88 (d, J=2.2 Hz, 1H), 6.95 (dd, J=2.2, 8.7 Hz, 1H), 7.82 (d, J=8.0 Hz, 2H), 7.84–7.86 (m, 3H). IR (KBr) 3350, 3114, 1669, 1604, 1482, 1385, 1279, 1186, 1029, 842 cm$^{-1}$; MS (FAB) m/e=456.3. Anal. Calc'd for C$_{26}$H$_{30}$F$_3$N$_3$O$_8$: C, 54.84; H, 5.31; N, 7.38. Found: C, 54.61; H 5.26; N, 7.37.

Example 14

Preparation of (+−)-6-[[4-(aminoiminomethyl)phenyl] methoxy]-ethyl-3,4-dihydro-1-oxo-2(1H)-isoquinolinepropanoic acid trifluoroacetate, a compound represented by the formula (36e).

36d

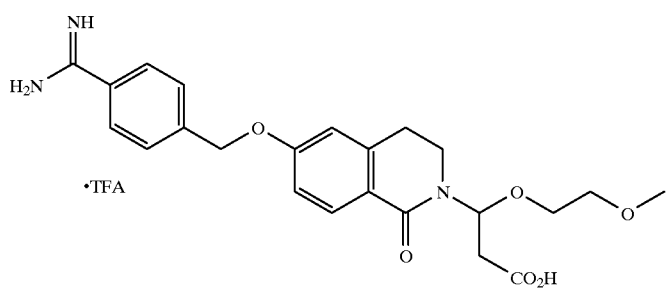

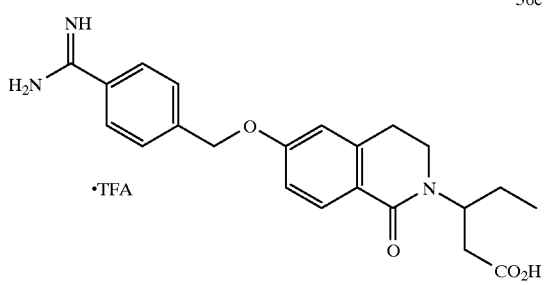

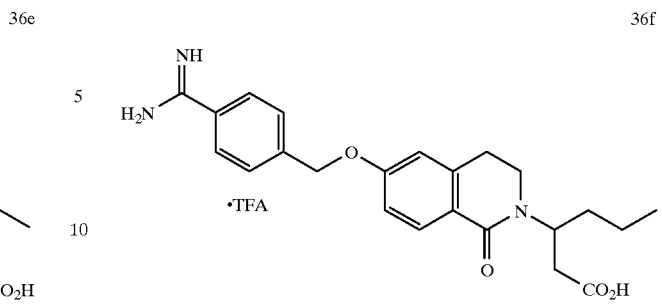

Part A:

Following the procedure employed for the preparation of (30a) (Example 10, part A), (30e) was prepared in 69% yield starting from (2) (1.5 g) and propanoyl chloride (1.26 g).

Part B:

Following the procedure employed for the preparation of (31a) (Example 10, part B), (31e) was prepared in 73% yield starting from 1.2 g of (30e).

Part C:

Following the procedure employed for the preparation of (32a) (Example 10, part C), (32e) was prepared in 49% yield starting from 0.92 g of (32e).

Part D:

Following the procedure employed for the preparation of (4) (Example 1, part C), (33e) was prepared in 89% yield starting from 0.55 g of (32e).

Part E:

Following the procedure employed for the preparation of (25) (Example 5, part D), (34e) was prepared in 86% yield starting from 0.36 g of (33e).

Part F:

Following the procedure employed for the preparation of (6) (Example 1, part E), (35e) was prepared in 36% yield starting from 0.38 g of (34e).

Part C:

Following the procedure employed for the preparation of (7) (Example 1, part F), (36e) was prepared in 92% yield starting from 0.22 g of (35e).

$^1$H NMR (300 MHz, CD$_3$OD): 0.91 (t, J=7.3 Hz, 3H), 1.62–1.69 (m, 2H), 2.55–2.62 (m, 2H), 2.92–2.97 (m, 2H), 3.42–3.53 (m, 2H), 4.94 (m, 1H), 5.29 (s, 2H), 6.89 (d, J=2.5 Hz, 1H), 6.95 (dd, J=2.5, 8.6 Hz, 1H), 7.70 (d, J=8.4 Hz, 2H), 7.84–7.87 (m, 3H). IR(KBr) 3330, 3109, 2973, 1670, 1604, 1481, 1344, 1256, 1041, 835 cm$^{-1}$; MS(FAB) m/e 396.1923, (396.1923 calc'd for C$_{22}$H$_{26}$N$_3$O$_4$).

Example 15

Preparation of (+−)-6-[[4-(aminoiminomethyl)phenyl]methoxy]-3,4-dihydro-1-oxo-β-propyl-2(1H)-isoquinolinepropanoic acid trifluoroacetate, a compound represented by the formula (36f).

Part A:

Following the procedure employed for the preparation of (30a) (Example 10, part A), (30f) was prepared in 77% yield starting from (2) (Example 1, part A) (1.0 g) and butanoyl chloride (0.98 g).

Part B:

Following the procedure employed for the preparation of (31a) (Example 10, part B), (31f) was prepared in 73% yield starting from 0.6 g of (30f).

Part C:

Following the procedure employed for the preparation of (32a) (Example 10, part C), (32f) was prepared in 46% yield starting from 0.44 g of (31f).

Part D:

Following the procedure employed for the preparation of (4) (Example 1, part C), (33f) was prepared in 90% yield starting from 0.24 g of (32f).

Part E:

Following the procedure employed for the preparation of (25) (Example 5, part D), (34f) was prepared in 88% yield starting from 0.16 g of (33f).

Part F:

Following the procedure employed for the preparation of (6) (Example 1, part E), (35f) was prepared in 44% yield starting from 0.19 g of (34f).

Part G:

Following the procedure employed for the preparation of (7) (Example 1. part F), (36f) was prepared in 66% yield starting from 0.085 g of (35f).

$^1$H NMR (300 MHz, CD$_3$OD): 0.95 (t, J=7.3 Hz, 3H), 1.29–1.36 (m, 2H), 1.54–1.71 (m, 2H), 2.56–2.62 (m, 2H), 2.91–2.96 (m, 2H), 3.43–3.53 (m, 2H), 5.09 (br s, 1H), 5.29 (S, 2H), 6.88 (d, J=2.1 Hz, 1H), 6.96 (dd, J=2.1, 8.5 Hz, 1H), 7.70 (d, J=8.2 Hz, 2H), 7.82 (d, J=8.2 Hz, 2H), 7.85 (d, J=8.5 Hz, 1H); IR (KBr) 3327, 3106, 2963, 2874, 1670, 1628, 1604, 1480, 1278, 1136 cm$^{-1}$; MS (FAB) m/e 410.2077 (410.2079 calc'd for C$_{23}$H$_{28}$N$_3$O$_4$).

Example 16

Preparation of (+−)-6-[[4-(aminoiminomethyl)phenyl]methoxy]-3,4-dihydro-1-oxo-β-phenyl-(1H)-isoquinolinepropanoic acid trifluoroacetate, a compound represented by the formula (36g).

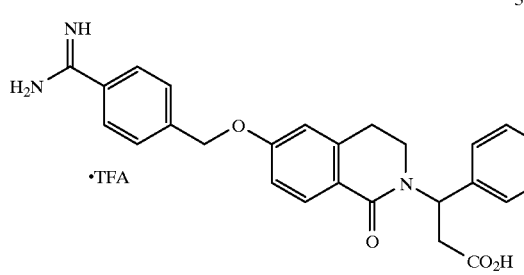

Part A:

The isoquinolone (2) (1.0 g, 3.95 mmol) and 60 wt. % NaH suspended in mineral oil (0.174 g, 4.35 mmol) were refluxed in THF (40 mL) for one hour. The mixture was cooled to room temperature and the alpha-methoxy benzyl chloride (0.683 g. 4.35 mmol) was added in one portion (ref., Liebigs *Ann. Chem.,* 191 (1932). The reaction mixture was stirred overnight at ambient temperature. The mixture was diluted with water (100 mL) and extracted with EtOAc (2×50 mL). The combined extracts were dried over anhydrous sodium sulfate and concentrated. The residue was chromatographed on silica gel eluting with 2:1 hexanes/EtOAc. Obtained 1.02 g of (31g) as a clear oil (68% of theory).

Part B:

Following the procedure employed for the preparation of (32a) (Example 10, part C), (32g) was prepared in 36% yield starting from 2.29 g of (31g).

Part C:

Following the procedure employed for the preparation of (4) (Example 1, part C), (33g) was prepared in 83% yield starting from 1.02 g of (32g).

Part D:

Following the procedure employed for the preparation of (25) (Example 5, part D), (34g) was prepared in 91% yield starting from 0.675 g of (33g).

Part E:

Following the procedure employed for the preparation of (6) (Example 1, part E), (35g) was prepared in 50% yield starting from 0.80 g of (34g).

Part F:

Following the procedure employed for the preparation of (7) (Example I, part F), (36g) was prepared in 79% yield starting from 0.43 g of (35g).

$^1$H NMR (300 MHz, CD$_3$OD): 2.76–3.30 (m, 5H), 3.47–3.54 (m, 1H), 5.27 (s, 2H), 6.38 (t, J=7.4 Hz, 1H), 6.84 (d, J=2.3 Hz, 1H), 6.96 (dd, J=2.3, 8.7 Hz, 1H), 7.28–7.40 (m, 5H), 7.68 (d, J=8.2 Hz, 2H), 7.81 (d, J=8.2 Hz, 2H), 7.91 (d, J=8.7 Hz, 1H). IR (KBr) 3328, 3107, 1671, 1604, 1421, 1278. 1189, 1134, 1020 cm$^{-1}$; MS (FAB) m/e 444.1931 (444.1923 calc'd for C$_{26}$H$_{26}$N$_3$O$_4$).

Example 17

Preparation of 6-[[3-(aminoiminomethyl)phenyl]ethynyl]-3,4-dihydro-1-oxo-2(1H)-isoquinolineacetic acid trifluoroacetate, a compound represented by the formula (12b).

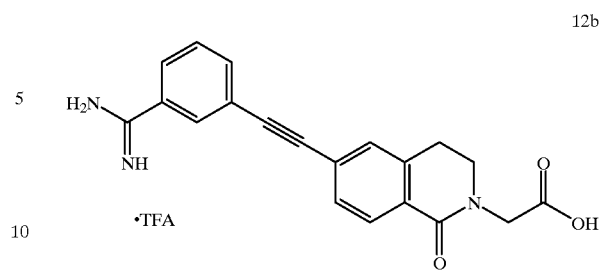

Part A:

Following the procedure employed for the preparation of (10a) (Example 2, part B), (10b) was prepared in 54% yield starting from 0.20 g of (8) (Example 2, part A) and 0.09 g of (9b).

Part B:

Following the procedure employed for the preparation of (6) (Example 1, part E), (11b) was prepared in 10% yield starting from 0.1 g of (9b).

Part C:

Following the procedure employed for the preparation of (7) (Example 1, part f), (12b) was prepared in 87% yield starting from 0.01 g of (11b).

$^1$H NMR (300 MHz, CD$_3$OD) 3.07 (t, J=6.5 Hz, 2H), 3.70 (t, J=6.6 Hz, 2H), 4.31 (s, 2H), 7.46 (s, 1H), 7.50 (d, J=8.2 Hz, 1H), 7.63 (t, J=7.8 Hz, 1H), 7.78 (d, J=7.6 Hz, 1H), 7.88 (d, J=7.7 Hz, 1H), 7.92 (s, 1H), 7.96 (d, J=4.8 Hz, 1H); IR (CHCl$_3$) 3010, 1647, 1607, 1277, 1156 cm$^{-1}$; MS (FAB) m/e 348.1338 (348.1348 calc'd for C$_{20}$H$_{18}$N$_3$O$_3$).

Example 18

Preparation of 6-[2-[3-(aminoiminomethyl)phenyl]ethyl]-3,4-dihydro-1-oxo-2(1H)-isoquinolineacetic acid trifluoroacetate, a compound represented by the formula (15b).

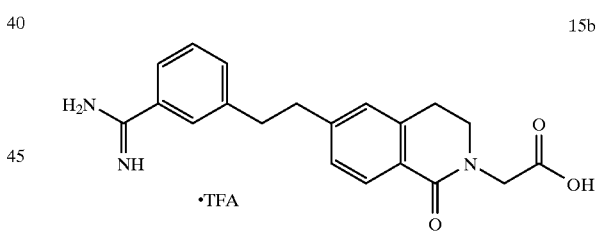

Part A:

Following the procedure employed for the preparation of (13a) (Example 2, part A), (13b) was prepared in 98% yield starting from 0.13 g of (10b).

Part B:

Following the procedure employed for the preparation of (6) (Example 1, part E), (14b) was prepared in 64% yield starting from 0.09 g of (13b).

Part C:

Following the procedure employed for the preparation of (7) (Example 1, part F), (15b) was prepared in 86% yield starting from 0.09 g of (14b).

$^1$H NMR (300 MHz, CD$_3$OD) 3.00 (m, 6H), 3.65 (t, J=6.6 Hz, 2H), 4.28 (s, 2H), 7.09 (s, 1H), 7.13 (d, J=8.2 Hz, 1H), 7.49 (m, 2H), 7.59 (m, 2H), 7.79 (d, J=7.9 Hz, 1H); IR (KBr) 1716, 1679, 1639, 1195, 1134 cm$^{-1}$, S (FD) m/e 352. Anal. Calc'd for C$_{22}$H$_{22}$F$_3$N$_3$O$_5$: 56.77; H, 4.76; N, 9.03; Found: 56.65; H. 4.71; N, 8.73.

Example 19

Preparation of 6-[[(4-aminoiminomethyl)phenyl]methylaminocarbonyl]-3,4-dihydro-1-oxo-2(1H) isoquinoloneacetic acid trifluoroacetate, a compound represented by the formula 50:

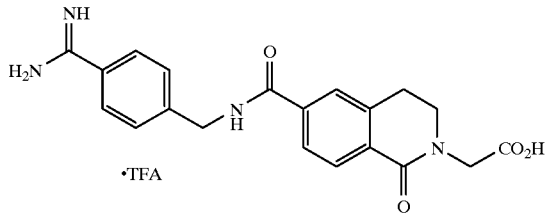

Part A:

A solution of (17) (6-carboxy-3,4-dihydro-1-oxo-2(1H) isoquinoline acetic acid-1,1-dimethylethyl ester) (0.20 g, 0.66 mmol), p-cyano benzylamine (0.10 g, 0.66 mmol), EDCI (0.15 g, 0.8 mmol), and DMAP 10.18 g, 1.4 mmol) in $CH_2Cl_2$ (7.0 mL) was maintained at room temperature for 18 hours and then concentrated. The residue was purified by chromatography (silica gel. 200–400 mesh,. 25:1 $CHCl_3$-MeOH) giving 0.098 g (37%) of 6-[[(4-cyano phenyl)methylamino]carbonyl]-3,4-dihydro-1-oxo-2(1H) isoquinolineacetic acid-1,1-dimethylethyl ester, as a white solid.

Part B:

Following the procedure employed for the preparation of (6) (Example 1, part E), [[4-(1,1-dimethylethoxycarbonylaminoiminomethyl)phenyl]methylaminocarbonyl]-3,4-dihydro-1-oxo-2(1H) isoquinolinacetic acid-1,1-dimethyl ethyl ester was prepared in 38% yield starting from 0.09 g of 6-[[(4-cyanophenyl)methylamino]carbonyl]-3,4-dihydro-1-oxo-2(1H) isoquinolineacetic acid-1,1-dimethylethyl ester.

Part C:

Following the procedure employed for the preparation of (7) (Example 1, part F), 6-[[(4-aminoiminomethyl)phenyl]methylaminocarbonyl]-3,4-dihydro-1-oxo-2(1H) isoquinoloneacetic acid trifluoroacetate was prepared in 83% yield starting from 0.05 g of [[4-(1,1-dimethylethoxycarbonylaminoiminomethyl)phenyl]methylaminocarbonyl]-3,4-dihydro-1-oxo-2(1H) isoquinolinacetic acid-1,1-dimethyl ethyl ester.

$^1$H NMR (300 MHz, $CD_3OD$) 3.14 (t, J=6.4 Hz, 2H), 3.73 (t, J=6.7 Hz, 2H), 4.34 (br s, 2H), 4.68 (d, J=5.9 Hz, 2H), 7.6 (d, J=8.4 Hz, 2H), 7.79 (m, 4H), 8.03 (d, J=8.0 Hz, 1H); IR (KBr) 3327, 3109, 1670, 1639, 1190 cm$^{-1}$; MS (FD) m/e 381.

Example 20

Preparation of 40(+−)-6-[[(4-aminoimidomethyl)phenyl]methoxy]-1,2,3,4-tetrahydronapthylene-2-acetic acid trifluoroacetate, a compound represented by the formula (45):

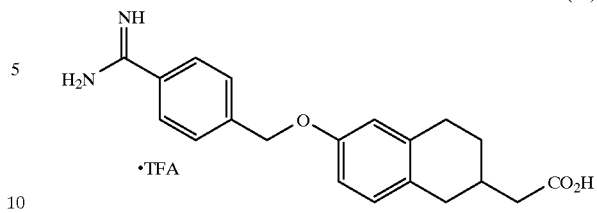

Part A:

A 0° C. slurry of 650 mg (16.3 mmol; 60% dispersion in mineral oil) of NaH in 50 mL THF was treated with 2.70 mL (3.0 g; 13.6 mmol) of triethyl-phosphonoacetate. After stirring at 0° C. for 0.25 hours, a solution of 2.0 g (11.3 mmol) of 6-methoxy-2-tetralone (38) (See, Scheme 6) in 10 mL THF was added dropwise. The cold bath was removed and the reaction stirred at RT for 16 hours. The reaction was quenched by the addition of 50 mL of brine. The two layers were separated and the organic phase dried over $Na_2SO_4$. Evaporation of the solvent gave 3.50 g of a brown oil. Purification by flash chromatography ($SiO_2$; 20% EtOAc in hexanes) afforded 2.10 g (8.52 mmol; 75%) of (39) as a light yellow oil.

Part B:

A solution of 1.00 g (4.06 mmol) of (39) in 20 mL of EtOH was charged with a slurry of 0.2 g of 10% Pd/C in 10 mL EtOH. The mixture was hydrogenated at 50 psi for 3.0 hours at room temperature. The catalyst was filtered off and the reaction evaporated in vacuo to give 1.10 g of an oil. Purification by radial chromatography ($SiO_2$; 5% EtOAc in hexanes) afforded 910 mg (3.66 mmol; 90%) of (40) as a clear oil.

Part C:

A −78° C. solution of 100 mg (0.40 mmol) of (40) in 4 mL $CH_2Cl_2$ was treated with $BBr_3$ (1.0 mL of a 1M solution in $CH_2Cl_2$). The reaction was allowed to reach ambient temperature over 4 hours and was stirred at room temperature for 18 hours. The reaction was cooled to −78° C. and was treated with 5 mL of EtOH. The mixture was allowed to warm and was stirred at room temperature for 3 hours. The volatiles were evaporated in vacuo and the residue dissolved in 5 mL of EtOH and the mixture stirred for 2 hours. Evaporation of the EtOH gave a brown oil which was reconstituted in 20 mL of EtOH and the solution was treated with a stream of HCl (g) for 10 minutes. The reaction was capped and was stirred at room temperature for 16 hours. Concentration in vacuo gave 61 mg of phenol (41). The material was taken up in 2 mL of DMF and was treated with 41 mg (0.30 mmol) of $K_2CO_3$, 8 mg (0.05 mmol) NaI and 57 mg (0.29 mmol) of alpha-bromo-p-tolunitrile. The reaction was stirred at room temperature for 16 hours and the DMF removed in vacuo. The residue was partitioned between 10 mL $H_2O$ and 10 mL EtOAc. The organic layer was separated, was washed with 10 mL $H_2O$, and was dried over $Na_2SO_4$. Evaporation of the solvent in vacuo afforded 91 mg of a solid. Purification of the solid by radial chromatography ($SiO_2$; 25% EtOAc in hexanes) gave 82 mg (0.24 mmol; 60% from (40)) of (42) as a white solid.

Part D:

Following the procedure employed for the preparation of (6) (Example 1, part E), (43) was prepared in 50% yield starting from 0.429 g of (42).

Part E:

A solution of 250 mg (0.54 mmol) of (43) in 5 mL of EtOH was treated with 0.5 mL of 5N aq NaOH (2.5 mmol). The reaction was stirred at room temperature for 6 hours at which time 3.0 mL of 1N aq citric acid (3.0 mmol) was added. The EtOH was evaporated in vacuo. The white solid was filtered, was washed with $H_2O$, and was dried in vacuo to afford 130 mg of acid 44) as a white powder. The solid was slurried in 1 mL of anisole and the mixture treated with 10 mL of trifluoroacetic acid. The reaction was stirred at room temperature for 3 hours and was evaporated in vacuo. The residue was slurried in 10 mL $H_2O$ and the mixture extracted with hexanes (5×5 mL). The aqueous layer was lyopholized to afford 96 mg (0.26 mmol; 48% from (43)) of the trifluoroacetate salt of (45) as a white solid. MS (FD), m/e 339 (M+1, 100). IR (KBr) 3301, 3145, 2915, 1711, 1664, 1503, 1437, 1196, 1143, 1057 $cm^{-1}$. Analytical Calculated for $C_{27}H_{34}N_2O_5 \cdot 1.5\ H_2O$: C 55.11, H 5.47, N 5.84; Found C 55.46, H 5.15, N 5.45.

Example 21

Preparation of 6-[[4-(guanidinomethyl)phenyl]methoxy]-3,4-dihydro-1-oxo-2(1H)-isoquinoloneacetic acid trifluoroacetate, a compound represented by the formula:

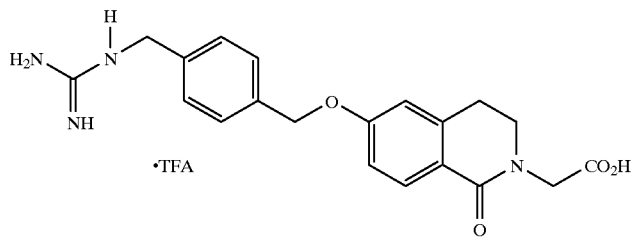

Part A:

A mixture of (4) and (51) (prepared from the dibromide and potassium pthalimide using standard protocols), $K_2CO_3$, and DMF was maintained at 80° C. for 4 hours and then allowed to cool to room temperature. The reaction mixture was diluted with EtOAc and washed with $H_2O$. The organic material was concentrated and the crude isolate was purified on silica giving (46) as a clear oil.

Part B:

A mixture of hydrazine hydrate (0.079 mL, of an 85% solution in $H_2O$, 1.4 mmol), (46) (0.075 g, 0.14 mmol), and EtOH (3 mL) was maintained at 60° C. for 1 hour and then allowed to cool to room temperature. The reaction mixture was diluted with EtOAc and washed with aqueous $NaHCO_3$. The organic material was concentrated giving 0.055 g (100%) of (47) as a clear oil.

Part C:

A mixture of (47) (0.049 g, 0.12 mmol), N,N'-bis(tert-butoxycarbonyl)-S-methylisothiourea (0.043 g, 0.15 mmol) and THF (1 mL) was maintained at room temperature for 60 hours and then concentrated. Chromatography (2:1 hexanes/EtOAc) gave 0.073 g (90%) of (49) as a clear oil.

Part D:

Following the procedure employed for the preparation of (7) (Example 1 part F), (50) was prepared in 78% yield starting from 0.07 g of (49).

$^1$H NMR (300 MHz, $CD_3OD$) 3.05 (bt, 2H), 3.65 (bt, 2H), 4.28 (s, 2H), 5.20 (s, 2H), 6.90 (m, 2H), 7.35 (d, 2H), 7.50 (d, 2H), 7.85 (d, 2H); IR (KBr) 3364, 3199, 1736, 1687, 1633, 1609, 1179 $cm^{-1}$; MS (FAB) m/e 383.1732 (383.1717 calcd for $C_{20}H_{23}N_4O_2$).

Example 22

Preparation of 6-[4-(piperidn-4-yl)propyloxy]-3,4-dihydro-1-oxo-B-(3-ethoxypropyl)-1-oxo-2(1H)-isoquinolinepropanoic acid trifluoroacetate, a compound represented by the formula:

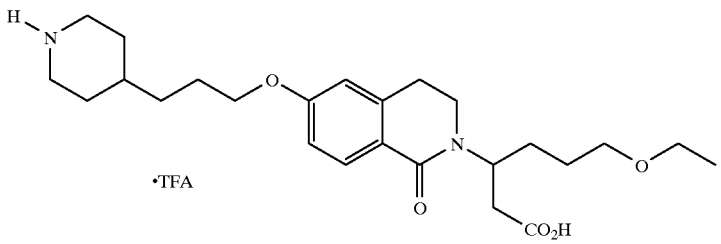

Part A:

A solution of (33a) (0.053 g, 0.14 mmol) and alcohol (51) (prepared from 3-(4-pyridyl)-propanol using standard protocols), triphenyl phosphine (0.046 g, 0.17 mmol), diethyl azodicarboxylate (0.028 mL, 0.17 mmol) in THF (1.3 mL) was maintained at room temperature for 1 hour and then concentrated. The crude residue was purified by chromatography (1:1 hexanes/EtOAC) giving 0.047 g (61%) of 52 as a clear oil.

Part B:

Following the procedure employed for the preparation of (7) (Example 1 part F), (53) was prepared in 95% yield starting from 0.042 g of (52).

$^1$H NMR (300 MHz, CD$_3$OD) 1.13 (t, J=7.0 Hz, 3H), 1.27–1.98 (m 15H), 2.58 (m, 2H), 2.96 (m, 4H), 3.28–3.51 (m, 6H), 4.02 (t, J=6.1 Hz, 2H), 5.05 (m, 1H), 6.75 (br s, 1H), 6.83 (d, J=8.7 Hz, 1H), 7.82 (d, J=8.6 Hz, 1H); MS (FAB) m/e 447. Anal. Calcd for C$_{27}$H$_{39}$N$_2$O$_7$: C, 57.85; H, 7.01; N, 5.00. Found: C, 58.13, H, 7.18; N, 5.28.

Example 23

Preparation of the compound represented by the formula 66:

Part A:

A solution of DIBAH in toluene (100 mL of a 1.5M solution, 150 mmol) and 6-methoxy-2-tetralone (60) (5.19 g, 28 mmol) was maintained at reflux for 17 hours and then cooled to 0° C. This mixture was quenched by slow addition of saturated aqueous NH$_4$Cl (25 mL) followed by 1N HCl (25 mL) and allowed to slowly warm to room temperature with stirring. The resulting gelatinous mixture was filtered through Celite and the colorless aqueous filtrate extracted with EtOAc. The combined extracts were washed with 1N HCl, H$_2$O, and brine, dried (MgSO$_4$), and concentrated in vacuo. The crude material was purified by chromatography (silica gel 230–400 mesh, toluene:EtOAc gradient) to afford 1.75 g (38%) of 62 as a can solid.

Part B:

To a solution of 62 (1.64 g, 10 mmol) in DMF (40 mL) at –5° C. was slowly added benzyltrimethylammonium hydroxide (Triton B, 4.5 mL, 10 mmol). After stirring 0.75 hours, α-bromo-p-tolunitrile (1.98 g, 10 mmol) was added as a solid and the solution was allowed to warm to room temperature gradually overnight. The mixture was diluted with EtOAc, washed with H$_2$O, 1N HCl, saturated NaHCO$_3$, and brine, dried (MgSO$_4$), and concentrated in vacuo. The crude material was purified by chromatography (silica gel 230–400 mesh, toluene:EtOAc gradient) to afford 2.05 g (73%) of 63 as a white solid.

Part C:

To a rapidly stirred mixture of 63 (2.0 g, 7.16 mmol), KOH (50% w/v aqueous, 20 mL), and tetrabutylammonium hydrogen sulfate (1.25 g, 3.58 mmol) in benzene (30 mL) was added neat tert-butyl bromoacetate (3.51 mL, 21.72 mmol) dropwise. The mixture was stirred at room temperature for 3 hours then diluted with EtOAc and washed with 1N HCl, saturated NaHCO$_3$, H$_2$O, and brine, dried (MgSO$_4$), and concentrated in vacuo. The crude material was purified by chromatography (silica gel 230–400 mesh, toluene:EtOAc gradient) to afford 2.38 g (85%) of 64 as a white solid.

Part D:

Following the general procedure outlined for the preparation of 6 (Example 1 part E), 65 was prepared in 63% yield starting from 2.33 g of 64.

Part E:

Following the general procedure outlined for the preparation of 7 (Example 1 part F), 66 was prepared in 98% yield starting from 1.78 g of 65. MS (FD) m/e 355.

Example 24

Preparation of the compound represented by the formula 69:

Part A:

To a solution of 62 (0.64, 3.9 mmol) in DMF (25 mL) at –5° C. was slowly added benzyltrimethylammonium hydroxide (Triton B, 1.77 mL, 3.9 mmol). After stirring 0.5 h, 1-tBOC-4-(3-bromopropyl)piperidine (1.19 g, 3.9 mmol) was added neat and the solution was allowed to warm to room temperature gradually overnight. Diluted the mixture with EtOAc, washed with H$_2$O, 1N HCl, saturated NaHCO$_3$, and brine, dried (MgSO$_4$), and concentrated in vacuo. The crude material was purified by chromatography (silica gel 230–400 mesh, toluene:EtOAc gradient) to afford 1.37 g (90%) of 67 as a colorless gum.

Part B:

To a rapidly stirred mixture of 67 (1.32 g, 3.4 mmol), KOH (50% w/v aqueous, 10 mL), and tetrabutylammonium hydrogen sulfate (0.6 g, 1.7 mmol) n benzene (15 mL) was added neat tert-butyl bromoacetate (0.61 mL, 3.74 mmol) dropwise. The mixture was stirred at room temperature for 3 hours then diluted with EtOAc and washed with 1N HCl, H$_2$O, and brine, dried (MgSO$_4$), and concentrated in vacuo. The crude material was purified by chromatography (silica gel 230–400 mesh, toluene:EtOAc gradient) to afford 1.56 g (91%) of 68 as a pale yellow oil.

Part C:

A mixture of 68 (1.51 g, 3 mmol) and TFA (15 mL) was stirred at room temperature for 2 hours and then concentrated in vacuo. To the resulting oil was added Et$_2$O/hexane and upon sonnication a solid was obtained. The material was filtered, washed with Et$_2$O and dried to afford 1 g (77%) of 69 as a tan solid. MS (FD) m/e 348.

Example 25

Preparation of the compound represented by the formula 72:

(72)

Part A:
To a solution of DMSO (0.26 mL, 3.6 mmol) in CH$_2$Cl$_2$ (13 mL) cooled to −78° C. was added neat trifluoroacetic anhydride (0.51 mL, 3.6 mmol) dropwise. The colorless solution was stirred for 0.25 hours at −78° C. then 67 (0.7 g, 1.8 mol) in CH$_2$Cl$_2$ (12 mL) was added dropwise over 5 min. The solution was stirred 1 hour at −78° C. then allowed to warm to room temperature and stirred another 1.5 hours. Diisopropylethylamine (0.72 mL, 4.14 mmol) was added neat and room temperature stirring continued for 1.5 hours. The solution was diluted with CH$_2$Cl$_2$ (59 mL) and washed with 1N HCl, saturated NaHCO$_3$, H$_2$O, and brine, dried (MgSO$_4$), and concentrated to afford ~0.7 g (>99%) of 70 as a colorless oil that was used immediately in the next step without further purification.

Part B:
A mixture of 70 (0.70 g, 1.8 mmol), NaBH$_3$CN (0.12 g, 1.8 mmol), glycine t-butyl ester (0.47 g, 3.6 mmol), glacial HOAc (0.1 mL, 1.8 mmol), and powdered 3A molecular sieves (0.4 g) in absolute EtOH (20 mL) was allowed to stir at room temperature for 17 hours. The mixture was filtered, the filtrate concentrated, and the resulting oil redissolved in EtOAc/H$_2$O and adjusted to pH 7.4 with 1N NaOH. The layers were separated, and the aqueous layer extracted with EtOAc. The EtOAc extracts were combined and washed with saturated NaHCO$_3$, H$_2$O, and brine, dried (Na$_2$SO$_4$), and concentrated. The crude isolate was purified by chromatography (silica gel 230–400 mesh, toluene:EtOAc gradient) to afford 0.17 g (19%) of 71 as a colorless gum.

Part C:
A mixture of 71 (0.2 g, 0.4 mmol) and TFA (10 mL) was stirred at room temperature for 3 hours and then concentrated in vacuo. To the resulting oil was added Et$_2$O slowly and upon sonication a solid was obtained. The material was filtered, washed with Et$_2$O and dried to afford 0.2 g (87%) of 72 as a tan solid. MS (FD) m/e 347.

Example 26

Preparation of the compound represented by the formula 78:

(78)

Part A:
To a solution of DMSO (0.28 mL, 4 mmol) in CH$_2$Cl$_2$ (13 mL) cooled to −78° C. was added neat trifluoroacetic anhydride (0.56 mL, 4 mmol) dropwise. The turbid white solution was stirred for 0.25 hours at −78° C. then 63 (0.558 g, 2 mmol) in CH$_2$Cl$_2$ (12 mL) was added dropwise over 5 min. The solution was stirred 1 hour at −78° C. then allowed to warm to room temperature and stirred another 1.5 hours. Diisopropylethylamine (0.8 mL, 4.6 mmol) was added neat and room temperature stirring continued for 1 hour. The solution was diluted with CH$_2$Cl$_2$ (50 mL) and washed with 1N HCl, saturated NaHCO$_3$, H$_2$O, and brine, dried (MgSO$_4$), and concentrated to afford 0.55 g (>99%) of 73 as a light yellow solid that was used immediately in the next step without further purification.

Part B:
A mixture of 73 (0.55 g, 2 mmol), NaBH$_3$CN (0.13 g, 2 mmol), glycine t-butyl ester (0.52 g, 4 mmol), glacial HOAc (0.11 mL, 2 mmol), and powdered 3A molecular sieves (0.4 g) in absolute EtOH (25 mL) was allowed to stir at room temperature for 17 hours. The mixture was filtered, the filtrate concentrated, and the resulting gum redissolved in EtOAc/H$_2$O and adjusted to pH 7.5 with 1N NaOH. The layers were separated, and the aqueous layer extracted with EtOAc. The combined EtOAc extracts were washed with saturated NaHCO$_3$, H$_2$O, and brine, dried (Na$_2$SO$_4$), and concentrated to afford ~0.8 g (99%) of 74 as a colorless gum without further purification.

Part C:
A mixture of 74 (0.784 g, 2 mmol), K$_2$CO$_3$ (0.829 g, 6 mmol), and BOC$_2$O (0.873 g, 4 mmol) in THF/H$_2$O (1:1, 20 mL) was stirred at room temperature for 5 hours. The THF was evaporated in vacuo and the aqueous residue diluted with brine (50 mL) and extracted with EtOAc. The combined extracts were washed with brine, dried (MgSO$_4$), and concentrated. The crude material was purified by chromatography (silica gel 230–400 mesh, toluene:EtOAc gradient) to afford 0.74 g (75%) of 76 as a pale yellow solid.

Part D:
Following the general procedure employed for the preparation of 6 (Example 1 part E), 77 was prepared in 31% yield starting from 0.66 g of 76.

Part E:
Following the general procedure employed for the preparation of 7 (Example 1 part F), 78 was prepared in 81% yield starting from 0.22 g of 77. MS (FD) m/e 354.

Example 27

Preparation of the compound represented by the formula 80:

(80)

Part A:
Compound 74 was dissolved (1.96 g, 5 mmol) in CH$_2$Cl$_2$ (20 mL), pyridine was added (2 mL, 26 mmol), followed by dropwise addition of neat acetic anhydride (0.47 mL, 5 mmol). The gold solution was stirred at room temperature for 6 hours, then concentrated and the resulting oil redissolved in EtOAc, washed with 1N HCl, H$_2$O, and brine, dried (MgSO$_4$), and concentrated. The crude material was purified by chromatography (silica gel 230–400 mesh, toluene:EtOAc gradient) to afford 0.86 g (39%) of 75 as a white solid.

Part B:

Following the general procedure employed for the preparation of 6 (Example 1 part E), 79 was prepared in 81% yield starting from 1.19 g of 75.

Part C:

Following the general procedure employed for the preparation of 7 (Example 1 part F), 80 was prepared in 92% yield starting from 0.96 g of 79. MS (FD) m/e 396.

Example 28

Preparation of the compound represented by the formula 88:

(88)

Part A:

A mixture of 81 (3.9 g, 13.3 mmol) and EtOH (20 mL) was treated with NaBH$_4$ (1.0 g, 26.6). The mixture was maintained at reflux for 1 hour and then allowed to cool. The reaction mixture was then diluted with EtOAc and washed with H$_2$O. The organic material was concentrated and the residue thus obtained was subjected to dehydration with TsOH (cat) in refluxing benzene. The crude dehydration mixture was diluted with EtOAc and washed with H$_2$O. The organic material was concentrated and the crude residue purified by chromatography (5:1 hexane/EtOAc) giving 2.6 g of 82.

Part B:

A mixture of 82 (2.6 g, 9.5 mmol), NMO (1.53 g, 11.3 mmol), tBuOH (8 mL), H$_2$O (8 mL), and acetone (8 mL) was treated with OsO$_4$ (0.1 mL of a 1 mg/mL solution in CCl$_4$) and the resulting mixture stirred at room temperature overnight. The mixture was then diluted with EtOAc and washed with H$_2$O and saturated aqueous NaHCO$_3$. The organic material was then concentrated. The crude residue was recrystallized from EtOAc/hexane giving 2.8 g of 83 as a white solid.

Part C:

Diol 83 (2.8 g) was suspended in benzene and TsOH (0.1 g) was added. This mixture was then maintained at reflux for 15 min. The solution was then diluted with EtOAc and washed 0.1N aqueous NaOH. The organic material was then concentrated. The crude residue was taken up in THF (25 mL) and the resulting solution was added to a mixture of NaH (0.5 g of a 60% dispersion in oil, 14.7 mmol), triethylphosphonoacetate (3.3 g, 14.7 mmol) and THF (25 mL) at 0° C. The resulting mixture was allowed to warm to room temperature and after three hours it was diluted with EtOAc and washed with H$_2$O. The organic material was concentrated and the crude isolate was purified on silica (3:1 hexane/EtOAc) giving 2.52 g of 84 as a clear oil.

Part D:

A mixture of 84 (2.51 g, 6.87 mmol) Pd/C (10% on carbon, 2.5 g) and EtOH (20 mL) was maintained under H$_2$ (balloon) for 2 hours and then filtered and concentrated. The residue was dissolved in CH$_2$Cl$_2$ (5 mL) and treated with p-cyanobenzoic acid (1.21 g, 8.3 mmol), EDCI (1.6 g, 8.3 mmol), and DMAP (cat). The resulting solution was allowed to stir for 4 hours and then it was diluted with EtOAc and washed with H$_2$O. The organic material was concentrated and the resulting solid material was crystallized from (EtOAc)/hexane) giving 1.35 g (54%) of 86 as a white solid.

Part E:

Following the general procedure outlined for the preparation of 6 (Example 1 part E), 87 was prepared in 80% yield starting from 1.35 g of 86.

Part F:

Following the general procedure outlined for the preparation of 7 (Example 1 part F), 88 was prepared in 70% yield starting from 0.2 g of 87.

$^1$H NMR (300 MHz CD$_3$OD) 1.5 (m, 1H), 2.0 (m, 1H), 2.2 (m, 1H), 2.4 m, 2H) 2.45 (dd, J=10.2, 16.2 Hz, 1H), 2.91 (m, 3H), 7.05 (d, J 8.2 Hz, 1H), 7.40 (m, 2H), 7.92 (d, J=8.4 Hz, 2H), 3.12 (d, J=8.4 Hz, 2H); IR (KBr) 3322, 3104, 1712, 1667, 1207 cm$^{-1}$; MS (FAB) m/e 352.1661 (352.1654 calcd for C$_{20}$H$_{22}$N$_3$O$_3$).

Example 29

Preparation of the compound represented by the formula 95:

(95)

Part A:

A mixture of 82 and NaH in THF was treated with benzylbromide and Bu$_4$NI (cat.) and the resulting solution was allowed to stand at room temperature for 2 hours. The solution was then diluted with EtOAc and washed with H$_2$O. The organic material was concentrated giving essentially pure 88 as a yellow oil.

Part B:

A mixture of 88 (1.0 g, 2.71 mmol), NMO (0.40 g, 3.0 mmol), t-BuOH (2.0 mL) acetone (2.0 mL) , and H$_2$O (2 mL) were treated with OsO$_4$ (0.1 mL of a 1 mg/mL solution in CCl$_4$) and the resulting solution allowed to stand overnight. The mixture was then diluted with EtOAc and washed with saturated aquous NaHCO$_3$ and H$_2$O. The organic material was concentrated and the crude residue taken up in benzene (25 mL) and treated with TsOH (cat.). The resulting mixture was maintained at reflux for 15 minutes and then concentrated. The crude isolate was taken up in EtOH and treated with NaBH$_4$ (0.25 g) and allowed to stand for 1 hour. This mixture was diluted with EtOAc and washed with H$_2$O. The organic material was concentrated and the crude isolate was purified by chromatography (1:1 hexanes/EtOAc) giving 0.19 g of 90 as a clear oil.

Part C:

A mixture of 90 (0.18 g, 0.64 mmol), and t-butyl bromoacetate (0.18 , 0.95 mmol) benzene (5 mL), 50% of NaOH (5 mL), and Bu$_4$NHSO$_4$ (cat.) was vigorously stirred at room temperature for 12 hours. This mixture was then diluted with EtOAc and washed with H$_2$O. The organic material was concentrated and the crude isolate purified by chromatography (5:1 hexanes/EtOAc) yielding 0.09 g (35%) of 91 as a clear oil.

Part D:

A mixture of 91 (0.31 g) and 10% Pd/C (0.3 g) in EtoAc was maintained in an atmosphere of H$_2$ (balloon) for 4 hours and then filtered and the filtrate concentrated. The crude residue was taken up in CH$_2$Cl$_2$ (5 mL) and was treated with p-cyanobenzoic acid (0.12 g, 0.70 mmol), EDCI (0.23 g, 0.79 mmol), and DMAP (cat). The resulting solution was maintained at room temperature for 2 hours and then diluted with EtOAc and washed with H$_2$O. The organic material was concentrated and the crude residue purified on silica (3:1 hexanes/EtOAc) giving 0.24 g of 93 as a clear oil.

Part E:

Following the general procedure employed for the preparation of 6 (Example 1 part E), 94 was prepared in 56% yield starting from 0.23 g of 93.

Part F:

Following the general procedure employed for the preparation of 7 (Example 1 part F), 95 was prepared in 63% yield starting from 0.16 g of 94.

$^1$H NMR (300 MHz CD$_3$OD) 1.90 (m, 1H), 2.05 (m, 1H), 2.7–3.3 (m, 4H) 3.90 (m 1H), 4.20 (s, 2H), 7.10 (d, J=8.0 Hz, 1H), 7.40 (m, 2H), 7.90 (d, J=8.3 Hz, 2H), 8.15 (d, J=8.3 Hz, 2H); IR (KBr) 3326, 2936, 1664, 1598 cm$^{-1}$; MS (FAB) m/e 368 Anal. Calcd. for C$_{22}$H$_{22}$N$_3$O$_6$F$_3$: C, 54.89; H, 4.61; N, 8.73. Found: C, 54.90; H, 4.67; N, 8.50.

Example 30

Preparation of the compound represented by the formula 102:

(102)

Part A:

A mixture of tetralone 96 (5.0 grams, 24.6 mmol), glyoxylic acid monohydrate (8.4 g, 93.6 mmol), NaOH (4.35 g. 108.9 mmol), methanol (50 mL) and H$_2$O (50 mL) was maintained at reflux for 1.25 hours and then chilled to 0° C. The reaction was then acidified (with stirring) with concentrated HCl. The formed ppt (97) (5.8 g) was collected by filtration.

Part B:

A mixture of 97 (20.0 g, 77.2 mmol) and Zn (14.1 g, 216 mmol) in HOAc (160 mL) and H$_2$O (60 mL) was maintained at reflux for 1.25 hours and then filtered. The filtrate was diluted when H$_2$O and the resulting mixture extracted with EtOAc. The combined extracts were concentrated. The crude isolate was taken up in concentrated HCl (100 mL) and maintained at reflux for 0.5 hours. The mixture was then diluted with H$_2$O (300 mL) and cooled to 5° C. The mixture was carefully neutralized to a pH 4 by the addition of solid Na$_2$CO$_3$. The formed ppt was collected by filtration and dried in vac. This material was then suspended in EtOH and the resulting solution was saturated with HCl(g). The mixture was then concentrated. The material thus formed was suspended in H$_2$O and the pH of the resulting solution was adjusted to pH 10 with solid NaOH. This material was extracted with EtOAc and the extracts concentrated. The crude product was recrystallized from EtOAc/Hexanes giving 12.1 grams of pure 98 as a tan solid.

Part C:

A mixture of 98 (6.8 g, 27.5 mmol), p-cyanobenzoic acid (4.4 g, 30.2 mmol), EDCI (7.86 g, 41.2 mmol), DMAP (0.1 g), and CH$_2$Cl$_2$ (10 mL) was stirred at room temperature for 4 hours. This mixture was then diluted with EtOAc and washed with H$_2$O. The organic material was then concentrated affording crude 99 as a tan solid. Recrystallization from EtOAc/hexanes gave 7.86 g of pure 99.

Part D:

Following the general procedure outlined for the preparation of 6 (Example 1 part E), 100 was obtained in 74% yield starting from 7.85 g of 99.

Part E:

Following the general procedure outlined for the preparation of 7 (Example 1 part F), 101 was obtained in 90% yield starting from 5.0 g of 100.

Part F:

A mixture of 100 (2.0 g, 4.1 mmol) and EtOH (5 mL) was treated with NaOH (0.49 g, 12.1 mmol) and the resulting solution was maintained at room temperature for 2 hours. The solution was then concentrated and the resulting residue taken up in H$_2$O. The aqueous material was washed once with EtOAc and then carefully acidified (pH 4) with KHSO$_4$. The formed precipitate was collected by filtration and dried in-vacuo. This material was then treated with TFA (10 mL) for one hour and then concentrated. The crude material was taken up in hot H$_2$O, filtered, and then lyopholized giving pure 102 as a white powder.

$^1$H NMR (300 MHz CD$_3$OD) 2.0 (m, 1H), 2.25 (m, 1H), 2.50 (dd, J=6.4, 16.4 Hz, 1H), 2.90 (dd, J=4.2, 16.5 Hz, 1H) 2.90–3.2 (m, 3H) 7.6 (dd J=1.9, 8.6 Hz, 1H), 7.80 (s, 1H), 7.95 (m, 3H), 8.14 (d, J=8.3 Hz, 2H); IR (KBr) 3330, 3108, 1712, 1669, 1538 cm$^{-1}$; MS (FAB) 366. Anal. Calcd. for C$_{22}$H$_{20}$N$_3$O$_6$F$_3$: C, 55.12; H, 4.20; N, 8.76. Found: C, 54.88; H, 4.31; N, 8.46.

Example 31

Preparation of the compound represented by the formula 118:

(118)

Part A:

A mixture of 100 (0.2 g, 0.4 mmol) and EtOH (10 mL) was treated with NaBH$_4$ (0.025 g, 0.4 mmol) and allowed to stand at room temperature for 1 hour. This mixture was then concentrated and the residue dissolved in EtOAc. This mixture was washed with H$_2$O and concentrated. The crude residue was taken up in THF (15 mL) and treated with TsOH (cat.). The resulting solution was maintained at reflux for 1.5 hours. This mixture was concentrated and the residue taken up in EtOAc and the resulting solution was washed with 0.1N NaOH and then concentrated. Chromatography (1:1 hexanes/EtOAc) gave 0.08 g of pure 116 as a white solid.

Part B:

Following the general procedure outlined for the preparation of 102 (Example 30 part F), 118 was obtained in 80% yield starting from 0.08 g of 116.

$^1$H NMR (300 MHz CD$_3$OD) 2.34 (br t, J=8.0 Hz, 2 H), 2.83 (br t, J=8.0 Hz, 2H), 3.28 (s, 2H), 6.40 (s, 1H), 7.0 (d, J=8.7 Hz, 1H), 7.5 (m, 2H), 7.92 (d, J=8.3 Hz, 2H), 8.10 (d, J=2H); IR (KBr) 3385, 3089, 1716, 1672, 1194 cm$^{-1}$; MS (FAB) m/e 350.1505 (350.1505 calcd. for C$_{20}$H$_{20}$N$_3$O$_3$).

Example 32

Preparation of the compound represented by the formula 123:

(123)

Part A:

A mixture of 98 (0.14 g, 0.58 mmol) acid 119 (0.095 g, 0.58 mmol), EDCI (0.16 g, 0.86 mmol), DMAP (cat), and CH$_2$Cl$_2$ (3 mL) was maintained at room temperature overnight. The mixture was then diluted with EtOAc and washed with H$_2$O. The organic material was concentrated and the crude residue purified on silica (hexanes/EtOAc 2:1) giving 0.095 g (40%) of 120.

Part B:

Following the general procedure described for the preparation of 6 (Example 1 part E), 121 was prepared in 37% yield starting from 0.95 g of 120.

Part C:

A mixture of 121 (0.04 g, 0.08 mmol), NaOH (0.003 g, 0.08 mmol) and EtOH (5 mL) was maintained at room temperature for 6 hours and then concentrated. The residue was dissolved in H$_2$O and acidified to pH 4 with KHSO$_4$. The resulting mixture was extracted with EtOAc and the extracts were concentrated. Chromatography (EtOAc) gave 0.014 g of 122. Treatment of this material with TFA (5 mL) for 1 hour followed by concentration gave 0.014 g of 123.

$^1$H NMR (300 MHz CD$_3$OD) 2.0 (ddd, J=4.5, 13.0, 25.8 Hz, 1H), 2.30 (m, 1H), 2.45 (dd, J=6.4, 16.5 Hz, 1H), 2.90 (dd, J=5.7, 16.5 Hz, 1H), 2.9–3.2 (m, 3H), 7.6 (m, 1H), 7.75 (m, 3H), 7.95 (m, 2H); IR (KBr) 3341, 3118, 1664, 1205 cm$^{-1}$; MS (FAB) m/e 384.

Example 33

Preparation of the compound represented by the formula 130:

(130)

Part A:

A mixture of 2-bromo,6-benzyloxynapthylene (124) (1.0 g, 3.2 mmol) and THF (25 mL) was created with t-BuLi (4.2 mL of a 1.7M solution in pentane, 7.0 mmol) at −78° C. After 1 hour, diethyl oxalate (0.5 mL, 3.5 mmol) was added and the resulting mixture was allowed to warm to room temperature. The reaction mixture was then diluted with EtOAc and washed with H$_2$O. The organic layer was concentrated. The crude material was purified by chromatography (3:1 hexane/EtOAc) giving 0.52 g of pure 125.

Part B:

A mixture of 125 (7.0 g, 6.0 mmol) and EtOH (50 mL) was treated with NaBH$_4$ (0.12 g, 6.0 mmol) and allowed to stir for 1 hour. The mixture was then diluted with EtOAc and washed with 1N HCl. The organic material was then concentrated. The crude material was taken up in pyridine (10 mL) and treated with Ac$_2$O (10 mL). After 1 hour, the solution was concentrated to dryness and the residue was passed through a plug of silica (4:1 hexane/EtOAc). The material thus obtained was subjected to catalytic hydrogenation employing 10% Pd/C (balloon). After removal of the catalyst by filtration and concentration one obtains 0.48 g (35%) of the desired compound 126.

Part C:

A mixture of 126 (0.48 g, 2.1 mmol), α-bromo-p-tolunitrile (0.45 g, 2.3 mmol), K$_2$CO$_3$ (0.32 g, 2.3 mmol), BU$_4$NI (cat), and DMF (5 mL) was maintained at 80° for 4 hours and then allowed to cool to room temperature. This solution was diluted with EtOAc and the resulting solution was washed with H$_2$O. The organic material was then concentrated. The crude residue was recrystallized from EtoAc/Hexanes giving 0.33 g (45%) of 127 as a tan solid.

Part D:

Following the general procedure outlined for the preparation of 6 (Example 1 part E), 128 was obtained in 50% yield starting from 0.33 g of 127.

Part E:

A mixture of 128 (0.10 g, 0.22 mmol), EtOH (5 mL), and aqueous NaOH (0.22 mL of a 2N solution, 0.44 mmol) was stirred at room temperature for 5 hours and then concentrated. The residue was taken up in H$_2$O and the resulting solution was extracted with EtOAc. The pH of the aqueous material was then adjusted to pH 4 with HCl (1N) and the resulting mixture extracted with EtOAc. The extracts were concentrated and the crude material was treated with TFA (10 mL) for 1 hour at room temperature. The reaction mixture was then concentrated to dryness affording 0.07 g of 130 as a white solid.

$^1$H NMR (300 MHz CD$_3$OD) 3.85 (S, 2 H), 5.2 (S, 2H), 7.2–7.4 (m, 3H), 7.6–7.9 (m, 7H); IR (KBr) 3334, 3106, 1695, 1669, 1130 cm$^{-1}$; MS (FAB) m/e 335. Anal. Calcd. for C$_{22}$H$_{19}$N$_2$O$_5$F$_3$: C, 58.93; H, 4.27; N, 6.25. Found: C, 58.70, H, 4.46; N, 5.97.

Example 34

Preparation of the compound represented by the formula:

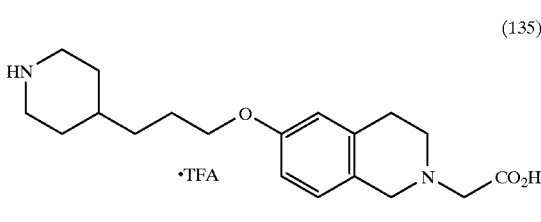

(135)

Part A:

A mixture of 2 (0.5 g, 2.0 mmol) and THF (10 mL) was treated with LiAlH$_4$ (0.15 g, 4.0 mmol) and then maintained at reflux for 2 hours. The mixture was allowed to cool to room temperature and then quenched with H$_2$O and 15% NaOH. The resulting mixture was filtered and concentrated. This procedure allowed the isolation of 0.45 g of material whose purity was sufficient for the next transformation. A portion of this material (0.25 g, 1.1 mmol), K$_2$CO$_3$ (0.16 g, 1.17 mmol) tert-butyl bromoacetate (0.25 g, 1.17 mmol), and CH$_3$CN (5 mL) was stirred at room temperature for 15 hours. The mixture was then diluted with EtOAc and washed with H$_2$O. The organic material was concentrated and the crude residue purified on silica (2.5:1 hexanes/EtOAc) giving 0.34 g (90%) of 132.

Part C:

A mixture of 132 (0.1 g, 0.28 mmol) (Pd/C (10% on carbon 0.1 g), and EtOAc was maintained under an atmosphere of H$_2$ for 12 hours and then filtered and concentrated. Chromatography, (1.5:1 hexanes/EtOAc) gave 0.039 g (52%) of 133.

Part D:

A mixture of 133 (0.073 g, 0.28 mmol), NaH (0.012 g of a 60% dispersion in oil, 0.31 mmol) in THF (10 mL) was stirred at room temperature for ½ hour and then treated with a solution of 1-tBOC-4-(3-bromopropyl)piperidine (0.093, 0.31 mmol) in THF (1 mL). The resulting solution was maintained at reflux for 2 hours and then allowed to cool to room temperature. The reaction mixture was diluted with EtOAc and washed with H$_2$O. The organic material was concentrated and the resulting material was chromatographed on silica (3:1 hex/EtOAc) giving 0.086 g of alkylated product. This material (0.076 g) was dissolved in TFA (5 mL) and maintained at room temperature for 1 hour. This material was then concentrated. The crude residue was taken up in 10% HCl (5 mL) and lyophilized giving 0.51 g of 135 as a white powder.

$^1$H NMR (300 MHz CD$_3$OD) 1.30–1.58 (m, 4H), 1.60–1.75 (m, 1H), 1.85 (m, 2H), 1.95 (m, 2H), 3.0 (m, 2H), 3.2 (m, 2H), 3.4 (m, 2H), 3.65 (brs, 2H), 4.0 (t, J=6.2 Hz, 2H), 4.18 (s, 2H), 4/45 (s, 2H), 6.82 (m. 2H), 7.15 (d, J=8.4 Hz, 1H); IR (KBr) 3406, 2946, 1741, 1614 cm$^{-1}$; MS (FAB) m/e 333.2182 (333.2178 calcd. for C$_{19}$H$_{29}$N$_2$O$_3$).

Example 35

Preparation of the compound represented by the formula 140:

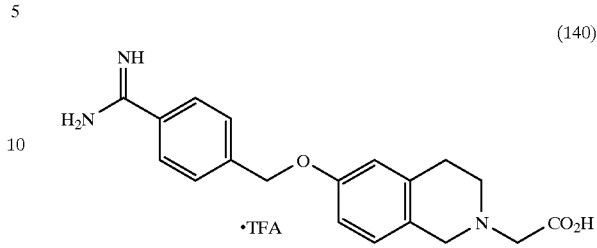

(140)

Part A:

A mixture of 2 (0.5 g, 2.0 mmol) and THF (10 mL) was treated with LiAlH$_4$ (0.15 g, 4.0 mmol) and the resulting mixture was maintained at reflux for 16 hours. The mixture was allowed to cool to room temperature and then quenched with H$_2$O and 15% NaOH. The resulting mixture was filtered and concentrated. The crude product of reduction was taken up in THF/H$_2$O (1:1, 10 mL) and treated with Boc$_2$O (0.64 g, 2.9 mmol) and K$_2$CO$_3$ (0.41 g. 2.9 mmol). The resulting mixture was stirred at room temperature for 2 hours and then diluted with EtOAc. The organic material was washed with H$_2$O and concentrated. The crude isolate was chromatographed on silica (1:1 hexanes/EtOAc) giving 0.58 g of pure 131.

Part B:

A mixture of 131 (0.58 g), Pd/C (10% on carbon, 0.58 g), and EtOAC (30 mL) was maintained under an atmosphere at H$_2$ (balloon) for i hour and then filtered and concentrated. Recovered 0.46 g of essentially pure 136.

Part C:

A mixture of 136 (0.46 g, 1.95 mmol), K$_2$CO$_3$ (0.3 g, 2.1 mmol), α-bromo-p-tolunitrile (0.42 g, 2.1 mmol), Bu$_4$NI (cat), and acetone was maintained at reflux for 6 hours. The reaction mixture was then diluted with EtOAc and washed with H$_2$O. The organic material was concentrated and the crude residue was purified by chromatography (1:1 hex/EtOAc) giving 0.34 g of 137.

Part D:

A mixture of 137 (0.34 g ,0.94 mmol) and TFA (10 mL) was maintained at room temperature for 1 hour and then concentrated. The residue was taken up in saturated aqueous NaHCO$_3$ and the resulting mixture was extracted with EtOAc. The extracts were combined and concentrated. The crude residue taken up in CH$_3$CN (10 mL) and the resulting solution was treated with K$_2$CO$_3$ (0.14 g, 1.0 mmol) and tert-butyl bromoacetate (0.20 g, 1.0 mmol). The resulting mixture was stirred at 60° C. for 2.5 hours and then diluted with EtOAc. The organic material was washed with H$_2$O and concentrated. The crude residue was purified on silca (2.5:1 hexanes/EtOAc) giving 0.18 g of 138.

Part E:

Following the procedure outlined for the preparation of 6 (Example 1 part E), 139 was prepared in 33% yield starting from 0.18 g of 138.

Part F:

Following the procedure outlined for the preparation of 7 (Example 1 part F), 140 was prepared in 66% yield starting from 0.075 g of 139.

$^1$H NMR (300 MHz CD$_3$OD) 3.19 (m, 2H), 3.62 (m, 2H), 4.05 (s, 2H), 4.21 (s, 2H), 6.92 (m, 2H), 7.11 (d, J=8.3 Hz, 1H), 7.65 (d, J=8.4 Hz, 2H), 7.82 (d, J=8.4 Hz, 2H); IR (KBr) 3333, 3104, 1668, 1617, 1191 cm$^{-1}$; MS (FAB) m/e 340.1.

Example 36

Preparation of the compound represented by the formula 146:

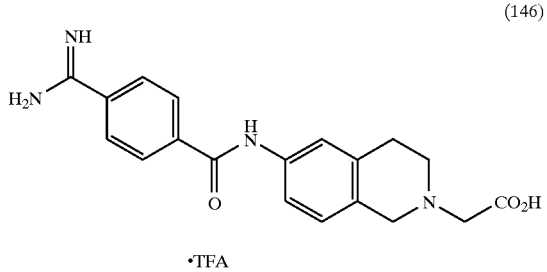

Part A:

A mixture of 141 (12.3 g, 60.2 mmol) and 5N HCl (75 mL) was maintained at reflux for 12 hours and then concentrated to dryness. The residue was taken up in saturated aqueous $NaHCO_3$ and this mixture was extracted with EtOAc. The extracts were then dried over $NaSO_4$ and concentrated. The crude product was purified on silica (15:85 MeOH/$CH_2Cl_2$ giving 5.0 g of 142 as a tan solid.

Part B:

A mixture of 142 (2.6 g, 16.0 mmol), benzyl bromide (5.5 g, 32.0 mmol), $K_2CO_3$ (4.43 g, 32.0 mmol), $CH_3CN$ (30 mL), and $Bu_4NI$ (cat) was maintained at reflux for 3.5 hours and then diluted with EtOAc and washed with $H_2O$. The organic material was dried and concentrated.

Chromatography (15:85 MeOH/$CH_2Cl_2$) allowed the isolation of a fraction containing both mono and dibenzylated material. This mixture was dissolved in THF and the resulting solution was treated with $LiAlH_4$ (1.52 g, 40 mmol). The mixture was refluxed for 4 hours and then quenched with water and 15% NaOH. The resulting mixture was filtered and concentrated. The crude product thus isolated was immediately taken up in THF/$H_2O$ and treated with $BOC_2O$ (3.84 g, 17.6 mmol) and $K_2CO_3$ (6.6 g, 48.0 mmol). After 1 hour, the mixture was diluted with EtOAc and washed with $H_2O$ and brine. The organic material was concentrated and the crude isolate was purified on silica giving 6.25 g of a mixture of mono-benzyl and di-benzylated tetrahydroisoquinolines. This mixture was subjected to catalytic hydrogenation (Pd/C) in EtOH giving 1.92 g of pure 143 after chromatography (1:3 MeOH/$CH_2Cl_2$) on silica.

Part C:

A mixture of 143 (1.92 g, 8.2 mmol), p-cyanobenzoic acid (1.2 g, 8.2 mmol), EDCI (1.7 g, 9.0 mmol), and DMAP (cat) in $CH_2Cl_2$ (20 mL) was maintained at room temperature for 2 hours. The mixture was then diluted with EtOAc and washed with $H_2O$. The organic material was then concentrated giving crude 144 whose purity was sufficient for the next reaction. Crude 144 was dissolved in TFA and allowed to stand at room temperature for 1 hour and was then concentrated. The residue was taken up in saturated aqueous $NaHCO_3$ and the resulting mixture was extracted with EtOAc. The organic extracts were concentrated giving the desired amine. Chromatography (silica, 10% TEA in MeOH) gave 1.23 g of material whose purity was sufficient for the next step. A mixture of this material (1.2 g, 4.7 mmol), t-butyl bromoacetate (0.99 g, 5.1 mmol) $K_2CO_3$ (0.70 g, 5.1 mmol), $BU_4NI$ (cat) and $CH_3CN$ was stirred at room temperature for 3 hours. The mixture was then diluted with EtOAc and washed with $H_2O$. The organic material was dried $NaSO_4$ and concentrated. Chromatography (1:9 MeOH/$CHCl_3$) gave 0.62 g of 145 as a yellow oil.

Part E:

Following the general procedure employed for the preparation of 6 (Example 1 part E), 146 was obtained in 26% yield starting from 0.1 g of 145.

Part F:

Following the general procedure employed for the preparation of 7 (Example 1 part F), 147 was obtained in 80% yield from 0.034 g of 146.

$^1$H NMR (300 MHz $CD_3OD$) 3.23 (m, 2H), 3.62 (m, 2H), 4.10 (s, 2H), 4.51 (m, 2H), 7.2 (d, J=8.2 Hz, 1H), 7.6 (m, 1H), 7.75 (S, 1H), 7.92 (d, J=8.4 Hz, 2H), 8.16 (d, J=8.4 Hz, 2H).

Example 37

Preparation of the compound represented by the formula 155:

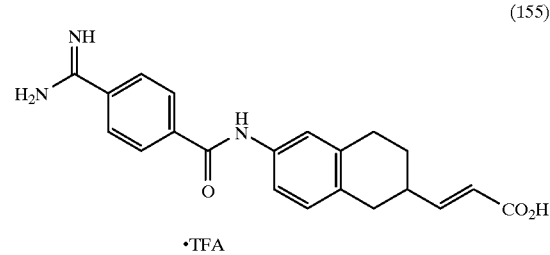

Part A:

A solution of ester 148 (0.81 g, 3.23 mmol), and THF (7 mL) was treated with $LiBH_4$ (0.14 g, 6.5 mmol) and allowed to stand at room temperature for 6 hours. The mixture was then diluted with EtOAc and washed with $H_2O$. The organic material was concentrated giving 0.65 g of material whose purity was sufficient for the next step. A mixture of this material(0.65 g, 3.1 mmol), TBSCl (0.51 g, 3.5 mmol) imidazole (0.24 g, 3.47 mmol), and DMF (5 mL) was maintained at room temperature for 1 hour. The mixture was then diluted with EtOAc and washed with $H_2O$. The organic material was concentrated and the crude residue was purified on silica (5:1 hexanes/EtOAc) giving 0.96 g of pure 149.

Part B:

A mixture of 149 (0.96 g) and Pd/C (10% on carbon, 0.96 g) in EtOAc was maintained under an atmosphere of $H_2$ (balloon) for 1 hour and then filtered and concentrated. The crude isolate was taken up in $CH_2Cl_2$ (5 mL) and treated with p-cyanobenzoic acid (0.45 g, 3.1 mmol), EDCI (0.64 g, 3.34 mmol), and DMAP (cat). The resulting solution was maintained at room temperature for 2 hours and then diluted with EtOAc. The organic material was washed with $H_2O$ and then concentrated. Chromatography (1:1 hexanes/EtoAc) gave 1.09 g of pure 150.

Part C:

A mixture of 150 (1.09 g, 2.59 mmol) and TBAF (5.2 mL at a 1M solution in THF, 5.2 mmol) was maintained at room temperature for 1 hour. This mixture was diluted with EtOAc, washed with $H_2O$, and then concentrated giving 0.71 g of essentially pure primary alcohol. This material (0.65 g, 2.11 mmol) was oxidized with DMSO, oxalyl chloride, and TEA (method of Swern). The crude isolate thus obtained was taken up in THF (5 mL) and added to a mixture of t-butyl diethylphosphonoacetate (0.71 g, 3.2 mmol), NaH (0.13 g at a 60% dispersion in oil, 3.2 mmol) and THF (10 mL). After 1 hour, the mixture was diluted with EtOAc and washed with $H_2O$. The organic material was then concentrated and the crude residue was fractionated on silica (5:1 hexanes/EtOAc) giving 0.27 g of 151, 0.197 g of 152, and 0.47 g of recovered starting alcohol.

Part D:

Following the procedure described for the preparation of 7, (Example 1 part E and F) 155 was prepared in 54% yield starting from 0.27 g of 152.

$^1$H NMR (300 MHz CD$_3$OD) 1.65 (m, 1H), 2.05 (m, 1H), 2.60–2.95 (m, 5H), 5.85 (d, J=15.5 Hz, 1H), 7.05 (dd, J=9.6, 15.8 Hz, 1H), 7.10 (d, J=8.3 Hz, 1H), 7.4 (m, 2H), 7.91 (d, J=8.4 Hz, 2H), 8.17 (d, J=8.4 Hz, 2H); IR (KBr) 3313, 3102, 1670, 1203 cm$^{-1}$; MS (FAB) m/e 364. Anal. Calcd. for C$_{23}$H$_{22}$N$_3$O$_5$F$_3$: C, 57.86; H, 4.65,; N, 8.80. Found: C, 57.59; H, 4.84; N, 8.78.

Example 38

Preparation of the compound represented by the formula 154:

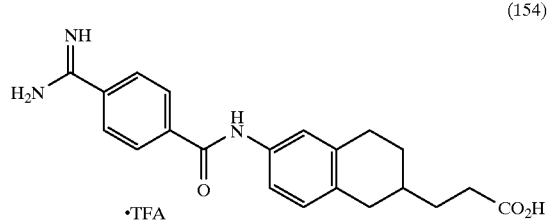

(154)

Part A:

A mixture of 151 (0.18 g, 0.43 mmol) and Pd/C (10% on carbon, 0.18 g) in EtOH was maintained under an atmosphere of H$_2$ (balloon) for 30 minutes and then was filtered and concentrated. Chromatography (3:1 hexanes/EtOAc) gave 0.09 g of 153 as a clear oil.

Part B:

Following the general procedure employed for the preparation of 7 (Example 1 part E and F), 154 was prepared in 51% yield starting from 0.09 g of 153.

$^1$H NMR (300 MHz CD$_3$OD) 1.4 (m, 1H), 1.7 (m, 3H), 1.97 (m, 1H), 2.4 (m, 3H), 2.85 (m, 3H), 7.08 (d, J=8.3 Hz, 1H), 7.40 (m, 2H), 7.90 (d, J=8.4 Hz, 2H), 8.17 (d, J=8.4 Hz, 2H); IR (KBr) 3317, 3102, 2926, 1708, 1666, 1142 cm$^{-1}$; MS (FAB) m/e 366.1815 (366.1818 calcd. for C$_{21}$H$_{24}$N$_3$O$_3$).

Example 39

Preparation of the compound represented by the formula 161:

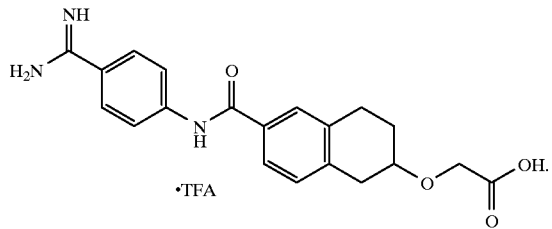

Part A:

A mixture of 6-bromotetralone 156 (1.0 g, 4.4 mmol) and EtOH (10 mL) was treated with NaBH$_4$ (1 g) at room temperature. After 1 hour, the mixture was diluted with EtOAc and washed with H$_2$O. The organic material was concentrated to dryness and the crude isolate was dissolved in dry DMF (10 mL) and treated with TBSCl (1.0 g, 6.6 mmol) and imidazole (0.45 g, 6.6 mmol). The resulting solution was allowed to stand at room temperature overnight. This mixture was then diluted with EtOAc and washed with H$_2$O and concentrated. The crude isolate was purified on silica (hexanes) giving 0.8 g of 157 (52%) as a clear oil.

Part B:

A mixture of 157 (1.93 g, 5.7 mmol) and THF (25 mL) was treated with t-BuLi (8.4 mL of 1.7M solution in pentane) at −78° C. After 30 minutes, a stream of dry CO$_2$ was bubbled through the solution and the reaction was allowed to warm to room temperature. The resulting THF mixture was diluted with H$_2$O, acidified with 1N HCl, and extracted with EtOAC. The extracts were concentrated affording 1.50 grams of crude acid. A 0.5 g (1.63 mmol) portion of this material was dissolved in CH$_2$Cl$_2$ (2.0 mL) and the resulting solution was treated with benzyl alcohol (0.19 g, 1.8 mmol), EDCI (0.34 g, 1.8 mmol) and DMAP (cat). This mixture was allowed to stand for two hours and then was diluted with EtOAc and washed with H$_2$O. The organic material was concentrated and the crude residue treated with TBAF (1.8 mL of a 1M solution in THF, 1.8 mmol). After 25 minutes, the mixture was diluted with EtOAc and washed with H$_2$O. The organic material was concentrated affording 0.45 g of 158 as an essentially pure oil.

Part C:

A mixture of 158 (0.45 g, 1.59 mmol), t-butyl bromoacetate (0.96 g, 4.9 mmol) benzene (5 mL), 50% aqueous NaOH (5 mL), and Bu$_4$NHSO$_4$ (cat) was stirred rapidly at room temperature for 5 hours. The mixture was then diluted with EtOAc and washed with H$_2$O. The organic material was concentrated and the crude residue purified on silica (5:1 hexanes/EtOAc) giving 0.44 g (69%) of the desired alkylated product as a clear oil. A mixture of this material (0.44 g, 1.1 mmol), Pd/C (10% on carbon, 0.44 g) and EtOAC (10 mL) was stirred under an atmosphere of H$_2$ (balloon) for 2 hours. The material was then filtered and concentrated giving a 0.29 g of essentially pure 159.

Part D:

A mixture of 159 (0.29 g, 0.94 mmol), EDCI (0.2 g, 1.0 mmol) 4-aminobenzonitrile (0.12 g, 1.0 mmol), DMAP (cat) and CH$_2$Cl$_2$ (5 mL) was maintained at room temperature for 4 hours. This mixture was then diluted with EtOAc and washed with H$_2$O. The organic material was then concentrated. Chromatography (2.5:1 hexanes/EtOAc) gave a fraction (0.28 g) containing the desired amide 160 and what is presumed to be the symmetrical anhydride of 159. This material was taken on to the next step.

Part E:

The material obtained in the previous step (0.28 g) was taken up in pyridine (20 mL) and TEA (2 mL) and the resulting solution was saturated with H$_2$S. This mixture was allowed to stand at room temperature for 12 hours and then diluted with EtOAc and washed with H$_2$O. The organic material was concentrated and the crude mixture was chromatographed on silica (EtOAc) giving 0.13 g of pure intermediate thioamide. This material was then processed in the same fashion as described in example 1 part E, ultimately giving 0.07 g of pure Boc protected material. This material was taken up in TFA and stirred at room temperature for 1 hour and then concentrated giving 0.056 g of 161.

$^1$H NMR (300 MHz CD$_3$OD) 1.92–2.17 ( m, 2H), 2.80–3.22 (m, 4H), 4.05 (m, 1H), 4.22 (s, 2H), 7.27 (d, J=8.3 Hz, 1H), 7.72 (m, 2H), 7.82 (d, J=8.4 Hz, 2H), 8.02 (d, J=8.4 Hz, 2H); IR (KBr) 3318, 3147, 1739, 1656, 1137 cm$^{-1}$; MS (FAB) m/e 368.

Example 40

Preparation of the compound represented by the formula 168:

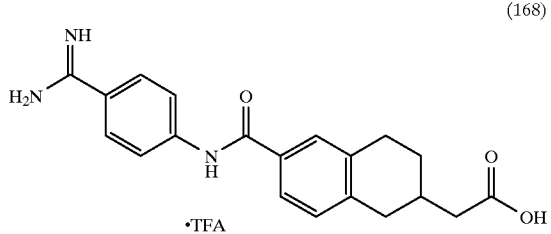

(168)

Part A:

A mixture of 156 (1.25 g, 5.5 mmol), ethylene glycol (3.4 g, 55 mmol), TsOH (cat), and benzene (25 mL) was maintained at reflux with $H_2O$ removal for 3 hours. The mixture was then diluted with EtOAc and the resulting solution was washed with 1N NaOH. The organic material was then concentrated and the crude residue purified by chromatography (5:1 hexanes/EtOAc) giving 1.15 g (77%) of 162 as a clear oil.

Part B:

A solution of 162 (1.15 g 4.3 mmol) and THF (15 mL) was treated with t-BuLi (6.3 mL of a 1.7M solution in pentane, 10.7 mmol) at −78° C. for 30 minutes and then quenched by the addition of $CO_2(g)$. The reaction mixture was allowed to warm to room temperature and then was diluted with $H_2O$. The resulting mixture was acidified with concentrated HCl and extracted with EtOAc. The organic extracts were concentrated and the crude isolate was taken up in $CH_2Cl_2$ (10 mL) and treated with benzyl alcohol (0.58 g, 5.4 mmol), EDCI (1.02 g, 5.4 mmol), and DMAP (cat). The resulting solution was maintained at room temperature overnight and then diluted with EtOAc and washed with $H_2O$. The organic material was concentrated and the crude residue chromatographed on silica giving one fraction (1.06 g) which contained the desired product 163 and benzyl alcohol in a 1:1 ratio. This material was suitable for use in the next reaction.

Part C:

The above mixture was dissolved in acetone (20 mL) and treated with 1N HCl (2 mL) and maintained at reflux for one hour. The mixture was then diluted with EtOAc and washed with saturated aqueous $NaHCO_3$. The organic material was then concentrated. The crude isolate was taken up in THF and added to a mixture of t-butyl diethylphosphonoacetate (1.1 g, 4.93 mmol), NaH (0.1 g of a 60% dispersion in oil, 4.93 mmol), and THF (25 mL) at −78° C. The resulting solution was allowed to warm to room temperature and then maintained at reflux for one hour. The mixture was then diluted with EtOAc and washed with $H_2O$. The organic material was concentrated and the crude isolate was purified on silica (2.5:1 hexanes/EtOAc) giving 0.47 g of 164 as a mixture of olefin isomers.

Part D:

A mixture of 164 (0.47 g) and Pd/C (10% on carbon, 0.47 g) in EtOH was maintained under an atmosphere of $H_2$ (balloon) for 2 hours and then filtered and concentrated giving 0.29 g of essentially pure 165.

Part E:

A mixture of 165 (0.29 g, 1.0 mmol), EDCI (0.28 g, 1.5 mmol), p-cyanobenzoic acid (0.12 g, 1.0 mmol), DMAP (cat), and $CH_2Cl2$ (5 mL) was maintained at 100° C. in a sealed tube for 2 h and then diluted with EtOAc and wash ed with $H_2O$. The organic material was concentrated and the residue chromatographed on silica (80:1 $CHCl_3$/THF) giving 0.28 g (69%) of 166.

Part F:

Following the procedure outlined for the preparation of 6 (Example 1 part E), 167 was prepared in 56% yield starting from 0.28 g of 166.

Part G:

Following the procedure outlined for the preparation of 7 Example 1 part F), 168 was prepared in 91% yield starting from 0.22 g of 167.

$^1$H NMR (300 MHz $CD_3OD$) 1.5 (m, 1H), 2.0 (m, 1H), 2.2 (m, 1H), 2.35–2.55 (m, 3H), 2.95 (m, 3H), 7.05 (d, J=8.25 Hz, 1H), 7.4 (m, 2H), 7.93 (d, J=8.4 Hz, 2H), 8.15 (d, J=8.4 Hz, 2H); IR (KBr) 3322, 3104, 1712, 1667, cm$^{-1}$; MS (FAB) m/e 352.1654 (352.1661 calcd. for $C_{20}H_{22}N_3O_3$).

Example 41

Preparation of the compound represented by the formula (177):

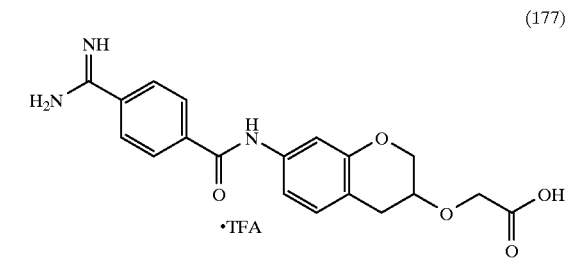

(177)

Part A:

A mixture of 169 (3.5 g) and Claison's alkali (NaOH in EtOH) (75 mL) was maintained at reflux for 6 hours and then allowed to cool. The mixture was concentrated to ½ volume and the remaining aqueous material neutralized to pH 7 with concentrated HCl. The mixture was then extracted with EtOAc and the combined extracts concentrated. The residue was taken up in THF/$H_2O$ (1:1, 20 mL) and treated with $K_2CO_3$ (3.2 g, 23 mmol), and CBz chloride (3.92 g, 23 mmol). The mixture was rapidly stirred for 1 hour and then diluted with EtOAc and washed with $H_2O$. The organic material was concentrated and the crude residue was subjected to acylation with $Ac_2O$ (5 mL) in pyridine (10 mL). After 2 hours the mixture was concentrated to dryness and the residue chromatographed (3:1 hexanes/EtOAc) giving 6.42 g of pure 170.

Part B:

A mixture of 170 (6.42 g, 19.75 mmol), MCPBA (4.27 g, 24.69 mmol), and $CH_2Cl_2$ (40 mL) was maintained at room temperature for 15 hours. At this time, the mixture was diluted with EtOAc and washed with saturated aqueous $NaHCO_3$ and $H_2O$. The organic material was then concentrated. The crude material was taken up in acetone (450 mL) and treated with NaI (4 g). The resulting solution was maintained at reflux for 4 hours and then allowed to cool. The mixture was concentrated, dissolved in EtOAc, washed with $H_2O$, and reconcentrated. This material was then treated with 0.1N LiOH (290 mL) in THF (290 mL) for 12 hours. The mixture was diluted with EtOAc and washed with $H_2O$ and the remaining organic material was concentrated. Chromatography (2:1 hexanes/EtOAc) gave 3.58 g of 171.

Part C:

A mixture of 171 (6.8 g, 2.6 mmol), TBSCl (0.43 g, 2.9 mmol), imidazole (0.21 g, 3.2 mmol), and DMF (5 mL) was stirred at room temperature for 16 hours. This material was then diluted with EtOAc and washed with $H_2O$. The organic material was concentrated giving essentially pure TBS ether. A mixture of this material (0.98 g, 2.4 mmol), and THF (10 mL) was treated with NaH (0.07 g of a 60% dispersion in oil, 2.6 mmol) and allowed to stand for 1 hour. The mixture was then treated with benzylbromide (0.45 g, 2.6 mmol) and $Bu_4NI$ (cat) and allowed to stand for 5 hours. The mixture was then diluted with EtOAc and washed with $H_2O$. The organic material was then concentrated. The crude residue was taken up in THF and treated with TBAF (2.9 mL of a 1M solution in THF, 2.9 mmol). After one hour at room temperature, the mixture was diluted with EtOAc and washed with $H_2O$. The organic material was concentrated and the crude material was chromatographed on silica (hexanes/EtOAc 1:1) giving 0.94 g (95%) of 172.

Part D:

Following the procedure employed for the preparation of 68 (Example 24 part B), 173 was prepared in 80% yield starting from 0.43 g of 172.

Part E:

A mixture of 173 (0.65 g, 1.16 mmol), and Pd/C (10% on carbon, 0.65 g) in EtOH (10 mL) was maintained under an atmosphere of $H_2$ (balloon) for 2.5 hours and then filtered and the filtrate concentrated. The crude material was then taken up in $CH_2Cl_2$ (5 mL) and treated with EDCI (0.23 g, 1.2 mmol), p-cyanobenzoic acid (0.18 g, 1.2 mmol) and DMAP (cat). The resulting solution was maintained at room temperature for 1 hour and then diluted with EtOAc. The resulting mixture was washed with $H_2O$ and then concentrated. The crude residue was chromatographed on silica (1:2 hexanes/EtOAc) giving 0.32 g (71%) 175.

Part F:

Following the procedure employed for the preparation of 6 (Example 1 part E), 176 was prepared in 59% yield starting from 0.31 g of 175.

Part G:

Following the procedure employed for the preparation of 7 (Example 1 part F), 177 was prepared in 70% yield starting from 0.23 g of 176.

$^1$H NMR (300 MHz $CD_3OD$) 2.85 (dd, J=5.4, 16.4 Hz, 1H), 3.06 (dd, J=4.4, 16.5 Hz, 1H), 4.0–4.2 (m, 5H), 7.05 (d, J=8.25 Hz, 1H), 7.18 (m, 1H), 7.22 (s, 1H), 7.92 (d, J=8.4 Hz, 2H), 8.10 (d, J=8.4 Hz, 2H); IR (KBr) 3340, 1667, 1603, 1201, cm$^{-1}$; MS (FAB) m/e 370. Anal. Calcd. for $C_{21}H_{20}N_3O_7F_3$: C, 52.18; H, 4.17; N, 8.69. Found: C, 52.15; H, 4.02; N, 8.54.

Example 42

Preparation of the compound represented by the formula 186:

(186)

structure shown: $H_2N$–C(=NH)–phenyl–$CH_2$–O–tetrahydronaphthalenone–$CH_2$–$CO_2H$ · TFA Part A:

To a mixture of 178 (2.17 g, 13.4 mmol) and sodium glyoxylate (4.25 g, 37.4 mmol) was added 1N NaOH (50 mL, 50 mmol). The solution was stirred 4 hours at room temperature, adjusted to pH 1 with conc. HCl, 5N HCl (200 mL) was added and reflux maintained for 24 hours. The mixture was allowed to cool and the resulting precipitate collected. The filtrate was extracted with EtOAc, the combined extracts washed with brine, dried ($MgSO_4$), and concentrated in vacuo to give a solid that was combined with the above precipitate to afford 3.02 g (99%) of 179 as a brown solid without further purification.

Part B:

To a stirred solution of 179 (0.95 g, 4.36 mmol) in glacial $HOAc/H_2O$ (2:1, 15 mL) was added zinc dust (1.0 g, 15.3 mmol). The mixture was heated at reflux for 2 hours, cooled to room temperature, diluted with EtOAc, and washed with 1N HCl, $H_2O$, and brine. The organic material was dried ($MgSO_4$), and concentrated to afford 0.89 g (93%) of 180 as a brown solid without further purification.

Part C:

180 (0.88 g, 4.0 mmol) was dissolved in THF/EtOAc (1:4 25 mL), diphenyldiazomethane added (0.97 g, 5.0 mmol) as a solid and the red solution let stir 5 days at room temperature followed by 4 hours at reflux. The mixture was diluted with EtOAc, washed with 1N HCl, saturated $NaHCO_3$, $H_2O$, and brine, dried ($MgSO_4$), and concentrated in vacuo. The crude isolate was purified by chromatography (silica gel 230–400 mesh, toluene:EtOAc gradient) to afford 0.77 g (50%) of 181 as a tan solid.

Part D:

To a solution of 181 (0.77 g, 2 mmol) in DMF (20 mL) was added $K_2CO_3$ (0.276 g, 2 mmol) as a solid. After stirring 0.5 hours at room temperature, α-bromo-p-tolunitrile (0.40 g, 2.0 mmol) was added as a solid and the solution allowed to stir at room temperature for 4 hours. The mixture was diluted with EtOAc, washed with $H_2O$, 1N HCl, saturated $NaHCO_3$, and brine, dried ($MgSO_4$), and concentrated in vacuo.

The crude material was purified by chromatography (silica gel prep plate, 8:2 toluene:EtOAc) to afford 0.83 g (83%) of 184 as a light yellow solid.

Part E:

Following the general procedure described for the preparation of 6 (Example 1 part E), 185 was prepared in 41% yield starting from 0.8 g of 184.

Part F:

Following the general procedure described for the preparation of 6 (Example 1 part F), 186 was prepared in 41% yield starting from 0.8 g of 185. MS (FD) m/e 355.

Example 43

Preparation of the compound represented by the formula 190:

(190)

structure shown: piperidine–(CH_2)_3–O–tetrahydroisoquinoline–N–C(=O)–C(=O)OH · HCl Part A:

A mixture of 2 (1.0 g, 3.95 mmol) and THF (20 mL) was treated with $LiAlH_4$ (0.30 g, 7.9 mmol) and maintained at reflux for 2 hours. The mixture was allowed to cool to room temperature and then quenched with water and 15% NaOH.

The resulting mixture was filtered and concentrated. The crude material thus obtained was dissolved in pyridine (10 mL) and treated with methyl oxalylchloride (0.38 mL, 4.3 mmol). The resulting mixture was maintained at room temperature for 1 hour and then diluted with EtOAc and washed with H$_2$O. The organic material was concentrated and the crude residue purified on silica (3:1 hexanes/EtOAc) giving 0.65 g of 187.

Part B:

A mixture of 187 (0.65 g) and Pd/C (10% on carbon, 0.65 g) and EtOH (10 mL) was maintained under an atmosphere of H$_2$ (balloon) for 2 hours and then filtered and the filtrate concentrated. This process yielded 0.45 g of essentially pure 188.

Part C:

A mixture of 188 (0.098 g, 0.42 mmol) NaH (0.018 g of a 60% dispersion in oil, 0.46 mmol) and THF (2 mL) was stirred at reflux for 0.5 hour and then treated with 1-tBOC-4-(3-bromopropyl)piperidine (0.141 g, 0.42 mmol). The resulting mixture was maintained at reflux for 8 hours and then diluted with EtOAc and washed with H$_2$O and brine. The organic material was concentrated and the crude isolate was purified on silica (1.5:1 hexanes/EtOAc) giving 0.11 g of 189.

Part D:

A mixture of 189 (0.11 g, 0.25 mmol), NaOH (0.02 g, 0.5 mmol) and EtOH (5 mL) was maintained at room temperature for 1 hour and then concentrated. The residue was taken up in H$_2$O and the mixture acidified to pH 4 with KHSO$_4$. This mixture was extracted with EtOAc and the extracts concentrated. The crude residue was treated with TFA (5 mL) for 1 hour and then concentrated. The residue was taken up in 0.1N HCl and lyophilized giving 0.051 g of 190.

$^1$H NMR (300 MHz CD$_3$OD) 1.2–1.7 (m, 6H), 1.8 (m, 2H), 1.95 (m, 2H), 2.9 (m, 4H), 3.35 (m, 2H), 3.75 (m, 2H), 3.95 (m, 2H), 4.6 (m, 2H), 6.25 (m, 2H), 7.1 (m, 1H); IR (KBr) 2940, 1735, 1653, 1187, cm$^{-1}$; MS (FAB) m/e 347.

Example 44

Preparation of the compound represented by the formula 193:

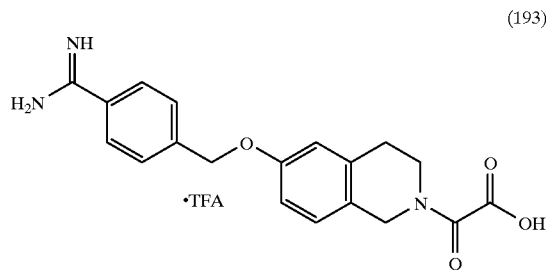

(193)

Part A:

A mixture of 188 (0.19 g, 0.81 mmol), NaH (0.021 g of a 60% dispersion in oil, 0.89 mmol) and THF (5 mL) was stirred at room temperature for 0.5 hour and then treated with α-bromo-p-tolunitrile (0.17 g, 0.89 mmol). The resulting mixture was maintained at reflux for 8 hours and then diluted with EtOAc and washed with H$_2$O. The organic material was concentrated and the crude residue purified on silica (1:1 hexanes/EtOAc) giving 0.22 g of 191.

Part B:

Following the procedure outlined for the preparation of 6 (Example 1 part F), 192 was prepared in 44% yield starting from 0.22 g of 191.

Part C:

A mixture of 192 (0.12 g, 0.27 mmol), NaOH (0.22 g, 0.55 mmol), EtOH (5 mL) was maintained at room temperature for 1 hour and then concentrated. The residue was dissolved in H$_2$O and the resulting solution was acidified to pH 4 with KHSO$_4$. This solution was then lyophilized. The crude residue thus produced was extracted with MeOH and the combined extracts were filtered and concentrated. The isolated material was treated with TFA (5 mL) for 1 hour and then concentrated. In this manner, one isolates 0.05 g of 193.

$^1$H NMR (300 MHz CD$_3$OD) 2.91 (m, 2H), 3.72 (m, 2H), 4.6 (m, 2H), 5.25 (s, 2H), 6.8 (m, 2H), 7.0 (m, 1H), 7.6 (d, J=8.3 Hz, 2H), 7.8 (m, J=8.3 Hz, 2H); IR (KBr) 3336, 3114, 1668, 1506, cm$^{-1}$; MS (FAB) m/e 354.

Assay Methods:

The identification of compounds which are active platelet aggregation inhibitors (PAI) is made possible by the observation that compounds which block the binding of fibrinogen to the GPIIb-IIIa complex in vitro also are capable of inhibiting thrombin or ADP-induced aggregation of human platelets and the formation of platelet-thrombi in vivo. This observation provides the basis for obtaining potent PAI's by evaluating the ability of test materials to disrupt fibrinogen-GP IIb-IIIa interactions.

The following assay methods were used to evaluate the compounds of the invention.

No. 1—The ELISA IIb-IIIa Assay:

In the following assay, GP IIb-IIIa is prepared in purified form, by a method such as described by Fitzgerald, L. A., et al., *Anal Biochem* (1985) 151:169–177, (the disclosure of which is incorporated herein by reference). GP IIb-IIIa is coated onto microtiter plates. The coated support is then contacted with fibrinogen and with the test material and incubated for a sufficient time to permit maximal binding of fibrinogen to the immobilized GP IIb-IIIa. Fibrinogen is typically provided at a concentration of about 5–50 nM and the test material can, if desired, be added at a series of dilution. Typical incubations are 2–4 hr at 25° C., the time and temperature being interdependent.

After incubation, the solution containing the fibrinogen and test material is removed and the level of binding of fibrinogen measured by quantitating bound fibrinogen to GP IIb-IIIa. Any suitable means of detection may be used, but it is convenient to employ labeled fibrinogen, for example using biotinylated labels. Such methods are well known in the art.

A. Description of Assays—Plate Assays

Purified platelet GP IIb-IIIa receptor was prepared as described by Fitzgerald, L. A., et al., *Anal Biochem* (1985) 151:169–177 (1985). Vitronectin receptor was prepared as described by Smith, J. W., *J. Biol Chem* (1988) 263:18726–18731. After purification, the receptors were stored in 0.1% Triton X-100 at 0.1–1.0 mg/ml.

The receptors were coated to the wells of 96-well flat-bottom ELISA plates (Linbro EIA-Plus microtiter plate, Flow Laboratories) after diluting 1:200 with a solution of 20 mM Tris-HCl, 150 mM NaCl, 1 mM CaCl$_2$, pH 7.4, to reduce the Triton X-100 concentration to below its critical micellar concentration and adding an aliquot of 100 ul to each well. The wells were all allowed to incubate overnight at 4° C., and then aspirated to dryness. Additional sites were blocked by the addition of bovine serum albumin (BSA) at 35 mg/ml in the above buffer for 2 hours at 30° C. to prevent nonspecific binding. The wells were then washed once with binding buffer (50 nM Tris-HCl, 100 mM NaCl 2 mM CaCl$_2$, 1 mg/ml BSA).

The corresponding ligands (fibrinogen, von Willebrand Factor, or vitronectin) were conjugated to biotin using commercially available reagents and standard protocols. The labeled ligands were added to the receptor-coated wells at final concentration of 10 nM (100 ul/well) and incubated for 3 hours at 25° C. in the presence or absence of the test samples. After incubation, the wells are aspirated to dryness and bound ligand is quantitated.

The bound protein is detected by the addition of antibiotin antibody conjugated to alkaline phosphatase followed by addition of substrate (p-nitrophenyl phosphate), and determination of the optical density of each well at 405 nM. Decreased color development is observed in wells incubated with test samples which inhibit binding of ligand to receptor.

No. 2—The Platelet Aggregation Assay

In addition to the ELISA IIb-IIIa assay previously described the Aggregation-Human/PRP/ADP Assay is useful for evaluating therapeutic compounds.

Platelet-rich plasma was prepared from healthy human volunteers for use in determining inhibition of platelet aggregation by the compounds. Blood was collected via a 21 gauge butterfly cannula, using a two-syringe technique into $\frac{1}{10}$ volume of 10% trisodium citrate.

Platelet-rich plasma was prepared at room temperature by centrifugation of the citrated whole blood at 100×g for 15 minutes. The platelet rich plasma contained approximately 200–400,000 platelets/$\mu$l.

Platelet-poor plasma was prepared by centrifugation of citrated whole blood at 12,000×g for 2 minutes.

Platelet aggregation was assayed in a 4-channel platelet aggregation profiler (PAP-4, Biodata, Hatboro, Pa.) according to the manufacturers directions. Inhibition of platelet aggregation was studied by adding varying amounts adenosine diphosphate (ADP) to stirred human platelet-rich plasma. Specifically, the human platelet-rich plasma was incubated with the compound being tested for 1 minute at 37° C. prior to the addition of a variety of aggregating agents most often ADP 5 $\mu$M, but also 1 $\mu$g/ml collagen, 1 $\mu$M U46619 and 0.3 $\mu$M platelet activating factor.

TABLE OF ASSAY TEST RESULTS

| Example No. | ELISA IIb/IIIa IC50 uM | Agg: Human/PRP/ADP uM |
|---|---|---|
| 01 | 0.6 | 20 |
| 02 | 0.030 | 0.52 |
| 03 | 0.110 | 1.0 |
| 04 | 0.0033 | 0.1 |
| 05 | 0.033 | 7 |
| 06 | 0.05 | 0.7 |
| 07 | 0.015 | 2 |
| 08 | 0.08 | 0.55 |
| 09 | 0.085 | 0.85 |
| 10 | 0.061 | 0.47 |
| 11 | 0.040 | 0.60 |
| 12 | 0.024 | 0.57 |
| 13 | 0.1 | 0.68 |
| 14 | 0.045 | 0.4 |
| 15 | 0.5 | 0.23 |
| 16 | 0.007 | 0.2 |
| 17 | 45.0 | >100.0 |
| 18 | 11.0 | >100.0 |
| 19 | 13 | >100.0 |
| 20 | 0.3 | 20 |
| 21 | 10 | >100.0 |
| 22 | 0.2 | 2 |
| 23 | 0.19 | 25 |
| 24 | 0.76 | 6.5 |
| 25 | 0.22 | NT |
| 26 | 0.52 | NT |
| 27 | 0.11 | NT |
| 28 | 0.005 | 0.19 |

-continued

TABLE OF ASSAY TEST RESULTS

| Example No. | ELISA IIb/IIIa IC50 uM | Agg: Human/PRP/ADP uM |
|---|---|---|
| 29 | 0.015 | 0.28 |
| 30 | 0.002 | 0.06 |
| 31 | 0.016 | 15 |
| 32 | 0.004 | 0.10 |
| 33 | 0.005 | NT |
| 34 | 0.22 | 2.3 |
| 35 | 0.03 | 0.33 |
| 36 | 0.005 | 0.17 |
| 37 | 0.1 | 4.4 |
| 38 | 0.24 | 2.8 |
| 39 | 0.031 | 0.36 |
| 40 | 0.053 | 1.6 |
| 41 | 0.046 | 0.3 |
| 42 | 0.027 | 0.45 |
| 43 | 1.0 | NT |
| 44 | 0.16 | NT |

Note:
NT = not tested

Pharmaceutical Compositions

Pharmaceutical formulations containing compounds of the invention can be administered orally in the form of tablets, capsules, solutions, emulsions or suspensions, inhaled liquid or solid particles, as a spray, through the skin by an appliance such a transdermal patch, or rectally, for example in the form of suppositories. Administration can also take place parenterally, for example in the form of injectable solutions.

Tablets are prepared by mixing the Active Ingredient ("Active Ingredient" is one or more compounds corresponding to formula I, of the invention) with pharmaceutically inert, inorganic or organic carriers, diluents, and/or excipients. Examples of such excipients which can be used for tablets, are lactose, maize starch or derivatives thereof, talc, stearic acid or salts thereof. Examples of suitable excipients for soft gelatin capsules are vegetable oils, waxes, fats, semisolid and liquid polyols.

Suitable excipients for the preparation of solutions and syrups are water, polyols, sucrose, invert sugar and glucose.

Suitable excipients for injectable solutions are water, alcohols, polyols, glycerol and vegetable oils.

These pharmaceutical products can additionally contain preservatives, solubilizers, stabilizers, wetting agents, emulsifiers, sweeteners, colorants, flavorings, buffers, coating agents and antioxidants.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use.

The Active Ingredient can also be made in microencapsulated form.

Exemplary formulations using the Active Ingredient are described below:

Formulation 1

Hard gelatin capsules are prepared using the following ingredients:

|   |   |
|---|---|
|   | (mg/capsule) |
| Active Ingredient | 250.0 |
| Starch | 305.0 |
| Magnesium stearate | 5.0 |

The above ingredients are mixed and filled into hard gelatin capsules in 560 mg quantities.

Formulation 2

A tablet formula is prepared using the ingredients below:

|   |   |
|---|---|
|   | (mg/tablet) |
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation 3

A dry powder inhaler formulation is prepared containing the following components:

|   |   |
|---|---|
|   | Weight % |
| Active ingredient | 5 |
| Lactose | 95 |

The active mixture is mixed with the lactose and the mixture is added to a dry powder inhaling appliance.

Formulation 4

Tablets, each containing 60 mg of active ingredient, are prepared as follows:

|   |   |
|---|---|
|   | (milligrams) |
| Active ingredient | 60.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 150.0 |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules as produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5

Capsules, each containing 80 mg of medicament are made as follows:

|   |   |
|---|---|
|   | (milligrams) |
| Active ingredient | 80.0 |
| Starch | 109.0 |
| Magnesium stearate | 1.0 |
| Total | 190.0 |

The active ingredient, cellulose, starch, and magnesium stearate are blended passed through a No. 20 mesh U.S. sieve, and filled into hard gelatin capsules in 190 mg quantities.

Formulation 6

Suppositories, each containing 225 mg of active ingredient are made as follows:

|   |   |
|---|---|
| Active Ingredient | 225 mg |
| Saturated fatty acid glycerides to | 2000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of medicament per 5.0 mL dose are made as follows:

|   |   |   |
|---|---|---|
| Active ingredient |   | 50.0 mg |
| Xanthan gum |   | 4.0 mg |
| Sodium carboxymethyl cellulose | (11%) |   |
| Microcrystalline cellulose | (89%) | 50.0 mg |
| Sucrose |   | 1.75 g |
| Sodium benzoate |   | 10.0 mg |
| Flavor |   | q.v. |
| Color |   | q.v. |
| Purified water to |   | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 150 mg of medicament, are made as follows:

|   |   |
|---|---|
|   | (milligrams) |
| Active ingredient | 150.0 |
| Starch | 407.0 |
| Magnesium stearate | 3.0 |
| Total | 560.0 |

The active ingredient, cellulose, starch, and magnesium stearate are blended, passed through a No. 20 mesh U.S. sieve, and filled into hard gelatin capsules in 560 mg quantities.

Method of Treatment

This invention provides a method of preventing or treating thrombosis in mammals, especially humans, which method comprises administering to the human or mammal a therapeutically effective amount of the compounds of this invention. The platelet aggregation inhibitors of the invention are useful therapeutically to prevent thrombus formation. Indications appropriate to such treatment include, without limitation, atherosclerosis and arteriosclerosis, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts "extracorporeal circulating devices"). These syndromes represent a variety of stenotic and occlusive vascular disorders thought to be initiated by platelet activation on vessel walls.

The PAIs may be used for prevention or abortion of arterial thrombus formation, in unstable angina and arterial emboli or thrombosis, as well as treatment or prevention of myocardial infarction (MI) and mural thrombus formation post MI. For brain-related disorders, treatment or prevention of transient ischemic attack and treatment of thrombotic stroke or stroke-in-evolution are included.

The PAIs may also be used for prevention of platelet aggregation, embolization, or consumption in extracorporeal circulations, including improving renal dialysis, cardiopulmonary bypasses, hemoperfusions, and plasmapheresis.

PAIs prevent platelet aggregation, embolization, or consumption associated with intravascular devices, and administration results in improved utility of intraaortic balloon pumps, ventricular assist devices, and arterial catheters.

The PAIs will also be useful in treatment or prevention of venous thrombosis as in deep venous thrombosis, IVC, renal vein or portal vein thrombosis, and pulmonary venous thrombosis.

Various disorders involving platelet consumption, such as thrombotic thrombocytopenic purpura are also treatable.

In addition, the PAIs of the present invention may be used in numerous nontherapeutic applications where inhibiting platelet aggregation is desired. For example, improved platelet and whole blood storage can be obtained by adding sufficient quantities of the compounds, the amount of which will vary depending upon the length of proposed storage time, the conditions of storage, the ultimate use of the stored material, etc. Preferably, the compounds of this invention are administered in the form of a pharmaceutical formulation. Thus, the compounds of this invention may be administered orally, parenterally, topically, rectally and etc., in, appropriate dosage units, as desired.

The term parenteral as used herein includes subcutaneous, intravenous, intraarterial, injection or infusion techniques, without limitation. The term, "topically" encompasses administration rectally and by inhalation spray, as well as the more common routes of the skin and the mucous membranes of the mouth and nose.

Actual dosage levels of active ingredients in the pharmaceutical compositions of this invention may be varied so as to administer an amount of the active compound(s) that is effective to achieve the desired therapeutic response for a particular patient.

The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. If desired, the effective daily dose may be divided into multiple doses for purposes of administration, e.g., two to four separate doses per day. It will be understood, however, that the specific dose level for any particular patient will depend upon a variety of factors including the body weight, general health, diet, time and route of administration, combination with other drugs and the severity of the particular disease being treated.

The range of therapeutic dosages is from about 0.01 to about 10,000 milligrams per day, with from 1 to 300 milligrams being preferred.

Many modifications and variations of this invention may be made without departing from its scope, as is apparent to those skilled in the art. The specific embodiments described herein are offered by way of example only, and the invention is to be limited only by the terms of the appended claims.

We claim:

1. A bicyclic compound having a nucleus formed from two fused six membered rings, A and B, represented by the formula (II), or a pharmaceutically acceptable salt, solvate, or prodrug derivative thereof:

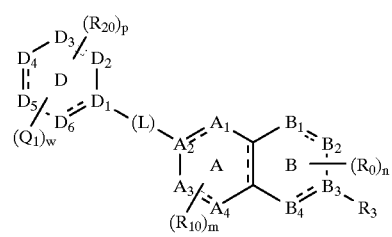

wherein the bicyclic nucleus of rings A and B is selected from the group consisting of formulae (a), (c), (e), and (q) as follows:

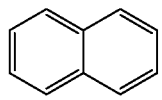

(a)

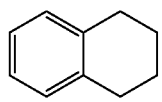

(c)

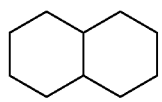

(e)

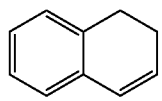

(q)

$R_3$ is an acidic group selected from

[structures of acidic groups including propanoic acid, N-methyl glycine, methoxyacetic acid derivatives, butanoic acid, crotonic acid, N-acetyl sarcosine, acrylic acid, pentenoic acid, benzoic acid derivative, and acetic acid]

n is a number from 2 to 6;

$R_0$ is the same or different and is independently selected from hydrogen, alkyl, halosubstituted alkyl, alkenyl, alkynyl, cycloalkyl, aryl, arylalkyl, hydroxy, alkoxy, arylalkoxy, amino, substituted amino, carbamyl, carboxy, acyl, cyano, halo, nitro, sulfo, =O, =S;

m is a number from 2 to 6;

$R_{10}$ is the same or different and is independently selected from hydrogen, alkyl, halosubstituted alkyl, alkenyl, alkynyl, cycloalkyl, aryl, arylalkyl, hydroxy, alkoxy, arylalkoxy, carboxy, acyl, cyano, halo, nitro, sulfo, =O, and =S;

linking group —(L)— is selected from the group consisting of a bond and the following formulae:

[structures showing Z, Z1-Z2, Z1-Z2-Z3, and Z1-Z2-Z3-Z4 linking groups]

wherein $Z_1$, $Z_2$, $Z_3$, and $Z_4$ are atoms independently selected from the group consisting of carbon, nitrogen, sulfur and oxygen;

D is a six membered ring wherein atoms $D_1$, $D_2$, $D_3$, $D_4$, $D_5$ and $D_6$ are independently selected from carbon, nitrogen, oxygen, or sulfur, with the proviso that at least two of $D_1$, $D_2$, $D_3$, $D_4$, $D_5$ and $D_6$ are carbon;

w is an integer from 1 to 3;

$Q_1$ is an organic group selected from the group consisting of: amino, imino, amidino, aminomethyleneamino, iminomethylamino, guanidino, aminoguanidino, alkylamino, dialkylamino, trialkylamino, alkylideneamino, pyranyl, pyrrolyl, imidazolyl, pyrazolyl, pyridyl, pyrazinyl, pyrimidinyl, pyridazinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, pteridinyl, 4aH-carbozolyl, carbozolyl, beta-carbolinyl, phenanthridinyl, acridinyl, pyrimidinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, and any of the preceding groups substituted with amino, imino, amidino, aminomethyleneamino, iminomethylamino, guanidino, alkylamino, dialkylamino, trialkylamino, or alkylideneamino groups;

$R_{20}$ is the same or different and is independently selected from hydrogen, alkyl, halosubstituted alkyl, alkenyl, alkynyl, cycloalkyl, aryl, arylalkyl, hydroxy, alkoxy, arylalkoxy, amino, substituted amino, carbamyl, carboxy, acyl, cyano, halo, nitro, and sulfo; and p is an integer from 0 to 8.

2. A bicyclic compound having a nucleus formed from two fused six membered rings, A and B, represented by the formula (I), or a pharmaceutically acceptable salt, solvate, or prodrug derivative thereof:

[Formula (I): bicyclic structure with Q-(L)- group attached to ring A having positions A1, A2, A3, A4, fused to ring B with positions B1, B2, B3, B4, with $(R_{10})_m$ on ring A, $(R_0)_n$ and $R_3$ on ring B]

wherein the bicyclic nucleus of rings A and B is selected from the group consisting of formulae (a), (c), (e), and (q) as follows:

(a) [naphthalene structure]

(c) [1,2,3,4-tetrahydronaphthalene structure]

(e) [decahydronaphthalene structure]

(q) [dihydronaphthalene structure]

$R_3$ is an acidic group selected from

[structures of acidic groups: propanoic acid, N-methyl glycine, methoxyacetic acid, butanoic acid, crotonic acid]

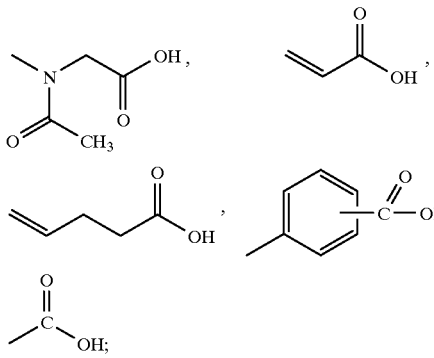

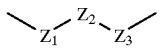

and selected from the group consisting of,

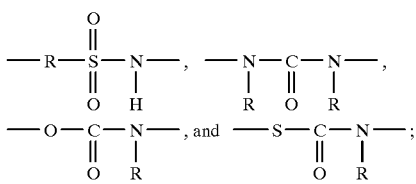

where R is hydrogen or alkyl.

6. A bicyclic tetralin compound having a nucleus formed from two fused six membered rings, represented by the formula (IV), or a pharmaceutically acceptable salt, solvate or prodrug derivative thereof:

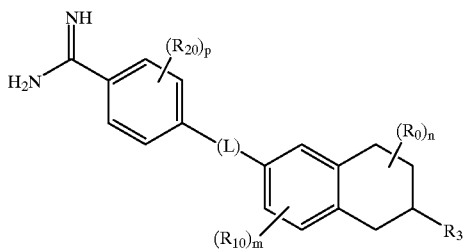

(IV)

wherein;

$R_3$ is an acidic group selected from,

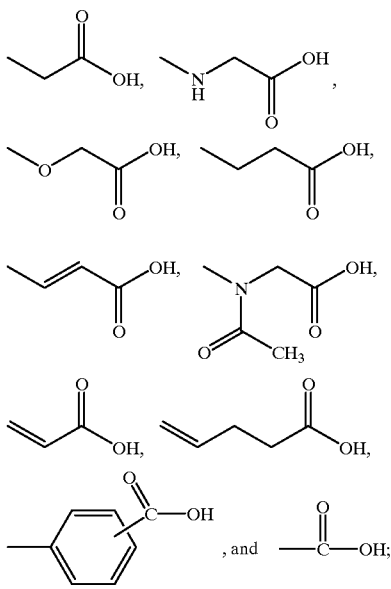

n is a number from 2 to 6;

$R_0$ is the same or different and is independently selected from hydrogen, alkyl, halosubstituted alkyl, alkenyl, alkynyl, cycloalkyl, aryl, arylalkyl, hydroxy, alkoxy, arylalkoxy, amino, substituted amino, carbamyl, carboxy, acyl, cyano, halo, nitro, sulfo, =O, =S;

m is a number from 2 to 6;

$R_{10}$ is the same or different and is independently selected from hydrogen, alkyl, halosubstituted alkyl, alkenyl, alkynyl, cycloalkyl, aryl, arylalkyl, hydroxy, alkoxy, arylalkoxy, carboxy, acyl, cyano, halo, nitro, sulfo, =O, and =S;

linking group —(L)— is selected from the group consisting of a bond and the following formulae:

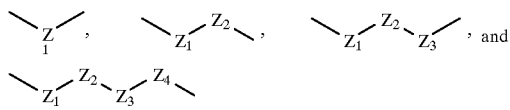

where $Z_1$, $Z_2$, $Z_3$, and $Z_4$ are atoms independently selected from the group consisting of carbon, nitrogen, sulfur and oxygen;

Q is an organic group selected from the group consisting of: amino, imino, amidino, aminomethyleneamino, iminomethylamino, guanidino, aminoguanidino, alkylamino, dialkylamino, trialkylamino, alkylideneamino, pyranyl, pyrrolyl, imidazolyl, pyrazolyl, pyridyl, pyrazinyl, pyrimidinyl, pyridazinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, pteridinyl, 4aH-carbozolyl, carbozolyl, beta-carbolinyl, phenanthridinyl, acridinyl, pyrimidinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, and any of the preceding groups substituted with amino, imino, amidino, aminomethyleneamino, iminomethylamino, guanidino, alkylamino, dialkylamino, trialkylamino, or alkylideneamino group.

3. The compound of claim 2 wherein Q is amino, piperidyl, or guanadino.

4. The compound of claim 2 wherein Q is piperidyl.

5. The compound of claim 1 wherein the —(L)— is a linking group having 3 chain atoms and represented by the formulae:

n is a number from 2 to 6;

$R_0$ is the same or different and is independently selected from hydrogen, alkyl, halosubstituted alkyl, alkenyl, alkynyl, cycloalkyl, aryl, arylalkyl, hydroxy, alkoxy, aralkoxy, amino, substituted amino, carbamyl, carboxy, acyl, cyano, halo, nitro, sulfo, =O, and =S;

m is a number from 2 to 6;

$R_{10}$ is the same or different and is independently selected from hydrogen, alkyl, halosubstituted alkyl, alkenyl, alkynyl, cycloalkyl, aryl, arylalkyl, hydroxy, alkoxy, aralkoxy, carboxy, acyl, cyano, halo, nitro, sulfo, =O, and =S;

linking group —(L)— is a linking group having 1, 3 or 4 chain atoms and represented by the formulae:

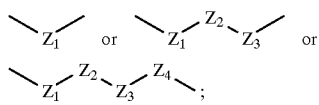

where $Z_1$, $Z_2$, $Z_3$, and $Z_4$ are atoms selected from the group consisting of carbon, nitrogen, sulfur, and oxygen;

$R_{20}$ is the same or different and is independently selected from hydrogen, alkyl, halosubstituted alkyl, alkenyl, alkynyl, cycloalkyl, aryl, arylalkyl, hydroxy, alkoxy, arylalkoxy, amino, substituted amino, carbamyl, carboxy, acyl, cyano, halo, nitro, and sulfo; and p is an integer from 0 to 8.

7. A bicyclic tetralone compound having a nucleus formed from two fused six membered rings, represented by the formula (V), or a pharmaceutically acceptable salt, solvate or prodrug derivative thereof;

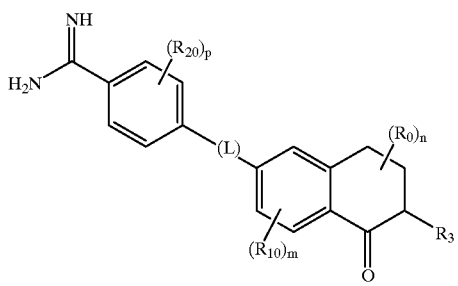

wherein;

$R_3$ is an acidic group selected from,

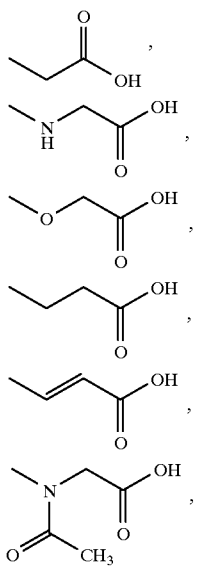

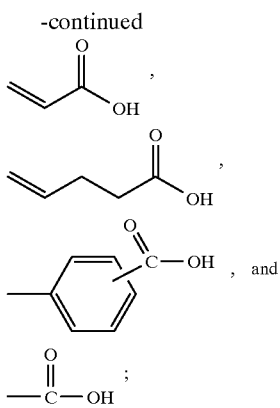

n is a number from 2 to 6;

$R_0$ is the same or different and is independently selected from hydrogen, alkyl, halosubstituted alkyl, alkenyl, alkynyl, cycloalkyl, aryl, arylalkyl, hydroxy, alkoxy, aralkoxy, amino, substituted amino, carbamyl, carboxy, acyl, cyano, halo, nitro, sulfo, =O, and =S;

m is a number from 2 to 6;

$R_{10}$ is the same or different and is independently selected from hydrogen, alkyl, halosubstituted alkyl, alkenyl, alkynyl, cycloalkyl, aryl, arylalkyl, hydroxy, alkoxy, aralkoxy, carboxy, acyl, cyano, halo, nitro, sulfo, =O, and =S;

linking group —(L)— is a linking group having 1, 3 or 4 chain atoms and represented by the formulae:

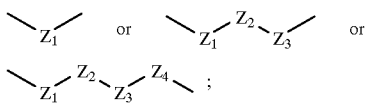

where $Z_1$, $Z_2$, $Z_3$, and $Z_4$ are atoms selected from the group consisting of carbon, nitrogen, sulfur, and oxygen;

$R_{20}$ is the same or different and is independently selected from hydrogen, alkyl, halosubstituted alkyl, alkynyl, cycloalkyl, aryl, arylalkyl, hydroxy, alkoxy, arylalkoxy, amino, substituted amino, carbamyl, carboxy, acyl, cyano, halo, nitro, and sulfo; and p is an integer from 0 to 8.

8. A bicyclic dihydronaphthlene compound having a nucleus formed from two fused six membered rings, represented by the formula (VI), or a pharmaceutically acceptable salt, solvate or prodrug derivative thereof;

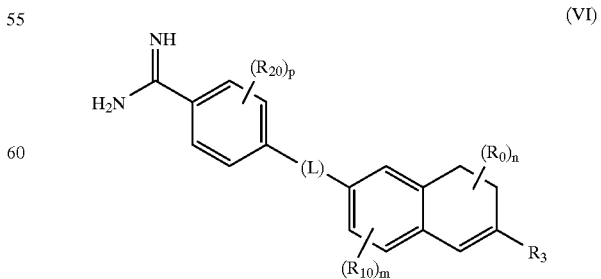

wherein;

R$_3$ is an acidic group selected from,

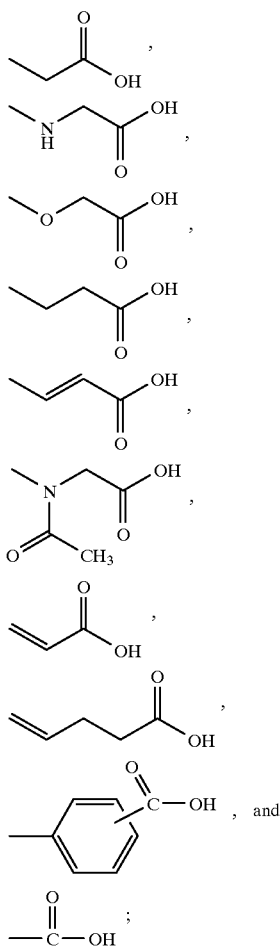

n is a number from 2 to 6;

R$_0$ is the same or different and is independently selected from hydrogen, alkyl, halosubstituted alkyl, alkenyl, alkynyl, cycloalkyl, aryl, arylalkyl, hydroxy, alkoxy, aralkoxy, amino, substituted amino, carbamyl, carboxy, acyl, cyano, halo, nitro, sulfo, =O, and =S;

m is a number from 2 to 6;

R$_{10}$ is the same or different and is independently selected from hydrogen, alkyl, halosubstituted alkyl, alkenyl, alkynyl, cycloalkyl, aryl, arylalkyl, hydroxy, alkoxy, aralkoxy, carboxy, acyl, cyano, halo, nitro, sulfo, =O, and =S;

linking group —(L)— is a linking group having 1, 3 or 4 chain atoms and represented by the formulae:

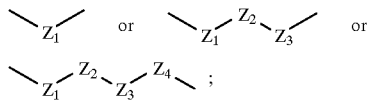

where Z$_1$, Z$_2$, Z$_3$, and Z$_4$ are atoms selected from the group consisting of carbon, nitrogen, sulfur, and oxygen;

R$_{20}$ is the same or different and is independently selected from hydrogen, alkyl, halosubstituted alkyl, alkenyl, alkynyl, cycloalkyl, aryl, arylalkyl, hydroxy, alkoxy, arylalkoxy, amino, substituted amino, carbamyl, carboxy, acyl, cyano, halo, nitro, and sulfo; and p is an integer from 0 to 8.

9. A bicyclic naphthalene compound having a nucleus formed from two fused six membered rings, represented by the formula (VII), or a pharmaceutically acceptable salt, solvate or prodrug derivative thereof;

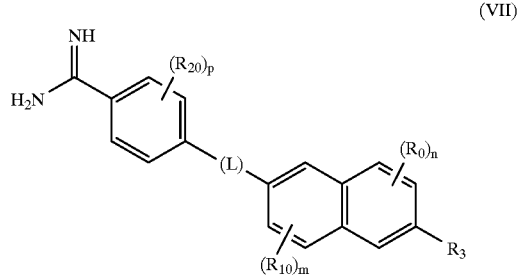

(VII)

wherein;

R$_3$ is an acidic group selected from,

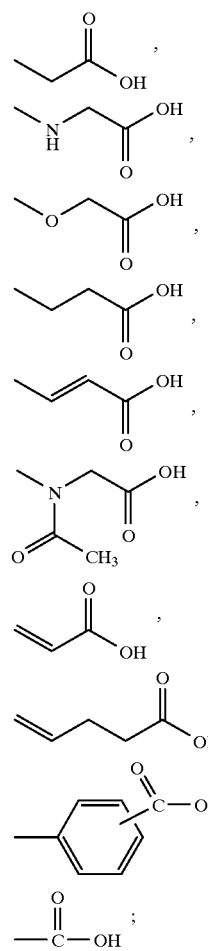

n is a number from 2 to 6;

R$_0$ is the same or different and is independently selected from hydrogen, alkyl, halosubstituted alkyl, alkenyl, alkynyl, cycloalkyl, aryl, arylalkyl, hydroxy, alkoxy, aralkoxy, amino, substituted amino, carbamyl, carboxy, acyl, cyano, halo, nitro, sulfo, =O, and =S;

m is a number from 2 to 6;

$R_{10}$ is the same or different and is independently selected from hydrogen, alkyl, halosubstituted alkyl, alkenyl, alkynyl, cycloalkyl, aryl, arylalkyl, hydroxy, alkoxy, aralkoxy, carboxy, acyl, cyano, halo, nitro, sulfo, =O, and =S;

linking group —(L)— is a linking group having 1, 3 or 4 chain atoms and represented by the formulae:

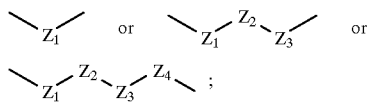

where $Z_1$, $Z_2$, $Z_3$, and $Z_4$ are atoms selected from the group consisting of carbon, nitrogen, sulfur, and oxygen;

$R_{20}$ is the same or different and is independently selected from hydrogen, alkyl, halosubstituted alkyl, alkenyl, alkynyl, cycloalkyl, aryl, arylalkyl, hydroxy, alkoxy, arylalkoxy, amino, substituted amino, carbamyl, carboxy, acyl, cyano, halo, nitro, and sulfo; and p is an integer from 0 to 8.

10. A method for effecting inhibition of platelet aggregation which comprises administering to a mammal in need thereof an effective platelet aggregation inhibiting amount of the bicyclic compound of claim 1.

11. A method of inhibiting fibrinogen binding by contacting glycoprotein IIb–IIIa sites with the compound of claim 1.

12. A method of treating a human to alleviate the pathological effects of atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, and anastomosis of vascular grafts; wherein the method comprises administering to said human at least one bicyclic compound of claim 1; wherein, said bicyclic compound is administered to said human in an amount sufficient to inhibit binding of fibrinogen on glycoprotein IIb–IIIa sites in said human to thereby inhibit said effects.

* * * * *

UNITED STATES PATENT AND TRADEMARK OFFICE
CERTIFICATE OF CORRECTION

PATENT NO.   : 6,137,002
DATED        : October 24, 2000
INVENTOR(S)  : Matthew J. Fisher, Anne Marie Happ, Joseph A. Jakubowski, Michael D. Kinnick, Allen Dale Kline, John Michael Morin, Marshall A. Skelton and Robert Theodore Vasileff It is certified that error appears in the above-identified patent and that said Letters Patent is hereby corrected as shown below:

Title page,
Related U.S. Application Data, "Continuation-in-part" should be -- Continuation --

Column 1,
Line 5, "continuation-in-part" should be -- continuation --

Signed and Sealed this

Twenty-first Day of May, 2002

Attest:

Attesting Officer

JAMES E. ROGAN
*Director of the United States Patent and Trademark Office*